US 12,280,102 B2

(12) United States Patent
Akahata et al.

(10) Patent No.: US 12,280,102 B2
(45) Date of Patent: Apr. 22, 2025

(54) ALPHAVIRUS REPLICON ENCODING CHIMERIC SARS-CoV-2 RECEPTOR BINDING DOMAINS

(71) Applicant: VLP Therapeutics, Inc., Wilmington, DE (US)

(72) Inventors: Wataru Akahata, Kensington, MD (US); Jonathan F. Smith, Redwood City, CA (US); Ryuji Ueno, Easton, MD (US)

(73) Assignee: VLP Therapeutics, Inc., Wilmington, DE (US)

( * ) Notice: Subject to any disclaimer, the term of this patent is extended or adjusted under 35 U.S.C. 154(b) by 236 days.

(21) Appl. No.: 17/232,666

(22) Filed: Apr. 16, 2021

(65) Prior Publication Data

US 2021/0322541 A1 Oct. 21, 2021

Related U.S. Application Data

(60) Provisional application No. 63/088,723, filed on Oct. 7, 2020, provisional application No. 63/050,442, filed on Jul. 10, 2020, provisional application No. 63/011,561, filed on Apr. 17, 2020.

(51) Int. Cl.
*A61K 39/215* (2006.01)
*C07K 14/165* (2006.01)
*C07K 14/18* (2006.01)

(52) U.S. Cl.
CPC .......... *A61K 39/215* (2013.01); *C07K 14/165* (2013.01); *C07K 14/1808* (2013.01); *C07K 2319/02* (2013.01); *C07K 2319/03* (2013.01); *C12N 2770/20034* (2013.01); *C12N 2770/36141* (2013.01)

(58) Field of Classification Search
CPC .............. A61K 39/215; C07K 2319/03; C12N 2770/20034; C12N 2770/36141
See application file for complete search history.

(56) References Cited

U.S. PATENT DOCUMENTS

| | | |
|---|---|---|
| 5,185,440 A | 2/1993 | Davis et al. |
| 5,439,809 A | 8/1995 | Haynes et al. |
| 5,505,947 A | 4/1996 | Johnston et al. |
| 5,580,773 A | 12/1996 | Kang et al. |
| 5,629,204 A | 5/1997 | Honjo et al. |
| 5,639,650 A | 6/1997 | Johnston et al. |
| 5,643,576 A | 7/1997 | Johnston et al. |
| 5,698,520 A | 12/1997 | Honjo et al. |
| 5,792,462 A | 8/1998 | Johnston et al. |
| 5,811,407 A | 9/1998 | Johnston et al. |
| 5,939,598 A | 8/1999 | Kucherlapati et al. |
| 6,008,035 A | 12/1999 | Johnston et al. |
| 6,156,558 A | 12/2000 | Johnston et al. |
| 6,521,235 B2 | 2/2003 | Johnston et al. |
| 6,531,135 B1 | 3/2003 | Johnston et al. |
| 6,541,010 B1 | 4/2003 | Johnston et al. |
| 6,583,121 B1 | 6/2003 | Johnston et al. |
| 6,783,939 B2 | 8/2004 | Olmsted |
| 6,844,188 B1 | 1/2005 | MacDonald et al. |
| 6,982,087 B2 | 1/2006 | Johnston et al. |
| 7,045,335 B2 | 5/2006 | Smith et al. |
| 7,078,218 B2 | 7/2006 | Smith et al. |
| 7,101,550 B2 | 9/2006 | Wood et al. |
| 7,235,235 B2 | 6/2007 | Johnston et al. |
| 7,419,674 B2 | 9/2008 | Chulay et al. |
| 7,425,337 B2 | 9/2008 | Smith et al. |
| 7,442,381 B2 | 10/2008 | Smith et al. |
| 7,531,180 B2 | 5/2009 | Polo et al. |
| 7,572,453 B2 | 8/2009 | Polo et al. |
| 7,595,048 B2 | 9/2009 | Honjo et al. |
| 7,790,181 B2 | 9/2010 | Platteborze et al. |
| 8,158,418 B2 | 4/2012 | Polo et al. |
| 8,263,092 B1 | 9/2012 | Smith et al. |
| 8,460,913 B2 | 6/2013 | Kamrud et al. |
| 8,617,533 B2 | 12/2013 | Smith et al. |
| 8,680,258 B2 | 3/2014 | Coffield et al. |
| 8,709,441 B2 | 4/2014 | Rayner et al. |
| 9,079,943 B2 | 7/2015 | Rayner et al. |
| 9,187,729 B2 | 11/2015 | Depaz et al. |
| 9,249,191 B2 | 2/2016 | Ueno et al. |

(Continued)

FOREIGN PATENT DOCUMENTS

| | | |
|---|---|---|
| CN | 102321639 A | 1/2012 |
| CN | 104293740 A | 1/2015 |

(Continued)

OTHER PUBLICATIONS

Broer, R., et al., Feb. 2006, Important role for the transmembrane domain of severe acute respiratory syndrome coronavirus spike protein during entry, J. Virol. 80(3):1302-1310.*
Hasöksüz, M., et al., 2020, Coronaviruses and SARS-CoV-2, Turk. J. Med. Sci. 50:549-556.*
Weaver, S. C., et al., 2012, Alphaviruses: Population genetics and determinants of emergence, Antivir. Res. 94:242-257.*
Rupp, J. C., et al., 2015, Alphavirus RNA synthesis and non-structural protein functions, J. Gen. Virol. 96:2483-2500.*
Wu, F., et al., Mar. 2020, A new coronavirus associated with human respiratory disease in China, Nature 579:265-284, published online Feb. 3, 2020.*
Li, F., Feb. 2015, Receptor Recognition Mechanisms of Coronaviruses: a Decade of Structural Studies, J. Virol. 89(4):1954-1964.*
Agnihothram, S., et al., Jun. 2018, Development of a Broadly Accessible Venezuelan Equine Encephalitis Virus Replicon Particle Vaccine Platform, J. Virol. 92(11):e00027-18, pp. 1-14.*

(Continued)

*Primary Examiner* — Jeffrey S Parkin
(74) *Attorney, Agent, or Firm* — Sughrue Mion, PLLC

(57) ABSTRACT

Provided herein is an isolated polynucleotide, which encodes alphavirus non-structural proteins nsp1, nsp2, nsp3 and nsp4 and a polypeptide comprising a coronavirus protein fused to a signal sequence and/or transmembrane domain. The coronavirus protein may be the receptor binding domain of the S1 subunit of coronavirus spike (S) protein. The polynucleotide such as RNA is useful for as a vaccine against coronavirus infection, especially, COVID-19 infection.

16 Claims, 10 Drawing Sheets

Specification includes a Sequence Listing.

(56) References Cited

U.S. PATENT DOCUMENTS

| | | |
|---|---|---|
| 9,255,126 B2 | 2/2016 | Polo et al. |
| 9,353,353 B2 | 5/2016 | Nabel et al. |
| 9,363,353 B1 | 6/2016 | Chik |
| 9,416,370 B2 | 8/2016 | Smith et al. |
| 9,441,247 B2 | 9/2016 | Rayner et al. |
| 9,487,563 B2 | 11/2016 | Nabel et al. |
| 9,512,190 B2 | 12/2016 | Ueno et al. |
| 9,597,414 B2 | 3/2017 | Coffield, III et al. |
| 9,637,532 B2 | 5/2017 | Akahata et al. |
| 9,969,986 B2 | 5/2018 | Akahata et al. |
| 10,098,943 B2 | 10/2018 | Akahata et al. |
| 10,111,943 B2 | 10/2018 | Smith et al. |
| 10,434,187 B2 | 10/2019 | Coffield, III et al. |
| 2003/0108521 A1 | 6/2003 | Calatrava |
| 2003/0232324 A1 | 12/2003 | Polo et al. |
| 2005/0214321 A1 | 9/2005 | Rasochova et al. |
| 2007/0122378 A1 | 5/2007 | Freeman et al. |
| 2008/0025067 A1 | 1/2008 | Scheuerlein |
| 2009/0079185 A1 | 3/2009 | Carbines-Evans et al. |
| 2009/0298955 A1 | 12/2009 | Handa et al. |
| 2009/0305950 A1 | 12/2009 | Minato et al. |
| 2009/0312190 A1 | 12/2009 | Chinea Santiago et al. |
| 2010/0196419 A1 | 8/2010 | Compans et al. |
| 2011/0027306 A1 | 2/2011 | Rayner et al. |
| 2011/0035004 A1 | 2/2011 | Maxwell |
| 2011/0081341 A1 | 4/2011 | Honjo et al. |
| 2011/0207223 A1 | 8/2011 | Tang et al. |
| 2011/0262389 A1 | 10/2011 | Mosco |
| 2011/0318373 A1 | 12/2011 | Sasikumar et al. |
| 2012/0003266 A1 | 1/2012 | Nable et al. |
| 2013/0122262 A1 | 5/2013 | Nagakura et al. |
| 2013/0251744 A1 | 9/2013 | Ueno et al. |
| 2014/0120125 A1 | 5/2014 | Ella et al. |
| 2014/0127247 A1 | 5/2014 | Dubensky, Jr. et al. |
| 2014/0170186 A1 | 6/2014 | Nabel et al. |
| 2014/0363458 A1 | 12/2014 | Ueno et al. |
| 2015/0017194 A1 | 1/2015 | Akahata et al. |
| 2015/0299728 A1* | 10/2015 | Rayner .......... A61K 39/21 435/91.1 |
| 2016/0040134 A1 | 2/2016 | Akahata et al. |
| 2016/0074501 A1 | 3/2016 | Akahata et al. |
| 2016/0090403 A1 | 3/2016 | Ueno et al. |
| 2016/0200775 A1 | 7/2016 | Akahata et al. |
| 2016/0303221 A1 | 10/2016 | Nabel et al. |
| 2017/0035871 A1 | 2/2017 | Ueno et al. |
| 2017/0065703 A1 | 3/2017 | Akahata et al. |
| 2017/0096455 A1 | 4/2017 | Baric et al. |
| 2017/0233450 A1 | 8/2017 | Akahata et al. |
| 2017/0252425 A1 | 9/2017 | Akahata et al. |
| 2019/0185822 A1* | 6/2019 | Akahata .......... A61K 39/001162 |

FOREIGN PATENT DOCUMENTS

| | | |
|---|---|---|
| CN | 106085974 A | 11/2016 |
| CN | 106928372 A | 7/2017 |
| JP | 4-506301 A | 11/1992 |
| JP | 2007-512842 A | 5/2007 |
| JP | 2007-537761 A | 12/2007 |
| JP | 2008-543774 A | 12/2008 |
| RU | 2733832 C1 | 10/2020 |
| WO | 93/10152 A1 | 5/1993 |
| WO | 96/37616 A1 | 11/1996 |
| WO | 97/12048 A1 | 4/1997 |
| WO | 99/18226 A2 | 4/1999 |
| WO | 99/41383 A1 | 8/1999 |
| WO | 02/096939 A2 | 12/2002 |
| WO | 03/102166 A2 | 12/2003 |
| WO | 2004/043399 A2 | 5/2004 |
| WO | 2004/085660 A2 | 10/2004 |
| WO | 2006/040334 A1 | 4/2006 |
| WO | 2006/088229 A1 | 8/2006 |
| WO | 2007/003384 A1 | 1/2007 |
| WO | 2007/059715 A2 | 5/2007 |
| WO | 2007/100098 A1 | 9/2007 |
| WO | 2008/025067 A1 | 3/2008 |
| WO | 2009/009215 A2 | 1/2009 |
| WO | 2009/079185 A2 | 6/2009 |
| WO | 2010/062396 A2 | 6/2010 |
| WO | 2011/035004 A1 | 3/2011 |
| WO | 2012/006180 A1 | 1/2012 |
| WO | 2012/023995 A1 | 2/2012 |
| WO | 2012/106356 A2 | 8/2012 |
| WO | 2012/123755 A1 | 9/2012 |
| WO | 2012/172574 A1 | 12/2012 |
| WO | 2013/009884 A1 | 1/2013 |
| WO | 2013/063248 A1 | 5/2013 |
| WO | 2013/122262 A1 | 8/2013 |
| WO | 2013/151764 A1 | 10/2013 |
| WO | 2015/005500 A1 | 1/2015 |
| WO | 2015/139784 A1 | 9/2015 |
| WO | 2015/143335 A1 | 9/2015 |
| WO | 2016/021209 A1 | 2/2016 |
| WO | 2016/109792 A2 | 7/2016 |
| WO | 2016/199936 A1 | 12/2016 |
| WO | 2016/210127 A1 | 12/2016 |
| WO | 2017/009873 A1 | 1/2017 |
| WO | 2017/015463 A2 | 1/2017 |
| WO | 2019/124441 A1 | 6/2019 |
| WO | 2021/138447 A1 | 7/2021 |
| WO | 2021/191630 A1 | 9/2021 |
| WO | 2021/209970 A1 | 10/2021 |

OTHER PUBLICATIONS

Nyon, M. P., et al., 2018, Engineering a stable CHO cell line for the expression of a MERS-coronavirus vaccine antigen, Vaccine 36:1853-1862, available online Feb. 26, 2018.*

Wu, F., et al., 2020, A new coronavirus associated with human respiratory disease in China, Nature 579:265-284, published online Feb. 3, 2020.*

Flint, M., et al., Aug. 1999, Functional Analysis of Cell Surface-Expressed Hepatitis C Virus E2 glycoprotein, J. Virol. 73(8):6782-6790.*

Wang, C., et al., 2017, Novel chimeric virus-like particles vaccine displaying MERS-CoV receptor-binding domain induce specific humoral and cellular immune response in mice, Antivir. Res. 140:55-61, available online Dec. 28, 2016.*

Magini, D., et al., Aug. 2016, Self-Amplifying mRNA Vaccines Expressing Multiple Conserved Influenza Antigens Confer Protection against Homologous and Heterosubtypic Viral Challenge, PLoS One 11(8):e0161193, pp. 1-25.*

Callaway, Coronavirus vaccines: key questions Nature, vol. 579, p. 481, 2020.

Wrapp et al., Cryo-EM structure of the 2019-nCOV spike in the prefusion conformation, Science, vol. 367, 10.1126/science. abb2507, 2020, pp. 1260-1263.

Z. Wang et al., mRNA vaccine-elicited antibodies to SARS-CoV-2 and circulating variants, (preprint) bioRxiv 2021.01.15.426911; doi: https://www.biorxiv.org/content/10.1101/2021.01.15.426911v2, 2021, 52 pages.

Ozharovskaia, T et al., Immunogenicity of Different Forms of Middle East Respiratory Syndrome S Glycoprotein, Acta Nature, 2019, vol. 11, No. 1, 2010, pp. 38-47.

Pillay, Tahir S, Gene of the month: the 2019-nCoV/SARS-CoV-2 novel coronavirus spike protein, Journal of clinical pathology, 2020, vol. 73, No. 7, pp. 366-369.

Agnihothram S. et al., Development of a Broadly Accessible Venezuelan Equine Encephalitis Virus Replicon Particle Vaccine Platform, J. Virol., 2018, vol. 92, Issue 11, e00027-18, https://doi.org/10.1128/JVI.00027-18, pp. 1-14.

Sheahan T. et al., Successful Vaccination Strategies That Protect Aged Mice from Lethal Challenge from Influenza Virus and Heterologous Severe Acute Respiratory Syndrome Coronavirus, J. Virol., 2011, vol. 85, No. 1, pp. 217-230.

Kinney R. M. et al., Attenuation of Venezuelan Equine Encephalitis Virus Strain TC-83 Is Encoded by the 5'-Noncoding Region and the E2 Envelope Glycoprotein, J.Virol., 1993, vol. 67, No. 3, pp. 1269-1277.

(56) References Cited

OTHER PUBLICATIONS

Howard M. W. et al., Aromatic Amino Acids in the Juxtamembrane Domain of Severe Acute Respiratory Syndrome Coronavirus Spike Glycoprotein Are important for Receptor-Dependent Virus Entry and Cell-Cell Fusion, J. Virol., 2008, vol. 82, No. 6, pp. 2883-2894.
Liu Y.V. et al., Chimeric severe acute respiratory syndrome coronavirus (SARS-CoV) S glycoprotein and influenza matrix 1 efficiently form virus-like particles (VLPs) that protect mice against challenge with SARS-CoV, Vaccine, 2011, vol. 29, pp. 6606-6613.
Hetrick B. et al., Development of a novel hybrid alphavirus-SARS-CoV-2 particle for rapid in vitro screening and quantification of neutralization antibodies, antiviral drugs, and viral mutations, bioRxiv, Dec. 23, 2020, doi:https://doi.org/10.1101/2020.12.22.423965, 24 pages.
International Search Report dated Jul. 6, 2021 from the International Searching Authority in International Application No. PCT/JP2021/015773.
Written Opinion dated Jul. 6, 2021 from the International Bureau in International Application No. PCT/JP2021/015773.
Wataru Akahata et al., "A VLP vaccine for epidemic Chikungunya virus protects non-human primates against infection," Nat. Med., 2010, 16(3); 334-338. (pp. 1-12).
Ira Mellman et al., "Cancer immunotherapy comes of age," Nature, 2011, vol. 480 (pp. 480-489).
António Roldão et al., "Virus-like particles in vaccine development", Expert Rev. Vaccines, 2010, 9(10):, pp. 1149-1176.
Gunther Spohn et al., "A Virus-Like Particle-Based Vaccine Selectively Targeting Soluble TNF-α Protects from Arthritis without Inducing Reactivation of Latent Tuberculosis", The Journal of Immunology, 2007, 178: pp. 7450-7457.
Elizabeth V.L. Grgacic et al., "Virus-like particles: Passport to immune recognition", Methods, 2006, 40: pp. 60-65.
Gary T. Jennings et al., "Immunodrugs: Therapeutic VLP-Based Vaccines for Chronic Diseases", Annu. Rev. Pharmacol. Toxicol., 2009, 49: pp. 303-326.
Heinz Leibl et al., "Adjuvant/carrier activity of inactivated tick-borne encephalitis virus", Vaccine, 1998, 16(4): pp. 340-345.
Bryce Chackerian et al., "Determinants of Autoantibody Induction by Conjugated Papillomavirus Virus-Like Particles", The Journal of Immunology, 2002, 169: pp. 6120-6126.
Maria Lia Palomba et al., "CD8+ T-Cell-Dependent Immunity Following Xenogeneic DNA Immunization against CD20 in a Tumor Challenge Model of B-Cell Lymphoma", Clinical Cancer Research, 2005, 370(11): pp. 370-379.
Wendy K. Roberts et al., "Vaccination with CD20 peptides induces a biologically active, specific immune response in mice", Blood, 2002, 99: pp. 3748-3755.
Kathy D. Mccoy et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., 1999, 189(7): pp. 1157-1162.
Gregory J. Atkins et al., "Therapeutic and prophylactic applications of alphavirus vectors", Expert Reviews in Molecular Medicine, 2008, 10(e33): pp. 1-17.
Akahata W., and G.J. Nabel, 2012, "A specific domain of the Chikungunya virus E2 protein regulates particle formation in human cells: implications for alphavirus vaccine design," J. Virol. 86(16): pp. 8879-8883.
Kuo, S.-C., et al., 2012, Cell-based analysis of Chikungunya virus E1 protein in membrane fusion, J. Biomed. Sci. 19(44): pp. 1-12.
Siyang Sun et al: "Structural analyses at pseudo atomic resolution of Chikungunya virus and antibodies show mechanisms of neutralization", eLIFE, Apr. 2, 2013, vol. 2, pp. 1-27.
Carvalho et al., "Malaria Vaccine: Candidate Antigens, Mechanisms, Constraints and Prospects," Scand. J. Immunol., Blackwell Science Ltd. Jul. 1, 2002, vol. 56, pp. 327-343.
Crompton et al., "Advances and Challenges in malaria vaccine development," Science in medicine, The Journal of Clinical Investigation, Dec. 2010, vol. 120, No. 12, pp. 4168-4178.
Malaria Vaccine Program, http://www.globalvaccines.org/content/malaria+vaccine+program/19614, 4 pages total (2012).
Rodriguez D et al., Vaccine Efficacy against malaria by the Combination of Porcine Parvovirus-Like Particles and Vaccinia Virus Vectors Expressing CS of Plasmodium, PLoS One, Apr. 17, 2012, vol. 7, No. 4, e34445. (pp. 1-10).
Oliveira GA et al., Safety and enhanced immunogenicity of a Hepatitis B core particle Plasmodium falciparum Malaria vaccine formulated in adjuvant montanide ISA 720 in a Phase I Trial, Infect. Immun., 2005, vol. 73, No. 6, pp. 3587-3597.
Jones RM et al., A plant-produced Pfs25 VLP Malaria Vaccine Candidate Induces Persistent Transmission Blocking Antibodies against Plasmodium falciparum in immunized mice, PLoS One, Nov. 18, 2013, vol. 8, No. 11, e79538, doi:10.1371/journal.pone.0079538.
Rodrigues M et al., Influenza and Vaccinia viruses expressing Malaria CD8+T and B Cell epitopes. Comparison of their immunogenicity and capacity to induce protective immunity, J. Immunol., 1994, vol. 153, No. 10, pp. 4636-4648. (15 pages).
Pfeiffer B et al., A virosome-mimotope approach to synthetic vaccine design and optimization: synthesis, conformation, and immune recognition of a potential Malaria-vaccine candidate, Angew. Chem. Int. Ed., 2003, vol. 42, No. 21, pp. 2368-2371. (5 pages).
Ghasparian A et al., Engineered synthetic virus-like particles and their use in vaccine delivery, Chembiochem, 2011, vol. 12, No. 1, pp. 100-109.
Dobano C et al., Alphavirus replicon particles are highly immunogenic in the murine Malaria model by homologous or heterologous immunization, Open Vaccine Journal, vol. 1, 2008, pp. 27-37.
Lechner F et al., Virus-like particles as a modular system for novel vaccines, Intervirology, 2002, vol. 45, No. 4-6, pp. 212-217.
Gilbert SC et al., A protein particle vaccine containing multiple Malaria epitopes, Nat. Biotechnol., 1997, vol. 15, No. 12, pp. 1280-1284. (7 pages).
Allsopp CE et al., "Comparison of numerous delivery systems for the induction of cytotoxic T lymphocytes by immunization," Eur. J. Immunol., 1996, vol. 26, No. 8, pp. 1951-1959.
Oliveira-Ferreira et al., "Immunogenicity of Ty-VLP bearing a CD8(+) T cell epitope of the CS protein of P. yoelii: enhanced memory response by boosting with recombinant vaccinia virus.", Vaccine. Mar. 6, 2000; 18(17); 1863-1869.
GenBank: AAW78190.1. circumsporozoite protein, partial [Plasmodium falciparum]. Dec. 29, 2006. (2 pages).
Gregson et al., "Phase 1 Trial of an Alhydrogel Adjuvanted Hepatitis B Core Virus-Like Particle Containing Epitopes of Plasmodium falciparum Circumsporozoite Protein.", PLoS One. Feb. 2008 | vol. 3 | Issue 2| e1556.
Adams et al., "The expression of hybrid HIV: Ty virus-like particles in yeast," Nature Sep. 3-9, 1987; 329(6134); pp. 68-70. (9 pages).
Federico M., "Virus-like particles show promise as candidates for new vaccine strategies," Future Virol. (2010) 5(4); pp. 371-374.
Birkett A et al. "A Modified Hepatitis B Virus Core Particle Containing Multiple Epitopes of the Plasmodium falciparum Circumsporozoite Protein Provides a Highly Immunogenic Malaria Vaccine in Preclinical Analyses in Rodent and Primate Hosts", Infection and Immunity, American Society for Microbiology, US, vol. 70, No. 12; Dec. 1, 2002, pp. 6860-6870.
Milich D R et al. "Conversion of poorly immunogenic malaria repeat sequences into a highly immunogenic vaccine candidate", Vaccine, Elsevier Ltd, GB; vol. 20, No. 5-6; Dec. 12, 2001; pp. 771-788.
Shiratsuchi T. et al. "Replacing adenoviral vector HVR1 with a malaria B cell epitope improves immunogenicity and circumvents preexisting immunity to adenovirus in mice", Journal of Clinical Investigation; vol. 120, No. 10; Oct. 2010; pp. 3688-3701.
Y. Agata et al., "Expression of the PD-1 antigen on the surface of stimulated mouse T and B lymphocytes," International Immunology, 1996, vol. 8, No. 5, pp. 765-772.
F. Notka et al., "Accelerated clearance of SHIV in rhesus monkeys by virus-like particle vaccines is dependent on induction of neutralizing antibodies", Vaccine, 2000, vol. 18, No. 3-4, p. 291-301.

(56) References Cited

OTHER PUBLICATIONS

U. Arora et al., "Virus-like particles displaying envelope domain III of dengue virus type 2 induce virus-specific antibody response in mice", Vaccine, Jan. 2013, vol. 31, No. 6, p. 873-878.
Rodion Gorchakov et al., "Comparative analysis of the alphavirus-based vectors expressing Rift Valley fever virus glycoproteins," Virology, vol. 366 (2007), pp. 212-225.
Sigrid Elshuber et al., "Cleavage of protein prM is necessary for infection of BHK-21 cells by tick-borne encephalitis virus," Journal of General Virology (2003) vol. 84, pp. 183-191.
Simona Ozden et al., "Inhibition of Chikungunya Virus Infection in Cultured Human Muscle Cells by Furin Inhibitors," Journal of Biological Chemistry, vol. 283, No. 32, Aug. 8, 2008 (10 pages total).
Sigrid Elshuber et al., "Resuscitating Mutations in a Furin Cleavage-Deficient Mutant of the Flavivirus Tick-Borne Encephalitis Virus," Journal of Virology, vol. 79, No. 18, Sep. 2005, pp. 11813-11823.
Hevey et al., "Marburg Virus Vaccines Based upon Alphavirus Replicons Protect Guinea Pigs and Nonhuman Primates", Virology, 251: 28-37 (1998).
Bonaldo et al., "Surface Expression of an Immunodominant Malaria Protein B Cell Epitope by Yellow Fever Virus", J. Mol. Biol., 315(4):873-885 (2002).
Vuola et al., "Differential Immunogenicity of Various Heterologous Prime-Boost Vaccine Regimens Using DNA and Viral Vectors in Healthy Volunteers", J. Immunol., 174(1):449-455 (2005).
Calvo-Calle et al., "A Linear Peptide Containing Minimal T- and B-Cell Epitopes of Plasmodium falciparum Circumsporozoite Protein Elicits Protection against Transgenic Sporozoite Challenge", Infection and Immunity, Dec. 2006. vol. 74, No. 12. p. 6929-6939.
Charoensri et al. "An optimized expression vector for improving the yield of dengue virus-like particles from transfected insect cells" Journal of Virological Methods, vol. 205, 2014 (pp. 116-123).
Cox et al. "Predicting Zika virus structural biology: Challenges and opportunities for intervention" Antiviral Chemistry and Chemotherapy, vol. 24 (3-4), 2015 (pp. 118-126).
De Wispelaere Melissanne, et al., "Mutagenesis of the DI/DIII Linker in Dengue Virus Envelope Protein Impairs Viral Particle Assembly", Journal of Virology, 2012, vol. 86, No. 13, pp. 7072-7083, ISSN: 0022-538X, Abstract, Fig.1, Fig.8-9, p. 7073.
GenBank: AAB02517.1, "structural polyprotein precursor [Venezuelan equine encephalitis virus]", dated Nov. 17, 2004, retrieved from https://www.ncbi.nlm.nih.gov/protein/AAB02517.1.
GenBank: ADG95942.1, structural polyprotein [Chikungunya virus] http://www.ncbi.nlm.nih.gov/protein/296124572?report=genbank &log$=protalign&blast_rank=2&FilD=PBR7NTOU015. Dec. 28, 2010.
GenBank "Zika virus strain MR 766, complete genome" AY632535.2, Nov. 23, 2010 (6 pages total) [Retrieved on May 16, 2017] Retrieved from the Internet, URL: <https://www.ncbi.nlm.nih.gov/nuccore/AY632535>.
Haddow A. D. et al., "Genetic Characterization of Zika Virus Strains: Geographic Expansion of the Asian Lineage" PLOS Neglected Tropical Disease, Feb. 2012, vol. 6, Issue 2, e1477 (7 pages total).
Hsieh Szu-Chia, et al., "A strong endoplasmic reticulum retention signal in the stem-anchor region of envelope glycoprotein of dengue virus type 2 affects the production of virus-like particles", Virology, 2008, vol. 374, No. 2, pp. 338-350, ISSN: 0042-6822.
Hsieh Szu-Chia et al. "The length of and nonhydrophobic residues in the transmembrane domain of dengue virus envelope protein are critical for its retention and assembly in the endoplasmic reticulum" Journal of Virology, vol. 84 No. 9, Apr. 2010 (pp. 4782-4797).
WHO Dengue vaccine research, "Immunization, Vaccines and Biologicals", http://www.who.int/immunization/research/development/dengue_vaccines/en/ (total 3 pages).
Huang Claire Y.H., et al., "The dengue virus type 2 envelope protein fusion peptide is essential for membrane fusion", Virology, 2010, vol. 396, No. 2, pp. 305-315, ISSN:0042-6822, Table, Fig.5, pp. 310-313.
Khetarpal Niyati, et al., "Dengue-specific subviral nanoparticles: design, creation and characterization", Journal of Nanobiotechnology, 2013, vol. 11, No. 15, total 8 pages, ISSN: 1477-3155.
Kostyuchenko V et al., "Structure of the thermally stable Zika virus", Nature, May 19, 2016, vol. 533, pp. 425-428.
Larocca et al., "Vaccine Protection Against Zika Virus from Brazil", Nature, Aug. 25, 2016, 536(7617), 474-478, doi:10.1038/nature18952 (24 pages total).
Lin et al., "Analysis of Epitopes on Dengue Virus Envelope Protein Recognized by Monoclonal Antibodies and Polyclonal Human Sera by a High Throughput Assay", PLOS, Jan. 2012, 6(1):e1447, total 12 pages.
Purdy D et al., "Secretion of noninfectious dengue virus-like particles and identification of amino acids in the stem region involved in intracellular retention of envelope protein" Virology, 2005, vol. 333, No. 2, pp. 239-250, ISSN: 0042-6822, Abstract, Fig. 1-4. Table 1, pp. 240, 247-248.
Richner et al. "Modified mRNA vaccines protect against Zika Virus infection" Cell, vol. 168., Mar. 9, 2017 , pp. 1114-1125, (23 pages total).
Seligman S, "Constancy and diversity in the flavivirus fusion peptide", BioMed Central, Virology Journal 2008, Feb. 14, 2008, total 10 pages. URL: http://www.virologyj.com/content/5/1/27.
Taylor et al. "Production of immunogenic West Nile virus-like particles using a herpes simplex virus 1 recombinant vector" Virology, vol. 496, 2016 (pp. 186-193).
Tsai et al., "Complexity of Neutralizing Antibodies against Multiple Dengue Virus Serotypes after Heterotypic Immunization and Secondary Infection Revealed by In-Depth Analysis of Cross-Reactive Antibodies", Journal of Virology, Jul. 2015, vol. 89, No. 14, pp. 7348-7362.
Heinz F et al., "Flaviviruses and flavivirus vaccines", Vaccine 30 (2012) 4301-4306.
Yamaji et al. "Efficient production of Japanese encephalitis virus-like particles by recombinant lepidopteran insect cells" Appl. Microbiol Biotechnol, vol. 97, 2013 (pp. 1071-1079).
Zhang et al., "Vaccination with dengue virus-like particles induces humoral and cellular immune responses in mice", Virology Joumal, 2011, 8:333, total 9 pages.
Zika virus fact sheet, updated Sep. 6, 2016; URL:http://www.who.int/mediacentre/factsheets/zika/en/ ( 5 pages total).
Urakami et al., "Development of a Novel Virus-Like Particle Vaccine Platform That Mimics the Immature Form of Alphavirus," Clinical and Vaccine Immunology, 24(7): e00090-17 (pp. 1-14).
Veltrop-Duits et al., "Human CD4+ T cells stimulated by conserved adenovirus 5 hexon peptides recognize cells infected with different species of human adenovirus", Eur. J. Immunol., 2006, vol. 36, pp. 2410-2423 (14 pages total).
Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pages total).
Palucha et al., "Virus-Like Particles: Models for Assembly Studies and Foreign Epitope Carriers," Progress in Nucleic Acid Research and Molecular Biology, 2005, vol. 30, pp. 135-168.
Vitrop-Duits et al., Human CD4+T cells stimulated by conserved adenovirus 5 hexon peptides recognize cells infected with different species of human adenovirus, Eur. J. Immunol. 2006, vol. 36, pp. 2410-2423.
Metz et al., PLoS One, 2011, vol. 6, Issue 10, pp. 1-10.
Liu et al., "Recombinant dengue virus-like particles from Pichia pastoris: efficient production and immunological properties," Vir. Genes, 2010: 40:53-59.
Berthet et al. GenBank: AHF49783.1; 2015.
Enfissi et al. GenBank: ALX35659.1, 2016.
Pushko, et al., Replicon-Helper Systems from Attenuated Venezuelan Encephalitis Virus: Expression of Heterologous Genes in Vitro and Immunization against Heterologous Pathogens in Vivo, Virology 239, 1997 (pp. 389-401).
Manjila, et al., "Novel gene delivery systems", International Journal of Pharmaceutical Investigation, vol. 3, Issue 1, Jan. 2013 (7 pages).

(56) References Cited

OTHER PUBLICATIONS

International Search Report and Written Opinion, dated Mar. 26, 2019, issued by the International Searching Authority in PCT/JP2018/046794.
Jose et al. "A Structural and functions perspective of alphavirus replication and assembly" Future Microbiol, 2009, vol. 4, No. 7, pp. 837-856.
Garmashova et al., "Analysis of Venezuelan Equine Encephalitis Virus Capsid Protein Function in the Inhibition of Cellular Transcription", Journal of Virology, Dec. 2007, pp. 13552-13565.
Taylor et al. "Mutation of the N-Terminal Region of Chikungunya Virus Capsid Protein: Implications for Vaccine Design", Feb. 21, 2017, vol. 8(1), pp. e01970-16.
Non-Final Office Action issued Oct. 2, 2019 in U.S. Appl. No. 16/225,181.
Final Office Action issued Apr. 29, 2020 in U.S. Appl. No. 16/225,181.
Advisory Action issued Sep. 9, 2020 in U.S. Appl. No. 16/225,181.
Non-Final Office Action issued Oct. 16, 2020 in U.S. Appl. No. 16/225,181.
Final Office Action issued Mar. 22, 2021 in U.S. Appl. No. 16/225,181.
Du, et al., "Identification of a Receptor-Binding Domain in the S Protein of the Novel Human Coronavirus Middle East Respiratory Syndrome Coronavirus as an Essential Target for Vaccine Development", Journal of Virology, vol. 87, No. 17, Sep. 2013, p. 9939-9942 (4 pages).
Zhu, et al. "Receptor-binding domain as a target for developing SARS vaccines", Journal of Thoracic Disease, vol. 5, Suppl. 2, Aug. 2013, pp. S142-S148 (7 pages).
Tai, et al., "Characterization of the receptor-binding domain (RBD) of 2019 novel coronavirus: implication for development of RBD protein as a viral attachment inhibitor and vaccine", Cellular & Molecular Immunology, vol. 17, pp. 613-620, Springer Nature, Mar. 2020 (8 pages).
Yuan Yuan, et al., "Cryo-EM structures of MERS-CoV and SARS-CoV spike glycoproteins reveal the dynamic receptor binding domains", Nature Communications, 2017, vol. 8, No. 15092, pp. 1-9 (9 pages total).

\* cited by examiner

Group1 VRep ssRBD (10^7 IU/dose)

- G1 Day14
- G1 Day35

OD 450nm vs log(serum dilution)

Group2 VRep sshIL2 RBD HA (10^7 IU/dose)

- G2 Day14
- G2 Day35

OD 450nm vs log(serum dilution)

SEQUENCE LISTING

```
<160> NUMBER OF SEQ ID NOS: 51

<210> SEQ ID NO 1
<211> LENGTH: 272
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19-RBD and HA

<400> SEQUENCE: 1

Met Tyr Arg Met Gln Leu Leu Ser Cys Ile Ala Leu Ser Leu Ala Leu
1               5                   10                  15

Val Thr Asn Ser Val Arg Phe Pro Asn Ile Thr Asn Leu Cys Pro Phe
            20                  25                  30

Gly Glu Val Phe Asn Ala Thr Arg Phe Ala Ser Val Tyr Ala Trp Asn
        35                  40                  45

Arg Lys Arg Ile Ser Asn Cys Val Ala Asp Tyr Ser Val Leu Tyr Asn
    50                  55                  60

Ser Ala Ser Phe Ser Thr Phe Lys Cys Tyr Gly Val Ser Pro Thr Lys
65                  70                  75                  80

Leu Asn Asp Leu Cys Phe Thr Asn Val Tyr Ala Asp Ser Phe Val Ile
                85                  90                  95

Arg Gly Asp Glu Val Arg Gln Ile Ala Pro Gly Gln Thr Gly Lys Ile
            100                 105                 110

Ala Asp Tyr Asn Tyr Lys Leu Pro Asp Asp Phe Thr Gly Cys Val Ile
        115                 120                 125

Ala Trp Asn Ser Asn Asn Leu Asp Ser Lys Val Gly Gly Asn Tyr Asn
    130                 135                 140
```

```
Tyr Leu Tyr Arg Leu Phe Arg Lys Ser Asn Leu Lys Pro Phe Glu Arg
145                 150                 155                 160

Asp Ile Ser Thr Glu Ile Tyr Gln Ala Gly Ser Thr Pro Cys Asn Gly
                165                 170                 175

Val Glu Gly Phe Asn Cys Tyr Phe Pro Leu Gln Ser Tyr Gly Phe Gln
            180                 185                 190

Pro Thr Asn Gly Val Gly Tyr Gln Pro Tyr Arg Val Val Val Leu Ser
        195                 200                 205

Phe Glu Leu Leu His Ala Pro Ala Thr Val Cys Gly Pro Lys Lys Ser
    210                 215                 220

Gly Val Lys Leu Glu Ser Met Gly Ile Tyr Gln Ile Leu Ala Ile Tyr
225                 230                 235                 240

Ser Thr Val Ala Ser Ser Leu Val Leu Leu Val Ser Leu Gly Ala Ile
                245                 250                 255

Ser Phe Trp Met Cys Ser Asn Gly Ser Leu Gln Cys Arg Ile Cys Ile
            260                 265                 270

<210> SEQ ID NO 2
<211> LENGTH: 20
<212> TYPE: PRT
<213> ORGANISM: Artificial Sequence
<220> FEATURE:
<223> OTHER INFORMATION: Synthetic sequence, human IL-2 signal sequence

<400> SEQUENCE: 2

Met Tyr Arg Met Gln Leu Leu Ser Cys Ile Ala Leu Ser Leu Ala Leu
1               5                   10                  15

Val Thr Asn Ser
            20

<210> SEQ ID NO 3
<211> LENGTH: 204
<212> TYPE: PRT
<213> ORGANISM: Artificial Sequence
<220> FEATURE:
<223> OTHER INFORMATION: Synthetic sequence, COVID19-RBD

<400> SEQUENCE: 3

Val Arg Phe Pro Asn Ile Thr Asn Leu Cys Pro Phe Gly Glu Val Phe
1               5                   10                  15

Asn Ala Thr Arg Phe Ala Ser Val Tyr Ala Trp Asn Arg Lys Arg Ile
            20                  25                  30

Ser Asn Cys Val Ala Asp Tyr Ser Val Leu Tyr Asn Ser Ala Ser Phe
        35                  40                  45

Ser Thr Phe Lys Cys Tyr Gly Val Ser Pro Thr Lys Leu Asn Asp Leu
    50                  55                  60

Cys Phe Thr Asn Val Tyr Ala Asp Ser Phe Val Ile Arg Gly Asp Glu
65                  70                  75                  80

Val Arg Gln Ile Ala Pro Gly Gln Thr Gly Lys Ile Ala Asp Tyr Asn
                85                  90                  95

Tyr Lys Leu Pro Asp Asp Phe Thr Gly Cys Val Ile Ala Trp Asn Ser
            100                 105                 110

Asn Asn Leu Asp Ser Lys Val Gly Gly Asn Tyr Asn Tyr Leu Tyr Arg
        115                 120                 125

Leu Phe Arg Lys Ser Asn Leu Lys Pro Phe Glu Arg Asp Ile Ser Thr
    130                 135                 140

Glu Ile Tyr Gln Ala Gly Ser Thr Pro Cys Asn Gly Val Glu Gly Phe
```

```
                145                 150                 155                 160
Asn Cys Tyr Phe Pro Leu Gln Ser Tyr Gly Phe Gln Pro Thr Asn Gly
                    165                 170                 175

Val Gly Tyr Gln Pro Tyr Arg Val Val Val Leu Ser Phe Glu Leu Leu
                180                 185                 190

His Ala Pro Ala Thr Val Cys Gly Pro Lys Lys Ser
                195                 200

<210> SEQ ID NO 4
<211> LENGTH: 48
<212> TYPE: PRT
<213> ORGANISM: Artificial Sequence
<220> FEATURE:
<223> OTHER INFORMATION: Synthetic sequence, influenza HA (flexible-TM-
      Cyt)

<400> SEQUENCE: 4

Gly Val Lys Leu Glu Ser Met Gly Ile Tyr Gln Ile Leu Ala Ile Tyr
1               5                   10                  15

Ser Thr Val Ala Ser Ser Leu Val Leu Val Ser Leu Gly Ala Ile
                20                  25                  30

Ser Phe Trp Met Cys Ser Asn Gly Ser Leu Gln Cys Arg Ile Cys Ile
                35                  40                  45

<210> SEQ ID NO 5
<211> LENGTH: 274
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19-RBD and HA(flexible-TM-Cyt).

<400> SEQUENCE: 5

Met Tyr Arg Met Gln Leu Leu Ser Cys Ile Ala Leu Ser Leu Ala Leu
1               5                   10                  15

Val Thr Asn Ser Cys Val Arg Phe Pro Asn Ile Thr Asn Leu Cys Pro
                20                  25                  30

Phe Gly Glu Val Phe Asn Ala Thr Arg Phe Ala Ser Val Tyr Ala Trp
                35                  40                  45

Asn Arg Lys Arg Ile Ser Asn Cys Val Ala Asp Tyr Ser Val Leu Tyr
    50                  55                  60

Asn Ser Ala Ser Phe Ser Thr Phe Lys Cys Tyr Gly Val Ser Pro Thr
65                  70                  75                  80

Lys Leu Asn Asp Leu Cys Phe Thr Asn Val Tyr Ala Asp Ser Phe Val
                85                  90                  95

Ile Arg Gly Asp Glu Val Arg Gln Ile Ala Pro Gly Gln Thr Gly Lys
                100                 105                 110

Ile Ala Asp Tyr Asn Tyr Lys Leu Pro Asp Asp Phe Thr Gly Cys Val
                115                 120                 125

Ile Ala Trp Asn Ser Asn Asn Leu Asp Ser Lys Val Gly Gly Asn Tyr
            130                 135                 140

Asn Tyr Leu Tyr Arg Leu Phe Arg Lys Ser Asn Leu Lys Pro Phe Glu
145                 150                 155                 160

Arg Asp Ile Ser Thr Glu Ile Tyr Gln Ala Gly Ser Thr Pro Cys Asn
                165                 170                 175

Gly Val Glu Gly Phe Asn Cys Tyr Phe Pro Leu Gln Ser Tyr Gly Phe
                180                 185                 190

Gln Pro Thr Asn Gly Val Gly Tyr Gln Pro Tyr Arg Val Val Val Leu
```

```
                195                 200                 205
Ser Phe Glu Leu Leu His Ala Pro Ala Thr Val Cys Gly Pro Lys Lys
    210                 215                 220

Ser Cys Gly Val Lys Leu Glu Ser Met Gly Ile Tyr Gln Ile Leu Ala
225                 230                 235                 240

Ile Tyr Ser Thr Val Ala Ser Ser Leu Val Leu Leu Val Ser Leu Gly
                245                 250                 255

Ala Ile Ser Phe Trp Met Cys Ser Asn Gly Ser Leu Gln Cys Arg Ile
            260                 265                 270

Cys Ile
```

<210> SEQ ID NO 6
<211> LENGTH: 383
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19-RBD, human IgG4CH3 and
      HA(flexible-TM-Cyt)

<400> SEQUENCE: 6

```
Met Tyr Arg Met Gln Leu Leu Ser Cys Ile Ala Leu Ser Leu Ala Leu
1               5                   10                  15

Val Thr Asn Ser Val Arg Phe Pro Asn Ile Thr Asn Leu Cys Pro Phe
            20                  25                  30

Gly Glu Val Phe Asn Ala Thr Arg Phe Ala Ser Val Tyr Ala Trp Asn
        35                  40                  45

Arg Lys Arg Ile Ser Asn Cys Val Ala Asp Tyr Ser Val Leu Tyr Asn
    50                  55                  60

Ser Ala Ser Phe Ser Thr Phe Lys Cys Tyr Gly Val Ser Pro Thr Lys
65                  70                  75                  80

Leu Asn Asp Leu Cys Phe Thr Asn Val Tyr Ala Asp Ser Phe Val Ile
                85                  90                  95

Arg Gly Asp Glu Val Arg Gln Ile Ala Pro Gly Gln Thr Gly Lys Ile
            100                 105                 110

Ala Asp Tyr Asn Tyr Lys Leu Pro Asp Asp Phe Thr Gly Cys Val Ile
        115                 120                 125

Ala Trp Asn Ser Asn Asn Leu Asp Ser Lys Val Gly Gly Asn Tyr Asn
    130                 135                 140

Tyr Leu Tyr Arg Leu Phe Arg Lys Ser Asn Leu Lys Pro Phe Glu Arg
145                 150                 155                 160

Asp Ile Ser Thr Glu Ile Tyr Gln Ala Gly Ser Thr Pro Cys Asn Gly
                165                 170                 175

Val Glu Gly Phe Asn Cys Tyr Phe Pro Leu Gln Ser Tyr Gly Phe Gln
            180                 185                 190

Pro Thr Asn Gly Val Gly Tyr Gln Pro Tyr Arg Val Val Val Leu Ser
        195                 200                 205

Phe Glu Leu Leu His Ala Pro Ala Thr Val Cys Gly Pro Lys Lys Ser
    210                 215                 220

Gly Ser Gly Gln Pro Arg Glu Pro Gln Val Tyr Thr Leu Pro Pro Ser
225                 230                 235                 240

Gln Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270
```

```
Pro Glu Asn Asn Tyr Lys Thr Thr Pro Pro Val Leu Asp Ser Asp Gly
            275                 280                 285

Ser Phe Phe Leu Tyr Ser Arg Leu Thr Val Asp Lys Ser Arg Trp Gln
    290                 295                 300

Glu Gly Asn Val Phe Ser Cys Ser Val Met His Glu Ala Leu His Asn
305                 310                 315                 320

His Tyr Thr Gln Lys Ser Leu Ser Leu Ser Leu Gly Lys Gly Ser Gly
                325                 330                 335

Val Lys Leu Glu Ser Met Gly Ile Tyr Gln Ile Leu Ala Ile Tyr Ser
                340                 345                 350

Thr Val Ala Ser Ser Leu Val Leu Leu Val Ser Leu Gly Ala Ile Ser
            355                 360                 365

Phe Trp Met Cys Ser Asn Gly Ser Leu Gln Cys Arg Ile Cys Ile
        370                 375                 380

<210> SEQ ID NO 7
<211> LENGTH: 107
<212> TYPE: PRT
<213> ORGANISM: Artificial Sequence
<220> FEATURE:
<223> OTHER INFORMATION: Synthetic sequence, human IgG4 CH3 (linker)

<400> SEQUENCE: 7

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 8
<211> LENGTH: 385
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19-RBD, human IgG4CH3 and HA
      (flexible-TM-Cyt)

<400> S

```
Lys Leu Asn Asp Leu Cys Phe Thr Asn Val Tyr Ala Asp Ser Phe Val
                 85                  90                  95

Ile Arg Gly Asp Glu Val Arg Gln Ile Ala Pro Gly Gln Thr Gly Lys
            100                 105                 110

Ile Ala Asp Tyr Asn Tyr Lys Leu Pro Asp Asp Phe Thr Gly Cys Val
            115                 120                 125

Ile Ala Trp Asn Ser Asn Asn Leu Asp Ser Lys Val Gly Gly Asn Tyr
130                 135                 140

Asn Tyr Leu Tyr Arg Leu Phe Arg Lys Ser Asn Leu Lys Pro Phe Glu
145                 150                 155                 160

Arg Asp Ile Ser Thr Glu Ile Tyr Gln Ala Gly Ser Thr Pro Cys Asn
                165                 170                 175

Gly Val Glu Gly Phe Asn Cys Tyr Phe Pro Leu Gln Ser Tyr Gly Phe
            180                 185                 190

Gln Pro Thr Asn Gly Val Gly Tyr Gln Pro Tyr Arg Val Val Val Leu
            195                 200                 205

Ser Phe Glu Leu Leu His Ala Pro Ala Thr Val Cys Gly Pro Lys Lys
            210                 215                 220

Ser Cys Gly Ser Gly Gln Pro Arg Glu Pro Gln Val Tyr Thr Leu Pro
225                 230                 235                 240

Pro Ser Gln Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Arg Leu Thr Val Asp Lys Ser Arg
290                 295                 300

Trp Gln Glu Gly Asn Val Phe Ser Cys Ser Val Met His Glu Ala Leu
305                 310                 315                 320

His Asn His Tyr Thr Gln Lys Ser Leu Ser Leu Ser Leu Gly Lys Gly
                325                 330                 335

Ser Gly Val Lys Leu Glu Ser Met Gly Ile Tyr Gln Ile Leu Ala Ile
            340                 345                 350

Tyr Ser Thr Val Ala Ser Ser Leu Val Leu Leu Val Ser Leu Gly Ala
            355                 360                 365

Ile Ser Phe Trp Met Cys Ser Asn Gly Ser Leu Gln Cys Arg Ile Cys
            370                 375                 380

Ile
385

<210> SEQ ID NO 9
<211> LENGTH: 435
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19-RBD, and human TLR4(TM-TIR)

<400> SEQUENCE: 9

Met Tyr Arg Met G

Arg Lys Arg Ile Ser Asn Cys Val Ala Asp Tyr Ser Val Leu Tyr Asn
    50                  55                  60
Ser Ala Ser Phe Ser Thr Phe Lys Cys Tyr Gly Val Ser Pro Thr Lys
65                  70                  75                  80
Leu Asn Asp Leu Cys Phe Thr Asn Val Tyr Ala Asp Ser Phe Val Ile
                85                  90                  95
Arg Gly Asp Glu Val Arg Gln Ile Ala Pro Gly Gln Thr Gly Lys Ile
            100                 105                 110
Ala Asp Tyr Asn Tyr Lys Leu Pro Asp Asp Phe Thr Gly Cys Val Ile
        115                 120                 125
Ala Trp Asn Ser Asn Asn Leu Asp Ser Lys Val Gly Gly Asn Tyr Asn
    130                 135                 140
Tyr Leu Tyr Arg Leu Phe Arg Lys Ser Asn Leu Lys Pro Phe Glu Arg
145                 150                 155                 160
Asp Ile Ser Thr Glu Ile Tyr Gln Ala Gly Ser Thr Pro Cys Asn Gly
                165                 170                 175
Val Glu Gly Phe Asn Cys Tyr Phe Pro Leu Gln Ser Tyr Gly Phe Gln
            180                 185                 190
Pro Thr Asn Gly Val Gly Tyr Gln Pro Tyr Arg Val Val Val Leu Ser
        195                 200                 205
Phe Glu Leu Leu His Ala Pro Ala Thr Val Cys Gly Pro Lys Lys Ser
210                 215                 220
Gly Ser Lys Thr Ile Ile Gly Val Ser Val Leu Ser Val Leu Val Val
225                 230                 235                 240
Ser Val Val Ala Val Leu Val Tyr Lys Phe Tyr Phe His Leu Met Leu
                245                 250                 255
Leu Ala Gly Cys Ile Lys Tyr Gly Arg Gly Glu Asn Ile Tyr Asp Ala
            260                 265                 270
Phe Val Ile Tyr Ser Ser Gln Asp Glu Asp Trp Val Arg Asn Glu Leu
        275                 280                 285
Val Lys Asn Leu Glu Glu Gly Val Pro Pro Phe Gln Leu Cys Leu His
    290                 295                 300
Tyr Arg Asp Phe Ile Pro Gly Val Ala Ile Ala Ala Asn Ile Ile His
305                 310                 315                 320
Glu Gly Phe His Lys Ser Arg Lys Val Ile Val Val Ser Gln His
                325                 330                 335
Phe Ile Gln Ser Arg Trp Cys Ile Phe Glu Tyr Glu Ile Ala Gln Thr
            340                 345                 350
Trp Gln Phe Leu Ser Ser Arg Ala Gly Ile Ile Phe Ile Val Leu Gln
        355                 360                 365
Lys Val Glu Lys Thr Leu Leu Arg Gln Gln Val Glu Leu Tyr Arg Leu
    370                 375                 380
Leu Ser Arg Asn Thr Tyr Leu Glu Trp Glu Asp Ser Val Leu Gly Arg
385                 390                 395                 400
His Ile Phe Trp Arg Arg Leu Arg Lys Ala Leu Leu Asp Gly Lys Ser
                405                 410                 415
Trp Asn Pro Glu Gly Thr Val Gly Thr Gly Cys Asn Trp Gln Glu Ala
            420                 425                 430
Thr Ser Ile
        435

<210> SEQ ID NO 10
<211> LENGTH: 209

```
<212> TYPE: PRT
<213> ORGANISM: Artificial Sequence
<220> FEATURE:
<223> OTHER INFORMATION: Synthetic sequence, human TLR4
      (TM-Toll/interleukin-1 receptor domain)

<400> SEQUENCE: 10

Lys Thr Ile Ile Gly Val Ser Val Leu Val Val Ser Val
1               5                   10                  15

Val Ala Val Leu Val Tyr Lys Phe Tyr Phe His Leu Met Leu Leu Ala
            20                  25                  30

Gly Cys Ile Lys Tyr Gly Arg Gly Glu Asn Ile Tyr Asp Ala Phe Val
            35                  40                  45

Ile Tyr Ser Ser Gln Asp Glu Asp Trp Val Arg Asn Glu Leu Val Lys
50                  55                  60

Asn Leu Glu Glu Gly Val Pro Pro Phe Gln Leu Cys Leu His Tyr Arg
65                  70                  75                  80

Asp Phe Ile Pro Gly Val Ala Ile Ala Ala Asn Ile Ile His Glu Gly
                85                  90                  95

Phe His Lys Ser Arg Lys Val Ile Val Val Ser Gln His Phe Ile
            100                 105                 110

Gln Ser Arg Trp Cys Ile Phe Glu Tyr Glu Ile Ala Gln Thr Trp Gln
            115                 120                 125

Phe Leu Ser Ser Arg Ala Gly Ile Ile Phe Ile Val Leu Gln Lys Val
            130                 135                 140

Glu Lys Thr Leu Leu Arg Gln Gln Val Glu Leu Tyr Arg Leu Leu Ser
145                 150                 155                 160

Arg Asn Thr Tyr Leu Glu Trp Glu Asp Ser Val Leu Gly Arg His Ile
                165                 170                 175

Phe Trp Arg Arg Leu Arg Lys Ala Leu Leu Asp Gly Lys Ser Trp Asn
            180                 185                 190

Pro Glu Gly Thr Val Gly Thr Gly Cys Asn Trp Gln Glu Ala Thr Ser
            195                 200                 205

Ile

<210> SEQ ID NO 11
<211> LENGTH: 437
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19-RBD and human TLR4 (TM-TIR)

<400> SEQUENCE: 11

Met Tyr Arg Met Gln Leu Leu Ser Cys Ile Ala Leu Ser Leu Ala Leu
1               5                   10                  15

Val Thr Asn Ser Cys Val Arg Phe Pro Asn Ile Thr Asn Leu Cys Pro
            20                  25                  30

Phe Gly Glu Val Phe Asn Ala Thr Arg Phe Ala Ser Val Tyr Ala Trp
            35                  40                  45

Asn Arg Lys Arg Ile Ser Asn Cys Val Ala Asp Tyr Ser Val Leu Tyr
50                  55                  60

Asn Ser Ala Ser Phe Ser Thr Phe Lys Cys Tyr Gly Val Ser Pro Thr
65                  70                  75                  80

Lys Leu Asn Asp Leu Cys Phe Thr Asn Val Tyr Ala Asp Ser Phe Val
                85                  90                  95

Ile Arg Gly Asp Glu Val Arg Gln Ile Ala Pro Gly Gln Thr Gly Lys
```

```
                    100                 105                 110
Ile Ala Asp Tyr Asn Tyr Lys Leu Pro Asp Asp Phe Thr Gly Cys Val
            115                 120                 125

Ile Ala Trp Asn Ser Asn Leu Asp Ser Lys Val Gly Gly Asn Tyr
            130                 135             140

Asn Tyr Leu Tyr Arg Leu Phe Arg Lys Ser Asn Leu Lys Pro Phe Glu
145                 150                 155                 160

Arg Asp Ile Ser Thr Glu Ile Tyr Gln Ala Gly Ser Thr Pro Cys Asn
                165                 170                 175

Gly Val Glu Gly Phe Asn Cys Tyr Phe Pro Leu Gln Ser Tyr Gly Phe
                180                 185                 190

Gln Pro Thr Asn Gly Val Gly Tyr Gln Pro Tyr Arg Val Val Val Leu
            195                 200                 205

Ser Phe Glu Leu Leu His Ala Pro Ala Thr Val Cys Gly Pro Lys Lys
    210                 215                 220

Ser Cys Gly Ser Lys Thr Ile Ile Gly Val Ser Val Leu Ser Val Leu
225                 230                 235                 240

Val Val Ser Val Val Ala Val Leu Val Tyr Lys Phe Tyr Phe His Leu
                245                 250                 255

Met Leu Leu Ala Gly Cys Ile Lys Tyr Gly Arg Gly Glu Asn Ile Tyr
                260                 265                 270

Asp Ala Phe Val Ile Tyr Ser Ser Gln Asp Glu Asp Trp Val Arg Asn
            275                 280                 285

Glu Leu Val Lys Asn Leu Glu Glu Gly Val Pro Pro Phe Gln Leu Cys
    290                 295                 300

Leu His Tyr Arg Asp Phe Ile Pro Gly Val Ala Ile Ala Ala Asn Ile
305                 310                 315                 320

Ile His Glu Gly Phe His Lys Ser Arg Lys Val Ile Val Val Val Ser
                325                 330                 335

Gln His Phe Ile Gln Ser Arg Trp Cys Ile Phe Glu Tyr Glu Ile Ala
            340                 345                 350

Gln Thr Trp Gln Phe Leu Ser Ser Arg Ala Gly Ile Ile Phe Ile Val
            355                 360                 365

Leu Gln Lys Val Glu Lys Thr Leu Leu Arg Gln Gln Val Glu Leu Tyr
    370                 375                 380

Arg Leu Leu Ser Arg Asn Thr Tyr Leu Glu Trp Glu Asp Ser Val Leu
385                 390                 395                 400

Gly Arg His Ile Phe Trp Arg Arg Leu Arg Lys Ala Leu Leu Asp Gly
                405                 410                 415

Lys Ser Trp Asn Pro Glu Gly Thr Val Gly Thr Gly Cys Asn Trp Gln
            420                 425                 430

Glu Ala Thr Ser Ile
            435

<210> SEQ ID NO 12
<211> LENGTH: 544
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19-RBD, human IgG4CH3, and Human

```
Val Thr Asn Ser Val Arg Phe Pro Asn Ile Thr Asn Leu Cys Pro Phe
             20                  25                  30

Gly Glu Val Phe Asn Ala Thr Arg Phe Ala Ser Val Tyr Ala Trp Asn
             35                  40                  45

Arg Lys Arg Ile Ser Asn Cys Val Ala Asp Tyr Ser Val Leu Tyr Asn
 50                  55                  60

Ser Ala Ser Phe Ser Thr Phe Lys Cys Tyr Gly Val Ser Pro Thr Lys
 65                  70                  75                  80

Leu Asn Asp Leu Cys Phe Thr Asn Val Tyr Ala Asp Ser Phe Val Ile
                 85                  90                  95

Arg Gly Asp Glu Val Arg Gln Ile Ala Pro Gly Gln Thr Gly Lys Ile
                100                 105                 110

Ala Asp Tyr Asn Tyr Lys Leu Pro Asp Asp Phe Thr Gly Cys Val Ile
            115                 120                 125

Ala Trp Asn Ser Asn Asn Leu Asp Ser Lys Val Gly Gly Asn Tyr Asn
    130                 135                 140

Tyr Leu Tyr Arg Leu Phe Arg Lys Ser Asn Leu Lys Pro Phe Glu Arg
145                 150                 155                 160

Asp Ile Ser Thr Glu Ile Tyr Gln Ala Gly Ser Thr Pro Cys Asn Gly
                165                 170                 175

Val Glu Gly Phe Asn Cys Tyr Phe Pro Leu Gln Ser Tyr Gly Phe Gln
            180                 185                 190

Pro Thr Asn Gly Val Gly Tyr Gln Pro Tyr Arg Val Val Val Leu Ser
        195                 200                 205

Phe Glu Leu Leu His Ala Pro Ala Thr Val Cys Gly Pro Lys Lys Ser
    210                 215                 220

Gly Ser Gly Gln Pro Arg Glu Pro Gln Val Tyr Thr Leu Pro Pro Ser
225                 230                 235                 240

Gln Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Arg Leu Thr Val Asp Lys Ser Arg Trp Gln
    290                 295                 300

Glu Gly Asn Val Phe Ser Cys Ser Val Met His Glu Ala Leu His Asn
305                 310                 315                 320

His Tyr Thr Gln Lys Ser Leu Ser Leu Ser Leu Gly Lys Gly Ser Lys
                325                 330                 335

Thr Ile Ile Gly Val Ser Val Leu Ser Val Leu Val Ser Val Val
            340                 345                 350

Ala Val Leu Val Tyr Lys Phe Tyr Phe His Leu Met Leu Leu Ala Gly
        355                 360                 365

Cys Ile Lys Tyr Gly Arg Gly Glu Asn Ile Tyr Asp Ala Phe Val Ile
    370                 375                 380

Tyr Ser Ser Gln Asp Glu Asp Trp Val Arg Asn Glu Leu Val Lys Asn
385                 390                 395                 400

Leu Glu Glu Gly Val Pro Pro Phe Gln Leu Cys Leu His Tyr Arg Asp
                405                 410                 415

Phe Ile Pro Gly Val Ala Ile Ala Ala Asn Ile Ile His Glu Gly Phe
            420                 425                 430
```

```
His Lys Ser Arg Lys Val Ile Val Val Ser Gln His Phe Ile Gln
            435                 440                 445

Ser Arg Trp Cys Ile Phe Glu Tyr Glu Ile Ala Gln Thr Trp Gln Phe
450                 455                 460

Leu Ser Ser Arg Ala Gly Ile Ile Phe Ile Val Leu Gln Lys Val Glu
465                 470                 475                 480

Lys Thr Leu Leu Arg Gln Gln Val Glu Leu Tyr Arg Leu Leu Ser Arg
                485                 490                 495

Asn Thr Tyr Leu Glu Trp Glu Asp Ser Val Leu Gly Arg His Ile Phe
            500                 505                 510

Trp Arg Arg Leu Arg Lys Ala Leu Leu Asp Gly Lys Ser Trp Asn Pro
        515                 520                 525

Glu Gly Thr Val Gly Thr Gly Cys Asn Trp Gln Glu Ala Thr Ser Ile
    530                 535                 540

<210> SEQ ID NO 13
<211> LENGTH: 546
<212> TYPE: PRT
<213> ORGANISM: Artificial Sequence
<220> FEATURE:
<223> OTHER INFORMATION: Synthetic sequence, fused protein comprising
      hIL-2 signal sequence, COVID19-RBD, human IgG4CH3, and Human
      TLR4(TM-TIR)

<400> SEQUENCE: 13

Met Tyr Arg Met Gln Leu Leu Ser Cys Ile Ala Leu Ser Leu Ala

```
                        245                 250                 255
Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Arg Leu Thr Val Asp Lys Ser Arg
        290                 295                 300

Trp Gln Glu Gly Asn Val Phe Ser Cys Ser Val Met His Glu Ala Leu
305                 310                 315                 320

His Asn His Tyr Thr Gln Lys Ser Leu Ser Leu Ser Leu Gly Lys Gly
                325                 330                 335

Ser Lys Thr Ile Ile Gly Val Ser Val Leu Ser Val Leu Val Val Ser
            340                 345                 350

Val Val Ala Val Leu Val Tyr Lys Phe Tyr Phe His Leu Met Leu Leu
        355                 360                 365

Ala Gly Cys Ile Lys Tyr Gly Arg Gly Glu Asn Ile Tyr Asp Ala Phe
    370                 375                 380

Val Ile Tyr Ser Ser Gln Asp Glu Asp Trp Val Arg Asn Glu Leu Val
385                 390                 395                 400

Lys Asn Leu Glu Glu Gly Val Pro Pro Phe Gln Leu Cys Leu His Tyr
                405                 410                 415

Arg Asp Phe Ile Pro Gly Val Ala Ile Ala Ala Asn Ile Ile His Glu
            420                 425                 430

Gly Phe His Lys Ser Arg Lys Val Ile Val Val Val Ser Gln His Phe
        435                 440                 445

Ile Gln Ser Arg Trp Cys Ile Phe Glu Tyr Glu Ile Ala Gln Thr Trp
    450                 455                 460

Gln Phe Leu Ser Ser Arg Ala Gly Ile Ile Phe Ile Val Leu Gln Lys
465                 470                 475                 480

Val Glu Lys Thr Leu Leu Arg Gln Gln Val Glu Leu Tyr Arg Leu Leu
                485                 490                 495

Ser Arg Asn Thr Tyr Leu Glu Trp Glu Asp Ser Val Leu Gly Arg His
            500                 505                 510

Ile Phe Trp Arg Arg Leu Arg Lys Ala Leu Leu Asp Gly Lys Ser Trp
        515                 520                 525

Asn Pro Glu Gly Thr Val Gly Thr Gly Cys Asn Trp Gln Glu Ala Thr
    530                 535                 540

Ser Ile
545

<210> SEQ ID NO 14
<211> LENGTH: 15
<212> TYPE: PRT
<213> ORGANISM: Artificial Sequence
<220> FEATURE:
<223> OTHER INFORMATION: Synthetic sequence, COVID-19 signal sequence
      (1-15)

<400> SEQUENCE: 14

Met Phe Val Phe Leu Val Leu Leu Pro Leu Val Ser Ser Gln Cys
1               5                   10                  15

<210> SEQ ID NO 15
<211> LENGTH: 20
<212> TYPE: PRT
<213> ORGANISM: Artificial Sequence
<220> FEATURE:
```

<223> OTHER INFORMATION: Synthetic sequence, human IL-2 signal sequence

<400> SEQUENCE: 15

Met Tyr Arg Met Gln Leu Leu Ser Cys Ile Ala Leu Ser Leu Ala Leu
1               5                   10                  15

Val Thr Asn Ser
            20

<210> SEQ ID NO 16
<211> LENGTH: 13
<212> TYPE: PRT
<213> ORGANISM: Artificial Sequence
<220> FEATURE:
<223> OTHER INFORMATION: Synthetic sequence, COVID-19 signal sequence
      (1-13)

<400> SEQUENCE: 16

Met Phe Val Phe Leu Val Leu Leu Pro Leu Val Ser Ser
1               5                   10

<210> SEQ ID NO 17
<211> LENGTH: 192
<212> TYPE: PRT
<213> ORGANISM: Artificial Sequence
<220> FEATURE:
<223> OTHER INFORMATION: Synthetic sequence, COVID-19 RBD (AA 330-521)

<400> SEQUENCE: 17

Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
    130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
            180                 185                 190

<210> SEQ ID NO 18
<211> LENGTH: 201
<212> TYPE: PRT
<213> ORGANISM: Artificial Sequence
<220> FEATURE:
<223> OTHER INFORMATION: Synthetic sequence, COVID-19 RBD (AA 330-530)

<400> SEQUENCE: 18

```
Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
            35                  40                  45

Lys Cys Tyr Gly Val Ser Pro Thr Lys Leu Asn Asp Leu Cys Phe Thr
        50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
                100                 105                 110

Asp Ser Lys Val Gly Gly Asn Tyr Asn Tyr Leu Tyr Arg Leu Phe Arg
            115                 120                 125

Lys Ser Asn Leu Lys Pro Phe Glu Arg Asp Ile Ser Thr Glu Ile Tyr
        130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
                180                 185                 190

Ala Thr Val Cys Gly Pro Lys Lys Ser
            195                 200
```

<210> SEQ ID NO 19
<211> LENGTH: 205
<212> TYPE: PRT
<213> ORGANISM: Artificial Sequence
<220> FEATURE:
<223> OTHER INFORMATION: Synthetic sequence, COVID-19 RBD (AA 327-531)

<400> SEQUENCE: 19

```
Val Arg Phe Pro Asn Ile Thr Asn Leu Cys Pro Phe Gly Glu Val Phe
1               5                   10                  15

Asn Ala Thr Arg Phe Ala Ser Val Tyr Ala Trp Asn Arg Lys Arg Ile
            20                  25                  30

Ser Asn Cys Val Ala Asp Tyr Ser Val Leu Tyr Asn Ser Ala Ser Phe
        35                  40                  45

Ser Thr Phe Lys Cys Tyr Gly Val Ser Pro Thr Lys Leu Asn Asp Leu
    50                  55                  60

Cys Phe Thr Asn Val Tyr Ala Asp Ser Phe Val Ile Arg Gly Asp Glu
65                  70                  75                  80

Val Arg Gln Ile Ala Pro Gly Gln Thr Gly Lys Ile Ala Asp Tyr Asn
                85                  90                  95

Tyr Lys Leu Pro Asp Asp Phe Thr Gly Cys Val Ile Ala Trp Asn Ser
                100                 105                 110

Asn Asn Leu Asp Ser Lys Val Gly Gly Asn Tyr Asn Tyr Leu Tyr Arg
            115                 120                 125

Leu Phe Arg Lys Ser Asn Leu Lys Pro Phe Glu Arg Asp Ile Ser Thr
        130                 135                 140

Glu Ile Tyr Gln Ala Gly Ser Thr Pro Cys Asn Gly Val Glu Gly Phe
145                 150                 155                 160
```

-continued

```
Asn Cys Tyr Phe Pro Leu Gln Ser Tyr Gly Phe Gln Pro Thr Asn Gly
            165                 170                 175

Val Gly Tyr Gln Pro Tyr Arg Val Val Leu Ser Phe Glu Leu Leu
        180                 185                 190

His Ala Pro Ala Thr Val Cys Gly Pro Lys Lys Ser Thr
        195                 200                 205

<210> SEQ ID NO 20
<211> LENGTH: 107
<212> TYPE: PRT
<213> ORGANISM: Artificial Sequence
<220> FEATURE:
<223> OTHER INFORMATION: Synthetic sequence, human IgG4-CH3 (Linker)

<400> SEQUENCE: 20

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 21
<211> LENGTH: 46
<212> TYPE: PRT
<213> ORGANISM: Artificial Sequence
<220> FEATURE:
<223> OTHER INFORMATION: Synthetic sequence, human CD80 transmembrane-
      cytoplasm

<400> SEQUENCE: 21

Leu Leu Pro Ser Trp Ala Ile Thr Leu Ile Ser Val Asn Gly Ile Phe
1               5                   10                  15

Val Ile Cys Cys Leu Thr Tyr Cys Phe Ala Pro Arg Cys Arg Glu Arg
            20                  25                  30

Arg Arg Asn Glu Arg Leu Arg Arg Glu Ser Val Arg Pro Val
        35                  40                  45

<210> SEQ ID NO 22
<211> LENGTH: 48
<212> TYPE: PRT
<213> ORGANISM: Artificial Sequence
<220> FEATURE:
<223> OTHER INFORMATION: Synthetic sequence, influenza HA (flexible-TM-
      Cyt)

<400> SEQUENCE: 22

Gly Val Lys Leu Glu Ser Met Gly Ile Tyr Gln Ile Leu Ala Ile Tyr
1               5                   10                  15

Ser Thr Val Ala Ser Ser Leu Val Leu Val Ser Leu Gly Ala Ile
            20                  25                  30

Ser Phe Trp Met Cys Ser Asn Gly Ser Leu Gln Cys Arg Ile Cys Ile
```

<210> SEQ ID NO 23
<211> LENGTH: 70
<212> TYPE: PRT
<213> ORGANISM: Artificial Sequence
<220> FEATURE:
<223> OTHER INFORMATION: Synthetic sequence, COVID19 juxtamembrane
      domain and transmembrane domain

<400> SEQUENCE: 23

Gly Lys Tyr Glu Gln Tyr Ile Lys Trp Pro Trp Tyr Ile Trp Leu Gly
1               5                   10                  15

Phe Ile Ala Gly Leu Ile Ala Ile Val Met Val Thr Ile Met Leu Cys
20 25 30

Cys Met Thr Ser Cys Cys Ser Cys Leu Lys Gly Cys Cys Ser Cys Gly
35 40 45

Ser Cys Cys Lys Phe Asp Glu Asp Asp Ser Glu Pro Val Leu Lys Gly
50 55 60

Val Lys Leu His Tyr Thr
65 70

<210> SEQ ID NO 24
<211> LENGTH: 15
<212> TYPE: PRT
<213> ORGANISM: Artificial Sequence
<220> FEATURE:
<223> OTHER INFORMATION: Synthetic sequence, juxtamembrane domain of COVID-19 spike protein

<400> SEQUENCE: 24

Gly Lys Tyr Glu Gln Tyr Ile Lys Trp Pro Trp Tyr Ile Trp Leu
1 5 10 15

<210> SEQ ID NO 25
<211> LENGTH: 55
<212> TYPE: PRT
<213> ORGANISM: Artificial Sequence
<220> FEATURE:
<223> OTHER INFORMATION: Synthetic sequence, transmembrane domain of COVID-19 spike protein

<400> SEQUENCE: 25

Gly Phe Ile Ala Gly Leu Ile Ala Ile Val Met Val Thr Ile Met Leu
1 5 10 15

Cys Cys Met Thr Ser Cys Cys Ser Cys Leu Lys Gly Cys Cys Ser Cys
20 25 30

Gly Ser Cys Cys Lys Phe Asp Glu Asp Asp Ser Glu Pro Val Leu Lys
35 40 45

Gly Val Lys Leu His Tyr Thr
50 55

<210> SEQ ID NO 26
<211> LENGTH: 35
<212> TYPE: DNA
<213> ORGANISM: Artificial Sequence
<220> FEATURE:
<223> OTHER INFORMATION: Synthetic sequence, SG promoter

<400> SEQUENCE: 26
cctgaatgga ctacgacata gtctagtccg ccaag 35

<210> SEQ ID NO 27

```
<211> LENGTH: 44
<212> TYPE: DNA
<213> ORGANISM: Artificial Sequence
<220> FEATURE:
<223> OTHER INFORMATION: Synthetic sequence, 5' UTR

<400> SEQUENCE: 27
ataggcggcg catgagagaa gcccagacca attacctacc caaa                      44

<210> SEQ ID NO 28
<211> LENGTH: 125
<212> TYPE: DNA
<213> ORGANISM: Artificial Sequence
<220> FEATURE:
<223> OTHER INFORMATION: Synthetic sequence, 3' UTR

<400> SEQUENCE: 28
gcgatcgcat acagcagcaa ttggcaagct gcttacatag aactcgcggc gattggcatg     60
ccgccttaaa atttttattt tatttttctt ttcttttccg aatcggattt tgtttttaat    120
atttc                                                                125

<210> SEQ ID NO 29
<211> LENGTH: 55
<212> TYPE: DNA
<213> ORGANISM: Artificial Sequence
<220> FEATURE:
<223> OTHER INFORMATION: Synthetic sequence, poly A tail

<400> SEQUENCE: 29
aaaaaaaaaa aaaaaaaaaa aaaaaaaaaa aaaaaaaaaa aaaaaaaaaa aaaaa          55

<210> SEQ ID NO 30
<211> LENGTH: 2493
<212> TYPE: PRT
<213> ORGANISM: Artificial Sequence
<220> FEATURE:
<223> OTHER INFORMATION: Synthetic sequence, VEEV TC-83 Replicon nsP1-4
      amino acid sequence
<220> FEATURE:
<221> NAME/KEY: misc_feature
<222> LOCATION: (1880)..(1880)
<223> OTHER INFORMATION: Xaa can be any naturally occurring amino acid

<400> SEQUENCE: 30

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140
```

```
Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
            165                 170                 175

Gly Phe Asp Thr Thr Pro Phe Met Phe Lys Asn Leu Ala Gly Ala Tyr
                180                 185                 190

Pro Ser Tyr Ser Thr Asn Trp Ala Asp Glu Thr Val Leu Thr Ala Arg
            195                 200                 205

Asn Ile Gly Leu Cys Ser Ser Asp Val Met Glu Arg Ser Arg Arg Gly
        210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
            450                 455                 460

Arg Thr Arg Ile Arg Lys Met Leu Glu Glu His Lys Glu Pro Ser Pro
465                 470                 475                 480

Leu Ile Thr Ala Glu Asp Ile Gln Glu Ala Lys Cys Ala Ala Asp Glu
                485                 490                 495

Ala Lys Glu Val Arg Glu Ala Glu Leu Arg Ala Ala Leu Pro Pro
            500                 505                 510

Leu Ala Ala Asp Phe Glu Glu Pro Thr Leu Glu Ala Asp Val Asp Leu
            515                 520                 525

Met Leu Gln Glu Ala Gly Ala Gly Ser Val Glu Thr Pro Arg Gly Leu
        530                 535                 540

Ile Lys Val Thr Ser Tyr Ala Gly Glu Asp Lys Ile Gly Ser Tyr Ala
545                 550                 555                 560
```

```
Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Pro Glu
        595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Arg Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
        915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Ile Leu Thr Ala Lys Tyr Pro Gly Asn
                965                 970                 975

Phe Thr Ala Thr Ile Glu Glu Trp Gln Ala Glu His Asp Ala Ile Met
```

-continued

```
                980             985             990
Arg His Ile Leu Glu Arg Pro Asp Pro Thr Asp Val Phe Gln Asn Lys
            995             1000            1005
Ala Asn Val Cys Trp Ala Lys Ala Leu Val Pro Val Leu Lys Thr
    1010            1015            1020
Ala Gly Ile Asp Met Thr Thr Glu Gln Trp Asn Thr Val Asp Tyr
    1025            1030            1035
Phe Glu Thr Asp Lys Ala His Ser Ala Glu Ile Val Leu Asn Gln
    1040            1045            1050
Leu Cys Val Arg Phe Phe Gly Leu Asp Leu Asp Ser Gly Leu Phe
    1055            1060            1065
Ser Ala Pro Thr Val Pro Leu Ser Ile Arg Asn Asn His Trp Asp
    1070            1075            1080
Asn Ser Pro Ser Pro Asn Met Tyr Gly Leu Asn Lys Glu Val Val
    1085            1090            1095
Arg Gln Leu Ser Arg Arg Tyr Pro Gln Leu Pro Arg Ala Val Ala
    1100            1105            1110
Thr Gly Arg Val Tyr Asp Met Asn Thr Gly Thr Leu Arg Asn Tyr
    1115            1120            1125
Asp Pro Arg Ile Asn Leu Val Pro Val Asn Arg Arg Leu Pro His
    1130            1135            1140
Ala Leu Val Leu His His Asn Glu His Pro Gln Ser Asp Phe Ser
    1145            1150            1155
Ser Phe Val Ser Lys Leu Lys Gly Arg Thr Val Leu Val Val Gly
    1160            1165            1170
Glu Lys Leu Ser Val Pro Gly Lys Lys Val Asp Trp Leu Ser Asp
    1175            1180            1185
Gln Pro Glu Ala Thr Phe Arg Ala Arg Leu Asp Leu Gly Ile Pro
    1190            1195            1200
Gly Asp Val Pro Lys Tyr Asp Ile Val Phe Ile Asn Val Arg Thr
    1205            1210            1215
Pro Tyr Lys Tyr His His Tyr Gln Gln Cys Glu Asp His Ala Ile
    1220            1225            1230
Lys Leu Ser Met Leu Thr Lys Lys Ala Cys Leu His Leu Asn Pro
    1235            1240            1245
Gly Gly Thr Cys Val Ser Ile Gly Tyr Gly Tyr Ala Asp Arg Ala
    1250            1255            1260
Ser Glu Ser Ile Ile Gly Ala Ile Ala Arg Gln Phe Lys Phe Ser
    1265            1270            1275
Arg Val Cys Lys Pro Lys Ser Ser His Glu Glu Thr Glu Val Leu
    1280            1285            1290
Phe Val Phe Ile Gly Tyr Asp Arg Lys Ala Arg Thr His Asn Pro
    1295            1300            1305
Tyr Lys Leu Ser Ser Thr Leu Thr Asn Ile Tyr Thr Gly Ser Arg
    1310            1315            1320
Leu His Glu Ala Gly Cys Ala Pro Ser Tyr His Val Val Arg Gly
    1325            1330            1335
Asp Ile Ala Thr Ala Thr Glu Gly Val Ile Ile Asn Ala Ala Asn
    1340            1345            1350
Ser Lys Gly Gln Pro Gly Gly Gly Val Cys Gly Ala Leu Tyr Lys
    1355            1360            1365
Lys Phe Pro Glu Ser Phe Asp Leu Gln Pro Ile Glu Val Gly Lys
    1370            1375            1380
```

```
Ala Arg Leu Val Lys Gly Ala Lys His Ile Ile His Ala Val
    1385            1390            1395

Gly Pro Asn Phe Asn Lys Val Ser Glu Val Glu Gly Asp Lys Gln
    1400            1405            1410

Leu Ala Glu Ala Tyr Glu Ser Ile Ala Lys Ile Val Asn Asp Asn
    1415            1420            1425

Asn Tyr Lys Ser Val Ala Ile Pro Leu Leu Ser Thr Gly Ile Phe
    1430            1435            1440

Ser Gly Asn Lys Asp Arg Leu Thr Gln Ser Leu Asn His Leu Leu
    1445            1450            1455

Thr Ala Leu Asp Thr Thr Asp Ala Asp Val Ala Ile Tyr Cys Arg
    1460            1465            1470

Asp Lys Lys Trp Glu Met Thr Leu Lys Glu Ala Val Ala Arg Arg
    1475            1480            1485

Glu Ala Val Glu Glu Ile Cys Ile Ser Asp Asp Ser Ser Val Thr
    1490            1495            1500

Glu Pro Asp Ala Glu Leu Val Arg Val His Pro Lys Ser Ser Leu
    1505            1510            1515

Ala Gly Arg Lys Gly Tyr Ser Thr Ser Asp Gly Lys Thr Phe Ser
    1520            1525            1530

Tyr Leu Glu Gly Thr Lys Phe His Gln Ala Ala Lys Asp Ile Ala
    1535            1540            1545

Glu Ile Asn Ala Met Trp Pro Val Ala Thr Glu Ala Asn Glu Gln
    1550            1555            1560

Val Cys Met Tyr Ile Leu Gly Glu Ser Met Ser Ser Ile Arg Ser
    1565            1570            1575

Lys Cys Pro Val Glu Glu Ser Glu Ala Ser Thr Pro Pro Ser Thr
    1580            1585            1590

Leu Pro Cys Leu Cys Ile His Ala Met Thr Pro Glu Arg Val Gln
    1595            1600            1605

Arg Leu Lys Ala Ser Arg Pro Glu Gln Ile Thr Val Cys Ser Ser
    1610            1615            1620

Phe Pro Leu Pro Lys Tyr Arg Ile Thr Gly Val Gln Lys Ile Gln
    1625            1630            1635

Cys Ser Gln Pro Ile Leu Phe Ser Pro Lys Val Pro Ala Tyr Ile
    1640            1645            1650

His Pro Arg Lys Tyr Leu Val Glu Thr Pro Val Glu Glu Thr
    1655            1660            1665

Pro Glu Ser Pro Ala Glu Asn Gln Ser Thr Glu Gly Thr Pro Glu
    1670            1675            1680

Gln Pro Ala Leu Val Asn Val Asp Ala Thr Arg Thr Arg Met Pro
    1685            1690            1695

Glu Pro Ile Ile Ile Glu Glu Glu Glu Asp Ser Ile Ser Leu
    1700            1705            1710

Leu Ser Asp Gly Pro Thr His Gln Val Leu Gln Val Glu Ala Asp
    1715            1720            1725

Ile His Gly Ser Pro Ser Val Ser Ser Ser Ser Trp Ser Ile Pro
    1730            1735            1740

His Ala Ser Asp Phe Asp Val Asp Ser Leu Ser Ile Leu Asp Thr
    1745            1750            1755

Leu Asp Gly Ala Ser Val Thr Ser Gly Ala Val Ser Ala Glu Thr
    1760            1765            1770
```

```
Asn Ser Tyr Phe Ala Arg Ser Met Glu Phe Arg Ala Arg Pro Val
1775                1780                1785

Pro Ala Pro Arg Thr Val Phe Arg Asn Pro Pro His Pro Ala Pro
1790                1795                1800

Arg Thr Arg Thr Pro Pro Leu Ala His Ser Arg Ala Ser Ser Arg
1805                1810                1815

Thr Ser Leu Val Ser Thr Pro Pro Gly Val Asn Arg Val Ile Thr
1820                1825                1830

Arg Glu Glu Leu Glu Ala Leu Thr Pro Ser Arg Ala Pro Ser Arg
1835                1840                1845

Ser Ala Ser Arg Thr Ser Leu Val Ser Asn Pro Pro Gly Val Asn
1850                1855                1860

Arg Val Ile Thr Arg Glu Glu Phe Glu Ala Phe Val Ala Gln Gln
1865                1870                1875

Gln Xaa Arg Phe Asp Ala Gly Ala Tyr Ile Phe Ser Ser Asp Thr
1880                1885                1890

Gly Gln Gly His Leu Gln Gln Lys Ser Val Arg Gln Thr Val Leu
1895                1900                1905

Ser Glu Val Val Leu Glu Arg Thr Glu Leu Glu Ile Ser Tyr Ala
1910                1915                1920

Pro Arg Leu Asp Gln Glu Lys Glu Glu Leu Leu Arg Lys Lys Leu
1925                1930                1935

Gln Leu Asn Pro Thr Pro Ala Asn Arg Ser Arg Tyr Gln Ser Arg
1940                1945                1950

Arg Val Glu Asn Met Lys Ala Ile Thr Ala Arg Arg Ile Leu Gln
1955                1960                1965

Gly Leu Gly His Tyr Leu Lys Ala Glu Gly Lys Val Glu Cys Tyr
1970                1975                1980

Arg Thr Leu His Pro Val Pro Leu Tyr Ser Ser Ser Val Asn Arg
1985                1990                1995

Ala Phe Ser Ser Pro Lys Val Ala Val Glu Ala Cys Asn Ala Met
2000                2005                2010

Leu Lys Glu Asn Phe Pro Thr Val Ala Ser Tyr Cys Ile Ile Pro
2015                2020                2025

Glu Tyr Asp Ala Tyr Leu Asp Met Val Asp Gly Ala Ser Cys Cys
2030                2035                2040

Leu Asp Thr Ala Ser Phe Cys Pro Ala Lys Leu Arg Ser Phe Pro
2045                2050                2055

Lys Lys His Ser Tyr Leu Glu Pro Thr Ile Arg Ser Ala Val Pro
2060                2065                2070

Ser Ala Ile Gln Asn Thr Leu Gln Asn Val Leu Ala Ala Ala Thr
2075                2080                2085

Lys Arg Asn Cys Asn Val Thr Gln Met Arg Glu Leu Pro Val Leu
2090                2095                2100

Asp Ser Ala Ala Phe Asn Val Glu Cys Phe Lys Lys Tyr Ala Cys
2105                2110                2115

Asn Asn Glu Tyr Trp Glu Thr Phe Lys Glu Asn Pro Ile Arg Leu
2120                2125                2130

Thr Glu Glu Asn Val Val Asn Tyr Ile Thr Lys Leu Lys Gly Pro
2135                2140                2145

Lys Ala Ala Ala Leu Phe Ala Lys Thr His Asn Leu Asn Met Leu
2150                2155                2160

Gln Asp Ile Pro Met Asp Arg Phe Val Met Asp Leu Lys Arg Asp
```

```
            2165                2170                2175

Val Lys Val Thr Pro Gly Thr Lys His Thr Glu Glu Arg Pro Lys
    2180                2185                2190

Val Gln Val Ile Gln Ala Ala Asp Pro Leu Ala Thr Ala Asp Leu
    2195                2200                2205

Cys Gly Ile His Arg Glu Leu Val Arg Arg Leu Asn Ala Val Leu
    2210                2215                2220

Leu Pro Asn Ile His Thr Leu Phe Asp Met Ser Ala Glu Asp Phe
    2225                2230                2235

Asp Ala Ile Ile Ala Glu His Phe Gln Pro Gly Asp Cys Val Leu
    2240                2245                2250

Glu Thr Asp Ile Ala Ser Phe Asp Lys Ser Glu Asp Asp Ala Met
    2255                2260                2265

Ala Leu Thr Ala Leu Met Ile Leu Glu Asp Leu Gly Val Asp Ala
    2270                2275                2280

Glu Leu Leu Thr Leu Ile Glu Ala Ala Phe Gly Glu Ile Ser Ser
    2285                2290                2295

Ile His Leu Pro Thr Lys Thr Lys Phe Lys Phe Gly Ala Met Met
    2300                2305                2310

Lys Ser Gly Met Phe Leu Thr Leu Phe Val Asn Thr Val Ile Asn
    2315                2320                2325

Ile Val Ile Ala Ser Arg Val Leu Arg Glu Arg Leu Thr Gly Ser
    2330                2335                2340

Pro Cys Ala Ala Phe Ile Gly Asp Asp Asn Ile Val Lys Gly Val
    2345                2350                2355

Lys Ser Asp Lys Leu Met Ala Asp Arg Cys Ala Thr Trp Leu Asn
    2360                2365                2370

Met Glu Val Lys Ile Ile Asp Ala Val Val Gly Glu Lys Ala Pro
    2375                2380                2385

Tyr Phe Cys Gly Gly Phe Ile Leu Cys Asp Ser Val Thr Gly Thr
    2390                2395                2400

Ala Cys Arg Val Ala Asp Pro Leu Lys Arg Leu Phe Lys Leu Gly
    2405                2410                2415

Lys Pro Leu Ala Val Asp Asp Glu His Asp Asp Asp Arg Arg Arg
    2420                2425                2430

Ala Leu His Glu Glu Ser Thr Arg Trp Asn Arg Val Gly Ile Leu
    2435                2440                2445

Pro Glu Leu Cys Lys Ala Val Glu Ser Arg Tyr Glu Thr Val Gly
    2450                2455                2460

Thr Ser Ile Ile Val Met Ala Met Thr Thr Leu Ala Ser Ser Val
    2465                2470                2475

Lys Ser Phe Ser Tyr Leu Arg Gly Ala Pro Ile Thr Leu Tyr Gly
    2480                2485                2490

<210> SEQ ID NO 31
<211> LENGTH: 557
<212> TYPE: PRT
<213> ORGANISM: Artificial Sequence
<220> FEATURE:
<223> OTHER INFORMATION: Synthetic sequence, VEEV TC-83 nsp3 E242K
<220> FEATURE:
<221> NAME/KEY: misc_feature
<222> LOCATION: (551)..(551)
<223> OTHER INFORMATION: Xaa can be any naturally occurring amino acid

<400> SEQUENCE: 31
```

```
Ala Pro Ser Tyr His Val Val Arg Gly Asp Ile Ala Thr Ala Thr Glu
  1               5                  10                  15

Gly Val Ile Ile Asn Ala Ala Asn Ser Lys Gly Gln Pro Gly Gly Gly
             20                  25                  30

Val Cys Gly Ala Leu Tyr Lys Lys Phe Pro Glu Ser Phe Asp Leu Gln
             35                  40                  45

Pro Ile Glu Val Gly Lys Ala Arg Leu Val Lys Gly Ala Ala Lys His
         50                  55                  60

Ile Ile His Ala Val Gly Pro Asn Phe Asn Lys Val Ser Glu Val Glu
 65                  70                  75                  80

Gly Asp Lys Gln Leu Ala Glu Ala Tyr Glu Ser Ile Ala Lys Ile Val
                 85                  90                  95

Asn Asp Asn Asn Tyr Lys Ser Val Ala Ile Pro Leu Leu Ser Thr Gly
                100                 105                 110

Ile Phe Ser Gly Asn Lys Asp Arg Leu Thr Gln Ser Leu Asn His Leu
                115                 120                 125

Leu Thr Ala Leu Asp Thr Thr Asp Ala Asp Val Ala Ile Tyr Cys Arg
        130                 135                 140

Asp Lys Lys Trp Glu Met Thr Leu Lys Glu Ala Val Ala Arg Arg Glu
145                 150                 155                 160

Ala Val Glu Glu Ile Cys Ile Ser Asp Asp Ser Ser Val Thr Glu Pro
                165                 170                 175

Asp Ala Glu Leu Val Arg Val His Pro Lys Ser Ser Leu Ala Gly Arg
                180                 185                 190

Lys Gly Tyr Ser Thr Ser Asp Gly Lys Thr Phe Ser Tyr Leu Glu Gly
            195                 200                 205

Thr Lys Phe His Gln Ala Ala Lys Asp Ile Ala Glu Ile Asn Ala Met
        210                 215                 220

Trp Pro Val Ala Thr Glu Ala Asn Glu Gln Val Cys Met Tyr Ile Leu
225                 230                 235                 240

Gly Lys Ser Met Ser Ser Ile Arg Ser Lys Cys Pro Val Glu Glu Ser
                245                 250                 255

Glu Ala Ser Thr Pro Pro Ser Thr Leu Pro Cys Leu Cys Ile His Ala
                260                 265                 270

Met Thr Pro Glu Arg Val Gln Arg Leu Lys Ala Ser Arg Pro Glu Gln
        275                 280                 285

Ile Thr Val Cys Ser Ser Phe Pro Leu Pro Lys Tyr Arg Ile Thr Gly
                290                 295                 300

Val Gln Lys Ile Gln Cys Ser Gln Pro Ile Leu Phe Ser Pro Lys Val
305                 310                 315                 320

Pro Ala Tyr Ile His Pro Arg Lys Tyr Leu Val Glu Thr Pro Pro Val
                325                 330                 335

Asp Glu Thr Pro Glu Pro Ser Ala Glu Asn Gln Ser Thr Glu Gly Thr
                340                 345                 350

Pro Glu Gln Pro Pro Leu Ile Thr Glu Asp Glu Thr Arg Thr Arg Thr
                355                 360                 365

Pro Glu Pro Ile Ile Ile Glu Glu Glu Glu Asp Ser Ile Ser Leu
        370                 375                 380

Leu Ser Asp Gly Pro Thr His Gln Val Leu Gln Val Glu Ala Asp Ile
385                 390                 395                 400

His Gly Pro Pro Ser Val Ser Ser Ser Trp Ser Ile Pro His Ala
                405                 410                 415

Ser Asp Phe Asp Val Asp Ser Leu Ser Ile Leu Asp Thr Leu Glu Gly
```

```
                420             425             430
Ala Ser Val Thr Ser Gly Ala Thr Ser Ala Glu Thr Asn Ser Tyr Phe
            435             440             445

Ala Lys Ser Met Glu Phe Leu Ala Arg Pro Val Pro Ala Pro Arg Thr
450             455             460

Val Phe Arg Asn Pro Pro His Pro Ala Pro Arg Thr Arg Thr Pro Ser
465             470             475             480

Leu Ala Pro Ser Arg Ala Cys Ser Arg Thr Ser Leu Val Ser Thr Pro
            485             490             495

Pro Gly Val Asn Arg Val Ile Thr Arg Glu Glu Leu Glu Ala Leu Thr
            500             505             510

Pro Ser Arg Thr Pro Ser Arg Ser Val Ser Arg Thr Ser Leu Val Ser
            515             520             525

Asn Pro Pro Gly Val Asn Arg Val Ile Thr Arg Glu Glu Phe Glu Ala
            530             535             540

Phe Val Ala Gln Gln Gln Xaa Arg Phe Asp Ala Gly Ala
545             550             555
```

<210> SEQ ID NO 32
<211> LENGTH: 60
<212> TYPE: PRT
<213> ORGANISM: Artificial Sequence
<220> FEATURE:
<223> OTHER INFORMATION: Synthetic sequence, mouse CD80 (TM-Cyt)

<400> SEQUENCE: 32

```
Thr Leu Val Leu Phe Gly Ala Gly Phe Gly Ala Val Ile Thr Val Val
1               5                   10                  15

Val Ile Val Val Ile Ile Lys Cys Phe Cys Lys His Arg Ser Cys Phe
            20                  25                  30

Arg Arg Asn Glu Ala Ser Arg Glu Thr Asn Asn Ser Leu Thr Phe Gly
        35                  40                  45

Pro Glu Glu Ala Leu Ala Glu Gln Thr Val Phe Leu
    50                  55                  60
```

<210> SEQ ID NO 33
<211> LENGTH: 107
<212> TYPE: PRT
<213> ORGANISM: Artificial Sequence
<220> FEATURE:
<223> OTHER INFORMATION: Synthetic sequence, mouse IgG4-CH3

<400> SEQUENCE: 33

```
Gly Arg Pro Lys Ala Pro Gln Val Tyr Thr Ile Pro Pro Pro Lys Glu
1               5                   10                  15

Gln Met Ala Lys Asp Lys Val Ser Leu Thr Cys Met Ile Thr Asn Phe
            20                  25                  30

Phe Pro Glu Asp Ile Thr Val Glu Trp Gln Trp Asn Gly Gln Pro Ala
        35                  40                  45

Glu Asn Tyr Lys Asn Thr Gln Pro Ile Met Asp Thr Asp Gly Ser Tyr
    50                  55                  60

Phe Val Tyr Ser Lys Leu Asn Val Gln Lys Ser Asn Trp Glu Ala Gly
65                  70                  75                  80

Asn Thr Phe Thr Cys Ser Val Leu His Glu Gly Leu His Asn His His
                85                  90                  95

Thr Glu Lys Ser Leu Ser His Ser Pro Gly Lys
            100                 105
```

<210> SEQ ID NO 34
<211> LENGTH: 266
<212> TYPE: PRT
<213> ORGANISM: Artificial Sequence
<220> FEATURE:
<223> OTHER INFORMATION: Synthetic sequence, construct derived from
      COVID-19 E484K_N501Y_K417T mutant (Brazil Strain Mutant)

<400> SEQUENCE: 34

Met Phe Val Phe Leu Val Leu Leu Pro Leu Val Ser Ser Val Arg Phe
1               5                   10                  15

Pro Asn Ile Thr Asn Leu Cys Pro Phe Gly Glu Val Phe Asn Ala Thr
            20                  25                  30

Arg Phe Ala Ser Val Tyr Ala Trp Asn Arg Lys Arg Ile Ser Asn Cys
        35                  40                  45

Val Ala Asp Tyr Ser Val Leu Tyr Asn Ser Ala Ser Phe Ser Thr Phe
    50                  55                  60

Lys Cys Tyr Gly Val Ser Pro Thr Lys Leu Asn Asp Leu Cys Phe Thr
65                  70                  75                  80

Asn Val Tyr Ala Asp Ser Phe Val Ile Arg Gly Asp Glu Val Arg Gln
                85                  90                  95

Ile Ala Pro Gly Gln Thr Gly Thr Ile Ala Asp Tyr Asn Tyr Lys Leu
            100                 105                 110

Pro Asp Asp Phe Thr Gly Cys Val Ile Ala Trp Asn Ser Asn Asn Leu
        115                 120                 125

Asp Ser Lys Val Gly Gly Asn Tyr Asn Tyr Leu Tyr Arg Leu Phe Arg
    130                 135                 140

Lys Ser Asn Leu Lys Pro Phe Glu Arg Asp Ile Ser Thr Glu Ile Tyr
145                 150                 155                 160

Gln Ala Gly Ser Thr Pro Cys Asn Gly Val Lys Gly Phe Asn Cys Tyr
                165                 170                 175

Phe Pro Leu Gln Ser Tyr Gly Phe Gln Pro Thr Tyr Gly Val Gly Tyr
            180                 185                 190

Gln Pro Tyr Arg Val Val Val Leu Ser Phe Glu Leu Leu His Ala Pro
        195                 200                 205

Ala Thr Val Cys Gly Pro Lys Lys Ser Thr Gly Val Lys Leu Glu Ser
    210                 215                 220

Met Gly Ile Tyr Gln Ile Leu Ala Ile Tyr Ser Thr Val Ala Ser Ser
225                 230                 235                 240

Leu Val Leu Leu Val Ser Leu Gly Ala Ile Ser Phe Trp Met Cys Ser
                245                 250                 255

Asn Gly Ser Leu Gln Cys Arg Ile Cys Ile
            260                 265

<210> SEQ ID NO 35
<211> LENGTH: 266
<212> TYPE: PRT
<213> ORGANISM: Artificial Sequence
<220> FEATURE:
<223> OTHER INFORMATION: Synthetic sequence, construct derived from
      COVID-19 E484K_N501Y_K417N mutant (South African Mutant)

<400> SEQUENCE: 35

Met Phe Val Phe Leu Val Leu Leu Pro Leu Val Ser Ser Val Arg Phe
1               5                   10                  15

Pro Asn Ile Thr Asn Leu Cys Pro Phe Gly Glu Val Phe Asn Ala Thr
            20                  25                  30

Arg Phe Ala Ser Val Tyr Ala Trp Asn Arg Lys Arg Ile Ser Asn Cys
            35                  40                  45

Val Ala Asp Tyr Ser Val Leu Tyr Asn Ser Ala Ser Phe Ser Thr Phe
 50                  55                  60

Lys Cys Tyr Gly Val Ser Pro Thr Lys Leu Asn Asp Leu Cys Phe Thr
 65                  70                  75                  80

Asn Val Tyr Ala Asp Ser Phe Val Ile Arg Gly Asp Glu Val Arg Gln
                 85                  90                  95

Ile Ala Pro Gly Gln Thr Gly Asn Ile Ala Asp Tyr Asn Tyr Lys Leu
                100                 105                 110

Pro Asp Asp Phe Thr Gly Cys Val Ile Ala Trp Asn Ser Asn Asn Leu
                115                 120                 125

Asp Ser Lys Val Gly Gly Asn Tyr Asn Tyr Leu Tyr Arg Leu Phe Arg
130                 135                 140

Lys Ser Asn Leu Lys Pro Phe Glu Arg Asp Ile Ser Thr Glu Ile Tyr
145                 150                 155                 160

Gln Ala Gly Ser Thr Pro Cys Asn Gly Val Lys Gly Phe Asn Cys Tyr
                165                 170                 175

Phe Pro Leu Gln Ser Tyr Gly Phe Gln Pro Thr Tyr Gly Val Gly Tyr
                180                 185                 190

Gln Pro Tyr Arg Val Val Val Leu Ser Phe Glu Leu Leu His Ala Pro
                195                 200                 205

Ala Thr Val Cys Gly Pro Lys Lys Ser Thr Gly Val Lys Leu Glu Ser
                210                 215                 220

Met Gly Ile Tyr Gln Ile Leu Ala Ile Tyr Ser Thr Val Ala Ser Ser
225                 230                 235                 240

Leu Val Leu Leu Val Ser Leu Gly Ala Ile Ser Phe Trp Met Cys Ser
                245                 250                 255

Asn Gly Ser Leu Gln Cys Arg Ile Cys Ile
                260                 265

<210> SEQ ID NO 36
<211> LENGTH: 266
<212> TYPE: PRT
<213> ORGANISM: Artificial Sequence
<220> FEATURE:
<223> OTHER INFORMATION: Synthetic sequence, construct derived from
      COVID-19 E484K mutant

<400> SEQUENCE: 36

Met Phe Val Phe Leu Val Leu Leu Pro Leu Val Ser Ser Val Arg Phe
 1               5                  10                  15

Pro Asn Ile Thr Asn Leu Cys Pro Phe Gly Glu Val Phe Asn Ala Thr
                 20                  25                  30

Arg Phe Ala Ser Val Tyr Ala Trp Asn Arg Lys Arg Ile Ser Asn Cys
            35                  40                  45

Val Ala Asp Tyr Ser Val Leu Tyr Asn Ser Ala Ser Phe Ser Thr Phe
 50                  55                  60

Lys Cys Tyr Gly Val Ser Pro Thr Lys Leu Asn Asp Leu Cys Phe Thr
 65                  70                  75                  80

Asn Val Tyr Ala Asp Ser Phe Val Ile Arg Gly Asp Glu Val Arg Gln
                 85                  90                  95

Ile Ala Pro Gly Gln Thr Gly Lys Ile Ala Asp Tyr Asn Tyr Lys Leu
                100                 105                 110

Pro Asp Asp Phe Thr Gly Cys Val Ile Ala Trp Asn Ser Asn Asn Leu
                115                 120                 125

```
Asp Ser Lys Val Gly Gly Asn Tyr Asn Tyr Leu Tyr Arg Leu Phe Arg
            130                 135                 140

Lys Ser Asn Leu Lys Pro Phe Glu Arg Asp Ile Ser Thr Glu Ile Tyr
145                 150                 155                 160

Gln Ala Gly Ser Thr Pro Cys Asn Gly Val Lys Gly Phe Asn Cys Tyr
                165                 170                 175

Phe Pro Leu Gln Ser Tyr Gly Phe Gln Pro Thr Asn Gly Val Gly Tyr
            180                 185                 190

Gln Pro Tyr Arg Val Val Leu Ser Phe Glu Leu Leu His Ala Pro
        195                 200                 205

Ala Thr Val Cys Gly Pro Lys Lys Ser Thr Gly Val Lys Leu Glu Ser
            210                 215                 220

Met Gly Ile Tyr Gln Ile Leu Ala Ile Tyr Ser Thr Val Ala Ser Ser
225                 230                 235                 240

Leu Val Leu Leu Val Ser Leu Gly Ala Ile Ser Phe Trp Met Cys Ser
                245                 250                 255

Asn Gly Ser Leu Gln Cys Arg Ile Cys Ile
            260                 265

<210> SEQ ID NO 37
<211> LENGTH: 207
<212> TYPE: PRT
<213> ORGANISM: Artificial Sequence
<220> FEATURE:
<223> OTHER INFORMATION: Synthetic sequence, fused protein comprising
      COVID-19 signal sequence (1-15) and COVID-19 RBD(330-521)

<400> SEQUENCE: 37

Met Phe Val Phe Leu Val Leu Leu Pro Leu Val Ser Ser Gln Cys Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro
        195                 200                 205
```

```
<210> SEQ ID NO 38
<211> LENGTH: 260
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19 RBD(330-521)and HA(flexible-TM-
      Cyt)

<400> SEQUENCE: 38

Met Tyr Arg Met Gln Leu Leu Ser Cys Ile Ala Leu Ser Leu Ala Leu
1               5                   10                  15

Val Thr Asn Ser Pro Asn Ile Thr Asn Leu Cys Pro Phe Gly Glu Val
            20                  25                  30

Phe Asn Ala Thr Arg Phe Ala Ser Val Tyr Ala Trp Asn Arg Lys Arg
        35                  40                  45

Ile Ser Asn Cys Val Ala Asp Tyr Ser Val Leu Tyr Asn Ser Ala Ser
    50                  55                  60

Phe Ser Thr Phe Lys Cys Tyr Gly Val Ser Pro Thr Lys Leu Asn Asp
65                  70                  75                  80

Leu Cys Phe Thr Asn Val Tyr Ala Asp Ser Phe Val Ile Arg Gly Asp
                85                  90                  95

Glu Val Arg Gln Ile Ala Pro Gly Gln Thr Gly Lys Ile Ala Asp Tyr
            100                 105                 110

Asn Tyr Lys Leu Pro Asp Asp Phe Thr Gly Cys Val Ile Ala Trp Asn
        115                 120                 125

Ser Asn Asn Leu Asp Ser Lys Val Gly Gly Asn Tyr Asn Tyr Leu Tyr
    130                 135                 140

Arg Leu Phe Arg Lys Ser Asn Leu Lys Pro Phe Glu Arg Asp Ile Ser
145                 150                 155                 160

Thr Glu Ile Tyr Gln Ala Gly Ser Thr Pro Cys Asn Gly Val Glu Gly
                165                 170                 175

Phe Asn Cys Tyr Phe Pro Leu Gln Ser Tyr Gly Phe Gln Pro Thr Asn
            180                 185                 190

Gly Val Gly Tyr Gln Pro Tyr Arg Val Val Val Leu Ser Phe Glu Leu
        195                 200                 205

Leu His Ala Pro Gly Val Lys Leu Glu Ser Met Gly Ile Tyr Gln Ile
    210                 215                 220

Leu Ala Ile Tyr Ser Thr Val Ala Ser Ser Leu Val Leu Leu Val Ser
225                 230                 235                 240

Leu Gly Ala Ile Ser Phe Trp Met Cys Ser Asn Gly Ser Leu Gln Cys
                245                 250                 255

Arg Ile Cys Ile
            260

<210> SEQ ID NO 39
<211> LENGTH: 364
<212> TYPE: PRT
<213> ORGANISM: Artificial Sequence
<220> FEATURE:
<223> OTHER INFORMATION: Synthetic sequence, fused protein comprising
      COVID-19 signal sequence (1-15), COVID-19 RBD(330-521), Human
      IgG4CH3 and Human CD80 (TM-Cyt)

<400> SEQUENCE: 39

Met Phe Val Phe Leu Val Leu Leu Pro Leu Val Ser Ser Gln Cys Pro
1               5                   10                  15

Asn Ile Thr Asn Leu Cys Pro Phe Gly Glu Val Phe Asn Ala Thr Arg
            20                  25                  30
```

Phe Ala Ser Val Tyr Ala Trp Asn Arg Lys Arg Ile Ser Asn Cys Val
            35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
                100                 105                 110

Asp Asp Phe Thr Gly Cys Val Ile Ala Trp Asn Ser Asn Leu Asp
                115                 120                 125

Ser Lys Val Gly Gly Asn Tyr Asn Tyr Leu

Asn Ile Thr Asn Leu Cys Pro Phe Gly Glu Val Phe Asn Ala Thr Arg
                20                  25                  30

Phe Ala Ser Val Tyr Ala Trp Asn Arg Lys Arg Ile Ser Asn Cys Val
            35                  40                  45

Ala Asp Tyr Ser Val Leu Tyr Asn Ser Ala Ser Phe Ser Thr Phe Lys
        50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Gly
        195                 200                 205

Ser Gly Gln Pro Arg Glu Pro Gln Val Tyr Thr Leu Pro Pro Ser Gln
210                 215                 220

Glu Glu Met Thr Lys Asn Gln Val Ser Leu Thr Cys Leu Val Lys Gly
225                 230                 235                 240

Phe Tyr Pro Ser Asp Ile Ala Val Glu Trp Glu Ser Asn Gly Gln Pro
                245                 250                 255

Glu Asn Asn Tyr Lys Thr Thr Pro Pro Val Leu Asp Ser Asp Gly Ser
            260                 265                 270

Phe Phe Leu Tyr Ser Arg Leu Thr Val Asp Lys Ser Arg Trp Gln Glu
        275                 280                 285

Gly Asn Val Phe Ser Cys Ser Val Met His Glu Ala Leu His Asn His
290                 295                 300

Tyr Thr Gln Lys Ser Leu Ser Leu Ser Leu Gly Lys Gly Ser Gly Val
305                 310                 315                 320

Lys Leu Glu Ser Met Gly Ile Tyr Gln Ile Leu Ala Ile Tyr Ser Thr
                325                 330                 335

Val Ala Ser Ser Leu Val Leu Leu Val Ser Leu Gly Ala Ile Ser Phe
            340                 345                 350

Trp Met Cys Ser Asn Gly Ser Leu Gln Cys Arg Ile Cys Ile
        355                 360                 365

<210> SEQ ID NO 41
<211> LENGTH: 373
<212> TYPE: PRT
<213> ORGANISM: Artificial Sequence
<220> FEATURE:
<223> OTHER INFORMATION: Synthetic sequence, fused protein comprising
      COVID-19 signal sequence (1-15), COVID-19 RBD(330-530), Human IgG4CH3 and Human CD80 (TM-Cyt)

<400> SEQUENCE: 41

```
Met Phe Val Phe Leu Val Leu Leu Pro Leu Val Ser Ser Gln Cys Pro
```

```
1               5               10              15
Asn Ile Thr Asn Leu Cys Pro Phe Gly Glu Val Phe Asn Ala Thr Arg
                20              25              30
Phe Ala Ser Val Tyr Ala Trp Asn Arg Lys Arg Ile Ser Asn Cys Val
                35              40              45
Ala Asp Tyr Ser Val Leu Tyr Asn Ser Ala Ser Phe Ser Thr Phe Lys
                50              55              60
Cys Tyr Gly Val Ser Pro Thr Lys Leu Asn Asp Leu Cys Phe Thr Asn
65              70              75              80
Val Tyr Ala Asp Ser Phe Val Ile Arg Gly Asp Glu Val Arg Gln Ile
                85              90              95
Ala Pro Gly Gln Thr Gly Lys Ile Ala Asp Tyr Asn Tyr Lys Leu Pro
                100             105             110
Asp Asp Phe Thr Gly Cys Val Ile Ala Trp Asn Ser Asn Asn Leu Asp
                115             120             125
Ser Lys Val Gly Gly Asn Tyr Asn Tyr Leu Tyr Arg Leu Phe Arg Lys
130             135             140
Ser Asn Leu Lys Pro Phe Glu Arg Asp Ile Ser Thr Glu Ile Tyr Gln
145             150             155             160
Ala Gly Ser Thr Pro Cys Asn Gly Val Glu Gly Phe Asn Cys Tyr Phe
                165             170             175
Pro Leu Gln Ser Tyr Gly Phe Gln Pro Thr Asn Gly Val Gly Tyr Gln
                180             185             190
Pro Tyr Arg Val Val Val Leu Ser Phe Glu Leu Leu His Ala Pro Ala
                195             200             205
Thr Val Cys Gly Pro Lys Lys Ser Gly Ser Gly Gln Pro Arg Glu Pro
210             215             220
Gln Val Tyr Thr Leu Pro Pro Ser Gln Glu Glu Met Thr Lys Asn Gln
225             230             235             240
Val Ser Leu Thr Cys Leu Val Lys Gly Phe Tyr Pro Ser Asp Ile Ala
                245             250             255
Val Glu Trp Glu Ser Asn Gly Gln Pro Glu Asn Asn Tyr Lys Thr Thr
                260             265             270
Pro Pro Val Leu Asp Ser Asp Gly Ser Phe Phe Leu Tyr Ser Arg Leu
                275             280             285
Thr Val Asp Lys Ser Arg Trp Gln Glu Gly Asn Val Phe Ser Cys Ser
                290             295             300
Val Met His Glu Ala Leu His Asn His Tyr Thr Gln Lys Ser Leu Ser
305             310             315             320
Leu Ser Leu Gly Lys Gly Ser Leu Leu Pro Ser Trp Ala Ile Thr Leu
                325             330             335
Ile Ser Val Asn Gly Ile Phe Val Ile Cys Cys Leu Thr Tyr Cys Phe
                340             345             350
Ala Pro Arg Cys Arg Glu Arg Arg Asn Glu Arg Leu Arg Arg Glu
                355             360             365
Ser Val Arg Pro Val
        370
```

<210> SEQ ID NO 42
<211> LENGTH: 375
<212> TYPE: PRT
<213> ORGANISM: Artificial Sequence
<220> FEATURE:
<223> OTHER INFORMATION: Synthetic sequence, fused protein comprising
      COVID-19 signal sequence (1-15), COVID-19 RBD(330-530), Human IgG4CH3 and HA(flexible-TM-Cyt)

<400> SEQUENCE: 42

```
Met Phe Val Phe Leu Val Leu Leu Pro Leu Val Ser Ser Gln Cys Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
        195                 200                 205

Thr Val Cys Gly Pro Lys Lys Ser Gly Ser Gly Gln Pro Arg Glu Pro
    210                 215                 220

Gln Val Tyr Thr Leu Pro Pro Ser Gln Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Arg Leu
        275                 280                 285

Thr Val Asp Lys Ser Arg Trp Gln Glu Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Leu Gly Lys Gly Ser Gly Val Lys Leu Glu Ser Met Gly Ile
                325                 330                 335

Tyr Gln Ile Leu Ala Ile Tyr Ser Thr Val Ala Ser Ser Leu Val Leu
            340                 345                 350

Leu Val Ser Leu Gly Ala Ile Ser Phe Trp Met Cys Ser Asn Gly Ser
        355                 360                 365

Leu Gln Cys Arg Ile Cys Ile
    370                 375
```

<210> SEQ ID NO 43
<211> LENGTH: 369

```
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19 RBD(330-521), Human IgG4CH3 and
      Human CD80 (TM-Cyt)

<400> SEQUENCE: 43

Met Tyr Arg Met Gln Leu Leu Ser Cys Ile Ala Leu Ser Leu Ala Leu
1               5                   10                  15

Val Thr Asn Ser Pro Asn Ile Thr Asn Leu Cys Pro Phe Gly Glu Val
            20                  25                  30

Phe Asn Ala Thr Arg Phe Ala Ser Val Tyr Ala Trp Asn Arg Lys Arg
        35                  40                  45

Ile Ser Asn Cys Val Ala Asp Tyr Ser Val Leu Tyr Asn Ser Ala Ser
    50                  55                  60

Phe Ser Thr Phe Lys Cys Tyr Gly Val Ser Pro Thr Lys Leu Asn Asp
65                  70                  75                  80

Leu Cys Phe Thr Asn Val Tyr Ala Asp Ser Phe Val Ile Arg Gly Asp
                85                  90                  95

Glu Val Arg Gln Ile Ala Pro Gly Gln Thr Gly Lys Ile Ala Asp Tyr
            100                 105                 110

Asn Tyr Lys Leu Pro Asp Asp Phe Thr Gly Cys Val Ile Ala Trp Asn
        115                 120                 125

Ser Asn Asn Leu Asp Ser Lys Val Gly Gly Asn Tyr Asn Tyr Leu Tyr
    130                 135                 140

Arg Leu Phe Arg Lys Ser Asn Leu Lys Pro Phe Glu Arg Asp Ile Ser
145                 150                 155                 160

Thr Glu Ile Tyr Gln Ala Gly Ser Thr Pro Cys Asn Gly Val Glu Gly
                165                 170                 175

Phe Asn Cys Tyr Phe Pro Leu Gln Ser Tyr Gly Phe Gln Pro Thr Asn
            180                 185                 190

Gly Val Gly Tyr Gln Pro Tyr Arg Val Val Val Leu Ser Phe Glu Leu
        195                 200                 205

Leu His Ala Pro Gly Ser Gly Gln Pro Arg Glu Pro Gln Val Tyr Thr
    210                 215                 220

Leu Pro Pro Ser Gln Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Arg Leu Thr Val Asp Lys
        275                 280                 285

Ser Arg Trp Gln Glu Gly Asn Val Phe Ser Cys Ser Val Met His Glu
    290                 295                 300

Ala Leu His Asn His Tyr Thr Gln Lys Ser Leu Ser Leu Ser Leu Gly
305                 310                 315                 320

Lys Gly Ser Leu Leu Pro Ser Trp Ala Ile Thr Leu Ile Ser Val Asn
                325                 330                 335

Gly Ile Phe Val Ile Cys Cys Leu Thr Tyr Cys Phe Ala Pro Arg Cys
            340                 345                 350

Arg Glu Arg Arg Arg Asn Glu Arg Leu Arg Arg Glu Ser Val Arg Pro
        355                 360                 365

Val
```

<210> SEQ ID NO 44
<211> LENGTH: 371
<212> TYPE: PRT
<213> ORGANISM: Artificial Sequence
<220> FEATURE:
<223> OTHER INFORMATION: Synthetic sequence, fused protein comprising hIL-2 signal sequence, COVID-19 RBD(330-521), Human IgG4CH3 and HA(flexible-TM-Cyt)

<400> SEQUENCE: 44

```
Met Tyr Arg Met Gln Leu Leu Ser Cys Ile Ala Leu Ser Leu Ala Leu
1               5                   10                  15

Val Thr Asn Ser Pro Asn Ile Thr Asn Leu Cys Pro Phe Gly Glu Val
            20                  25                  30

Phe Asn Ala Thr Arg Phe Ala Ser Val Tyr Ala Trp Asn Arg Lys Arg
        35                  40                  45

Ile Ser Asn Cys Val Ala Asp Tyr Ser Val Leu Tyr Asn Ser Ala Ser
    50                  55                  60

Phe Ser Thr Phe Lys Cys Tyr Gly Val Ser Pro Thr Lys Leu Asn Asp
65                  70                  75                  80

Leu Cys Phe Thr Asn Val Tyr Ala Asp Ser Phe Val Ile Arg Gly Asp
                85                  90                  95

Glu Val Arg Gln Ile Ala Pro Gly Gln Thr Gly Lys Ile Ala Asp Tyr
            100                 105                 110

Asn Tyr Lys Leu Pro Asp Asp Phe Thr Gly Cys Val Ile Ala Trp Asn
        115                 120                 125

Ser Asn Asn Leu Asp Ser Lys Val Gly Gly Asn Tyr Asn Tyr Leu Tyr
    130                 135                 140

Arg Leu Phe Arg Lys Ser Asn Leu Lys Pro Phe Glu Arg Asp Ile Ser
145                 150                 155                 160

Thr Glu Ile Tyr Gln Ala Gly Ser Thr Pro Cys Asn Gly Val Glu Gly
                165                 170                 175

Phe Asn Cys Tyr Phe Pro Leu Gln Ser Tyr Gly Phe Gln Pro Thr Asn
            180                 185                 190

Gly Val Gly Tyr Gln Pro Tyr Arg Val Val Val Leu Ser Phe Glu Leu
        195                 200                 205

Leu His Ala Pro Gly Ser Gly Gln Pro Arg Glu Pro Gln Val Tyr Thr
    210                 215                 220

Leu Pro Pro Ser Gln Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Arg Leu Thr Val Asp Lys
        275                 280                 285

Ser Arg Trp Gln Glu Gly Asn Val Phe Ser Cys Ser Val Met His Glu
    290                 295                 300

Ala Leu His Asn His Tyr Thr Gln Lys Ser Leu Ser Leu Ser Leu Gly
305                 310                 315                 320

Lys Gly Ser Gly Val Lys Leu Glu Ser Met Gly Ile Tyr Gln Ile Leu
                325                 330                 335

Ala Ile Tyr Ser Thr Val Ala Ser Ser Leu Val Leu Leu Val Ser Leu
            340                 345                 350
```

```
Gly Ala Ile Ser Phe Trp Met Cys Ser Asn Gly Ser Leu Gln Cys Arg
            355                 360                 365

Ile Cys Ile
    370

<210> SEQ ID NO 45
<211> LENGTH: 378
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19 RBD(330

```
                    325                 330                 335
Trp Ala Ile Thr Leu Ile Ser Val Asn Gly Ile Phe Val Ile Cys Cys
                340                 345                 350

Leu Thr Tyr Cys Phe Ala Pro Arg Cys Arg Glu Arg Arg Asn Glu
            355                 360                 365

Arg Leu Arg Arg Glu Ser Val Arg Pro Val
    370                 375

<210> SEQ ID NO 46
<211> LENGTH: 380
<212> TYPE: PRT
<213> ORGANISM: Artificial Sequence
<220> FEATURE:
<223> OTHER INFORMATION: Synthetic sequence, fused protein comprising
      hIL-2 signal sequence, COVID-19 RBD(330-530), Human IgG4CH3 and
      HA(flexible-TM-Cyt)

<400> SEQUENCE: 46

Met Tyr Arg Met Gln Leu Leu Ser Cys Ile Ala Leu Ser Leu Ala Leu
1               5                   10

```
Val Phe Ser Cys Ser Val Met His Glu Ala Leu His Asn His Tyr Thr
305                 310                 315                 320

Gln Lys Ser Leu Ser Leu Ser Leu Gly Lys Gly Ser Gly Val Lys Leu
            325                 330                 335

Glu Ser Met Gly Ile Tyr Gln Ile Leu Ala Ile Tyr Ser Thr Val Ala
            340                 345                 350

Ser Ser Leu Val Leu Leu Val Ser Leu Gly Ala Ile Ser Phe Trp Met
            355                 360                 365

Cys Ser Asn Gly Ser Leu Gln Cys Arg Ile Cys Ile
            370                 375                 380
```

<210> SEQ ID NO 47
<211> LENGTH: 266
<212> TYPE: PRT
<213> ORGANISM: Artificial Sequence
<220> FEATURE:
<223> OTHER INFORMATION: Synthetic sequence, fused protein comprising
      COVID-19 signal sequence (1-13), COVID-19 RBD(327-531) and
      HA(flexible-TM-Cyt)

<400> SEQUENCE: 47

```
Met Phe Val Phe Leu Val Leu Leu Pro Leu Val Ser Ser Val Arg Phe
1               5                   10                  15

Pro Asn Ile Thr Asn Leu Cys Pro Phe Gly Glu Val Phe Asn Ala Thr
            20                  25                  30

Arg Phe Ala Ser Val Tyr Ala Trp Asn Arg Lys Arg Ile Ser Asn Cys
            35                  40                  45

Val Ala Asp Tyr Ser Val Leu Tyr Asn Ser Ala Ser Phe Ser Thr Phe
50                  55                  60

Lys Cys Tyr Gly Val Ser Pro Thr Lys Leu Asn Asp Leu Cys Phe Thr
65                  70                  75                  80

Asn Val Tyr Ala Asp Ser Phe Val Ile Arg Gly Asp Glu Val Arg Gln
            85                  90                  95

Ile Ala Pro Gly Gln Thr Gly Lys Ile Ala Asp Tyr Asn Tyr Lys Leu
            100                 105                 110

Pro Asp Asp Phe Thr Gly Cys Val Ile Ala Trp Asn Ser Asn Asn Leu
            115                 120                 125

Asp Ser Lys Val Gly Gly Asn Tyr Asn Tyr Leu Tyr Arg Leu Phe Arg
130                 135                 140

Lys Ser Asn Leu Lys Pro Phe Glu Arg Asp Ile Ser Thr Glu Ile Tyr
145                 150                 155                 160

Gln Ala Gly Ser Thr Pro Cys Asn Gly Val Glu Gly Phe Asn Cys Tyr
            165                 170                 175

Phe Pro Leu Gln Ser Tyr Gly Phe Gln Pro Thr Asn Gly Val Gly Tyr
            180                 185                 190

Gln Pro Tyr Arg Val Val Val Leu Ser Phe Glu Leu Leu His Ala Pro
            195                 200                 205

Ala Thr Val Cys Gly Pro Lys Lys Ser Thr Gly Val Lys Leu Glu Ser
            210                 215                 220

Met Gly Ile Tyr Gln Ile Leu Ala Ile Tyr Ser Thr Val Ala Ser Ser
225                 230                 235                 240

Leu Val Leu Leu Val Ser Leu Gly Ala Ile Ser Phe Trp Met Cys Ser
            245                 250                 255

Asn Gly Ser Leu Gln Cys Arg Ile Cys Ile
            260                 265
```

<210> SEQ ID NO 48
<211> LENGTH: 264
<212> TYPE: PRT
<213> ORGANISM: Artificial Sequence
<220> FEATURE:
<223> OTHER INFORMATION: Synthetic sequence, fused protein comprising
      COVID-19 signal sequence (1-15), COVID-19 RBD(330-521) and
      HA(flexible-TM-Cyt)

<400> SEQUENCE: 48

Met Phe Val Phe Leu Val Leu Leu Pro Leu Val Ser Ser Gln Cys Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
        195                 200                 205

Thr Val Cys Gly Pro Lys Lys Ser Gly Val Lys Leu Glu Ser Met Gly
    210                 215                 220

Ile Tyr Gln Ile Leu Ala Ile Tyr Ser Thr Val Ala Ser Ser Leu Val
225                 230                 235                 240

Leu Leu Val Ser Leu Gly Ala Ile Ser Phe Trp Met Cys Ser Asn Gly
                245                 250                 255

Ser Leu Gln Cys Arg Ile Cys Ile
            260

<210> SEQ ID NO 49
<211> LENGTH: 291
<212> TYPE: PRT
<213> ORGANISM: Artificial Sequence
<220> FEATURE:
<223> OTHER INFORMATION: Synthetic sequence, fused protein comprising
      COVID-19 signal sequence (1-15), COVID-19 RBD(327-531) and COVID19
      (JMD-TM)

<400> SEQUENCE: 49

Met Phe Val Phe Leu Val Leu Leu Pro Leu Val Ser Ser Gln Cys Val
1               5                   10                  15

Arg Phe Pro Asn Ile Thr Asn Leu Cys Pro Phe Gly Glu Val Phe Asn

```
                20                  25                  30
Ala Thr Arg Phe Ala Ser Val Tyr Ala Trp Asn Arg Lys Arg Ile Ser
            35                  40                  45

Asn Cys Val Ala Asp Tyr Ser Val Leu Tyr Asn Ser Ala Ser Phe Ser
 50                  55                  60

Thr Phe Lys Cys Tyr Gly Val Ser Pro Thr Lys Leu Asn Asp Leu Cys
 65                  70                  75                  80

Phe Thr Asn Val Tyr Ala Asp Ser Phe Val Ile Arg Gly Asp Glu Val
                85                  90                  95

Arg Gln Ile Ala Pro Gly Gln Thr Gly Lys Ile Ala Asp Tyr Asn Tyr
            100                 105                 110

Lys Leu Pro Asp Asp Phe Thr Gly Cys Val Ile Ala Trp Asn Ser Asn
            115                 120                 125

Asn Leu Asp Ser Lys Val Gly Gly Asn Tyr Asn Tyr Leu Tyr Arg Leu
130                 135                 140

Phe Arg Lys Ser Asn Leu Lys Pro Phe Glu Arg Asp Ile Ser Thr Glu
145                 150                 155                 160

Ile Tyr Gln Ala Gly Ser Thr Pro Cys Asn Gly Val Glu Gly Phe Asn
                165                 170                 175

Cys Tyr Phe Pro Leu Gln Ser Tyr Gly Phe Gln Pro Thr Asn Gly Val
            180                 185                 190

Gly Tyr Gln Pro Tyr Arg Val Val Val Leu Ser Phe Glu Leu Leu His
            195                 200                 205

Ala Pro Ala Thr Val Cys Gly Pro Lys Lys Ser Thr Cys Gly Lys Tyr
            210                 215                 220

Glu Gln Tyr Ile Lys Trp Pro Trp Tyr Ile Trp Leu Gly Phe Ile Ala
225                 230                 235                 240

Gly Leu Ile Ala Ile Val Met Val Thr Ile Met Leu Cys Cys Met Thr
                245                 250                 255

Ser Cys Cys Ser Cys Leu Lys Gly Cys Cys Ser Cys Gly Ser Cys Cys
            260                 265                 270

Lys Phe Asp Glu Asp Asp Ser Glu Pro Val Leu Lys Gly Val Lys Leu
            275                 280                 285

His Tyr Thr
290

<210> SEQ ID NO 50
<211> LENGTH: 288
<212> TYPE: PRT
<213> ORGANISM: Artificial Sequence
<220> FEATURE:
<223> OTHER INFORMATION: Synthetic sequence, fused protein comprising
      COVID-19 signal sequence (1-13), COVID-19 RBD(327-531) and COVID19
      (JMD-TM)

<400> SEQUENCE: 50

Met Phe Val Phe Leu Val Leu Leu Pro Leu Val Ser Ser Val Arg Phe
 1               5                  10                  15

Pro Asn Ile Thr Asn Leu Cys Pro Phe Gly Glu Val Phe Asn Ala Thr
                20                  25                  30

Arg Phe Ala Ser Val Tyr Ala Trp Asn Arg Lys Arg Ile Ser Asn Cys
            35                  40                  45

Val Ala Asp Tyr Ser Val Leu Tyr Asn Ser Ala Ser Phe Ser Thr Phe
 50                  55                  60

Lys Cys Tyr Gly Val Ser Pro Thr Lys Leu Asn Asp Leu Cys Phe Thr
 65                  70                  75                  80
```

Asn Val Tyr Ala Asp Ser Phe Val Ile Arg Gly Asp Glu Val Arg Gln
85 90 95

Ile Ala Pro Gly Gln Thr Gly Lys Ile Ala Asp Tyr Asn Tyr Lys Leu
100 105 110

Pro Asp Asp Phe Thr Gly Cys Val Ile Ala Trp Asn Ser Asn Asn Leu
115 120 125

Asp Ser Lys Val Gly Gly Asn Tyr Asn Tyr Leu Tyr Arg Leu Phe Arg
130 135 140

Lys Ser Asn Leu Lys Pro Phe Glu Arg Asp Ile Ser Thr Glu Ile Tyr
145 150 155 160

Gln Ala Gly Ser Thr Pro Cys Asn Gly Val Glu Gly Phe Asn Cys Tyr
165 170 175

Phe Pro Leu Gln Ser Tyr Gly Phe Gln Pro Thr Asn Gly Val Gly Tyr
180 185 190

Gln Pro Tyr Arg Val Val Val Leu Ser Phe Glu Leu Leu His Ala Pro
195 200 205

Ala Thr Val Cys Gly Pro Lys Lys Ser Thr Gly Lys Tyr Glu Gln Tyr
210 215 220

Ile Lys Trp Pro Trp Tyr Ile Trp Leu Gly Phe Ile Ala Gly Leu Ile
225 230 235 240

Ala Ile Val Met Val Thr Ile Met Leu Cys Cys Met Thr Ser Cys Cys
245 250 255

Ser Cys Leu Lys Gly Cys Cys Ser Cys Gly Ser Cys Cys Lys Phe Asp
260 265 270

Glu Asp Asp Ser Glu Pro Val Leu Lys Gly Val Lys Leu His Tyr Thr
275 280 285

<210> SEQ ID NO 51
<211> LENGTH: 275
<212> TYPE: PRT
<213> ORGANISM: Artificial Sequence
<220> FEATURE:
<223> OTHER INFORMATION: Synthetic sequence, fused protein comprising COVID-19 signal sequence (1-13), COVID-19 RBD(330-521) and COVID19 (JMD-TM)

<400> SEQUENCE: 51

Met Phe Val Phe Leu Val Leu Leu Pro Leu Val Ser Ser Pro Asn Ile
1 5 10 15

Thr Asn Leu Cys Pro Phe Gly Glu Val Phe Asn Ala Thr Arg Phe Ala
20 25 30

Ser Val Tyr Ala Trp Asn Arg Lys Arg Ile Ser Asn Cys Val Ala Asp
35 40 45

Tyr Ser Val Leu Tyr Asn Ser Ala Ser Phe Ser Thr Phe Lys Cys Tyr
50 55 60

Gly Val Ser Pro Thr Lys Leu Asn Asp Leu Cys Phe Thr Asn Val Tyr
65 70 75 80

Ala Asp Ser Phe Val Ile Arg Gly Asp Glu Val Arg Gln Ile Ala Pro
85 90 95

Gly Gln Thr Gly Lys Ile Ala Asp Tyr Asn Tyr Lys Leu Pro Asp Asp
100 105 110

Phe Thr Gly Cys Val Ile Ala Trp Asn Ser Asn Asn Leu Asp Ser Lys
115 120 125

Val Gly Gly Asn Tyr Asn Tyr Leu Tyr Arg Leu Phe Arg Lys Ser Asn
130 135 140

-continued

```
Leu Lys Pro Phe Glu Arg Asp Ile Ser Thr Glu Ile Tyr Gln Ala Gly
145                 150                 155                 160

Ser Thr Pro Cys Asn Gly Val Glu Gly Phe Asn Cys Tyr Phe Pro Leu
                165                 170                 175

Gln Ser Tyr Gly Phe Gln Pro Thr Asn Gly Val Gly Tyr Gln Pro Tyr
            180                 185                 190

Arg Val Val Val Leu Ser Phe Glu Leu Leu His Ala Pro Gly Lys Tyr
        195                 200                 205

Glu Gln Tyr Ile Lys Trp Pro Trp Tyr Ile Trp Leu Gly Phe Ile Ala
        210                 215                 220

Gly Leu Ile Ala Ile Val Met Val Thr Ile Met Leu Cys Cys Met Thr
225                 230                 235                 240

Ser Cys Cys Ser Cys Leu Lys Gly Cys Cys Ser Cys Gly Ser Cys Cys
                245                 250                 255

Lys Phe Asp Glu Asp Asp Ser Glu Pro Val Leu Lys Gly Val Lys Leu
                260                 265                 270

His Tyr Thr
        275
```

ALPHAVIRUS REPLICON ENCODING CHIMERIC SARS-CoV-2 RECEPTOR BINDING DOMAINS

CROSS REFERENCE TO RELATED APPLICATIONS

This application claims the benefit of U.S. Provisional Patent Application Nos. 63/011,561 filed on Apr. 17, 2020, 63/050,442 filed on Jul. 10, 2020 and 63/088,723 filed on Oct. 7, 2020. The entire disclosure of those prior applications are hereby incorporated by reference.

TECHNICAL FIELD

The present disclosure relates generally to the field of a vaccine and to a method and a composition for treating and/or immunizing against viral infections. In particular, the present disclosure relates to a vaccine for coronavirus such as SARS-CoV-2 (COVID-19).

BACKGROUND

Coronaviruses are a large family of viruses that usually cause mild to moderate upper-respiratory tract illnesses, like the common cold. However, three new coronaviruses have emerged from animal reservoirs over the past two decades to cause serious and widespread illness and death.

There are hundreds of coronaviruses, most of which circulate among such animals as pigs, camels, bats and cats. Sometimes those viruses jump to humans—called a spillover event—and can cause disease. Four of the seven known coronaviruses that sicken people cause only mild to moderate disease. Three can cause more serious, even fatal, disease. SARS coronavirus (SARS-CoV) emerged in November 2002 and caused severe acute respiratory syndrome (SARS). That virus disappeared by 2004. Middle East respiratory syndrome (MERS) is caused by the MERS coronavirus (MERS-CoV). Transmitted from an animal reservoir in camels, MERS was identified in September 2012 and continues to cause sporadic and localized outbreaks. The third novel coronavirus to emerge in this century is called SARS-CoV-2. It causes coronavirus disease 2019 (COVID-19), which emerged from China in December 2019 and was declared a global pandemic by the World Health Organization on Mar. 11, 2020. (niaid.nih.gov/diseases-conditions/coronaviruses)

Most people infected with the SARS-CoV-2 virus will experience mild to moderate respiratory illness and recover without requiring special treatment. Older people, and those with underlying medical problems like cardiovascular disease, diabetes, chronic respiratory disease, and cancer are more likely to develop serious illness. At this time, there are no specific vaccines or treatments for COVID-19. (who.int/health-topics/coronavirus #tab=tab_1)

Because they are given to large numbers of healthy people, vaccines usually have a higher bar for safety than do drugs administered to people who are already ill. With SARS-CoV-2 (COVID-19) vaccines, researchers' main safety concern is to avoid a phenomenon called disease enhancement, in which vaccinated people who do get infected develop a more severe form of the disease than people who have never been vaccinated. In studies of an experimental SARS vaccine reported in 2004, vaccinated ferrets developed damaging inflammation in their livers after being infected with the virus.

Antibody-dependent enhancement (ADE) is a mechanism by which some viruses such as dengue virus, feline coronavirus, and HIV, as an alternative strategy, can infect host cells that display Fc receptors and thereby take advantage of anti-viral humoral immune responses. Whether ADE occurs in SARS-Coronavirus infections is controversial, but it has been reported that antibodies against the spike protein of SARS-Coronavirus may cause ADE effect.

Peter Hotez, a vaccine scientist at Baylor College of Medicine in Houston, Texas, thinks potential vaccines should be tested in animals first to rule out disease enhancement, before trials move on to humans. He says he understands the reasoning for pushing SARS-CoV-2 (COVID-19) vaccines to human tests quickly, but adds that, because of the possibility that a vaccine could enhance disease, "I'm not sure this is the vaccine you want to do it for". (Non-Patent Literature 1)

Thus, there is a need in the art for a safer vaccine for coronaviruses that could avoid the ADE effect.

CITATION LIST

Patent Literature 1: WO 2019/124441
Non-Patent Literature 1: Nature 579, 481 (2020)
The contents of the cited documents are herein incorporated by reference.

SUMMARY OF THE INVENTION

The present disclosure relates to novel antigenically-active proteins/polypeptides capable of inducing protection against coronaviruses while minimizing the possibility of ADE. The protein/polypeptide disclosed herein include a coronavirus structural protein fused to a signal sequence and/or a transmembrane domain. The coronavirus structural protein may be a spike(S) protein, nucleocapsid (N) protein, membrane (M) protein, a small envelope protein (E) or a combination thereof. Specific examples may include S1 and/or S2 subunit of the spike protein and especially, receptor binding domain of the S1 subunit.

In another aspect, the present disclosure relates to a novel polynucleotide encoding the above discussed novel antigenically-active proteins/polypeptides capable of inducing protection against coronaviruses.

In another aspect, the present disclosure relates to a novel alphavirus replicon that can express the above discussed antigenically-active protein/polypeptide. The alphavirus replicon includes polynucleotide such as RNA encoding alphavirus non-structural proteins nsP1, nsP2, nsP3 and nsP4 and a polynucleotide encoding the above-discussed antigenically active protein/polypeptide as a gene of interest.

In yet another aspect, the present disclosure relates to a vaccine comprising the above discussed polypeptide or polynucleotide. Especially, the present disclosure provides a vaccine comprising a polynucleotide encoding alphavirus non-structural proteins nsP1, nsP2, nsP3 and nsP4, and a polypeptide comprising a coronavirus structural protein fused to a signal sequence and/or transmembrane domain. The vaccine can be used for preventing and/or treating a subject from coronavirus infection.

In yet another aspect, the present disclosure relates to a method for immunizing, preventing or treating a subject from coronavirus infection comprising administering an effective amount of the above-discussed polynucleotide or polypeptide to the subject in need thereof.

In still another aspect, the present disclosure relates to use of the above-discussed polypeptide or polynucleotide for the manufacture of a medicament.

BRIEF DESCRIPTION OF THE DRAWINGS

FIG. 1
A construct of an alphavirus replicon.
FIG. 2
Full length VEEV TC-83 vector of the construct C including SS1-RBD-GS-IgG4-$CH_3$(linker)-GS-TM1 produced in Example 3.
FIG. 4-1-1 and FIG. 4-1-2
Antibody titer against SARS-CoV-2 Spike protein in mice sera on day 14 and day 35 immunization with the alphavirus replicon particles prepared in Example 4.
FIG. 4-2
Antibody titer against SARS-CoV-2 Spike protein in mice sera on day 14 and day 35 immunization with the alphavirus replicon particles prepared in Example 4
FIG. 5-1-1 and FIG. 5-1-2
Antibody titer against SARS-CoV-2 RBD in mice sera on day 14 and day 35 immunization with the alphavirus replicon particles prepared in Example 4.
FIG. 5-2
Antibody titer against SARS-CoV-2 RBD in mice sera on day 14 and day 35 immunization with the alphavirus replicon particles prepared in Example 4.
FIG. 7-1 and FIG. 7-2
Antibody titer against SARS-CoV-2 S1 protein in mice sera on Day 14, 28, and 46 immunization with the alphavirus self-amplifying RNA prepared in Example 8.

DETAILED DESCRIPTION OF THE INVENTION

Figure 3:
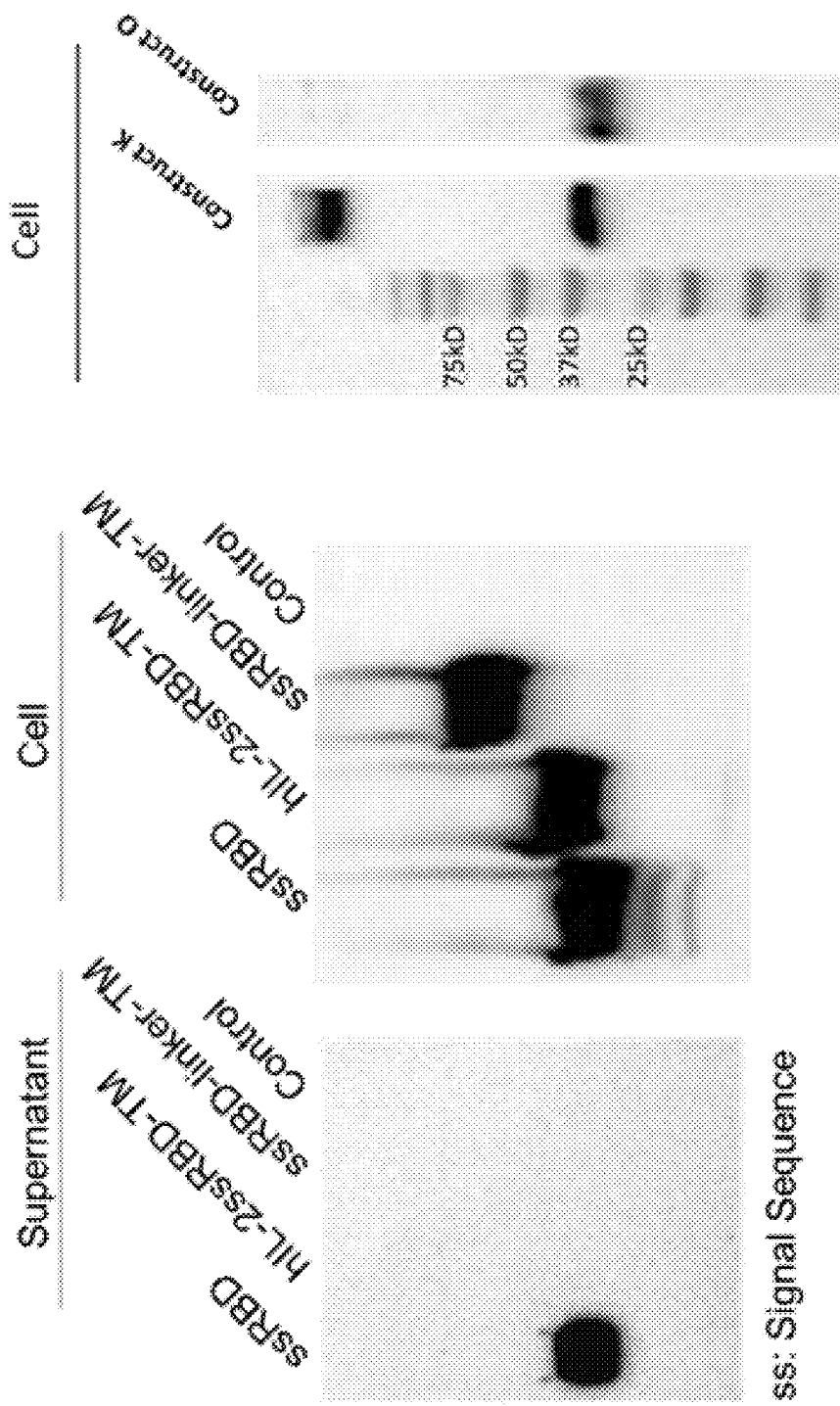
FIG. 3
Expression of RBD in HEK293T cells transfected with the alphavirus replicon plasmid vectors prepared in Example 3.

As used herein "coronavirus" is meant to refer to single-stranded, positive-sense RNA viruses that belong to the family, Coronaviridae. Exemplary Coronaviridae viruses include but are not limited to SARS-CoV, MERS-CoV and SARS-CoV-2 (COVID-19). SARS-CoV-2 (COVID-19) may include known and unknown mutants. Known mutants may include SARS-CoV-2 E484K_N501Y_K417T mutant (Brazil Strain Mutant), E484K_N501Y_K417N mutant (South African Mutant) and E484K mutant. The coronavirus genome encodes numerous non-structural proteins and four major structural proteins including the spike (S), nucleo-capsid (N), membrane (M) and small envelope (E). Spike (S) protein, a large envelope glycoprotein, is composed of S1 and S2 subunits. The "Receptor-binding domain (RBD)" is located in the S1 subunit. Preferable example of the structural protein used herein is coronavirus RBD. Spike protein, S1 and S2 subunits of the spike protein and RBD of SARS-CoV-2 and its mutants have been identified and published (Wrapp et al., Science 10.1126/science.abb2507 (2020), Z. Wang et al., (preprint) bioRxiv 2021.01.15.426911; doi: doi.org/10.1101/2021.01.15.426911).

"Coronavirus structural protein" used herein may be a naturally occurring virus structural protein or a modified protein thereof. The modified protein may be a fragment of the naturally occurring virus structural protein. In one embodiment, the modified protein has at least 70%, 75%, 80%, 85%, 90%, 95% or 98% amino acid sequence identity to a naturally occurring viral structural protein or its fragment. In one embodiment, the modified protein is a mutant where at most 10% of the amino acids are deleted, substituted, and/or added based on a naturally occurring viral envelope protein or its fragment.

As used herein, "transmembrane domain (TM)" is a protein derived either from a natural or from a synthetic source. Where the source is natural, the domain in some aspects is derived from any membrane-bound or transmembrane protein. In one aspect, the membrane-bound or transmembrane protein is a protein heterologous to SARS-CoV-2. Examples of the membrane-bound or transmembrane proteins may include the alpha, beta or zeta chain of a T-cell receptor, CD28, CD3 epsilon, CD45, CD4, CD5, CDS, CD9, CD16, CD22, CD33, CD37, CD64, CD80, CD86, CD134, CD137, CD154; toll-like receptors (TLR) such as TLR1-TLR10 in human and TLR1-TLR9, TLR11-TLR13 in mouse; interleukin (IL) receptors such as IL-1-28 receptor, RANTES receptors (CCR1, CCR3, CCR5), MIP-1 receptor, PF4 receptor, M-CSF receptor and NAP-2 receptor belonging to GPCR chemokine receptor; hemagglutinin (HA). In another aspect, the membrane-bound or transmembrane protein is a protein derived from SARS-CoV-2, such as SARS-CoV-2 spike protein.

Examples of Transmembrane Proteins May Also Include the Followings:

5-Lipoxygenase-Activating Protein, ABC Transporters, ACBP, Amyloid beta (A4), Bcl-2 Inhibitors, BNIPs, CAAX protease, Cytochromes P450, E-NPPs, EPHA1, EPHA2, EPHA3, EPHA4, Fatty Acid Desaturases, Gamma secretase, Glucose transporter, Glycophorins, GPCR, HER2/ErbB2, HER3/ErbB3, HER4/ErbB4, HSD-110, Hypoxia-induced Proteins, Immunoglobulins, Insulin receptor, Integrins, Ion channel, MAPEG, MFS, MinK Family, MPPs, Peptidase AD, Peptidase Family M48, Peptidase MA, Protein Jagged, Receptor-type Kinases, SNARE Complex, Sulfatases, TNF receptor, Transmembrane Proteins 14, Transporter, TROBP, VEGF receptors, Aldehyde Dehydrogenases, Ammonia and Urea transporters, FMN-linked Oxidoreductases, Leucine Rich Repeat (LRR)-Containing Transmembrane Proteins, Leukotriene C4 synthase, Lysosome-associated membrane glycoprotein, Major Intrinsic Protein (MIP)/FNT superfamily, Microsomal prostaglandin E synthase, N-(deoxy)ribosyltransferase-like Membrane Proteins, Neutral/alkaline Ceramidases, Oligosaccharyl Transferase, Pentameric Ligand-gated Ion Channels, Rhodopsin-like receptors and pumps, Single-helix ATPase Regulators, Squalene/phytoene Synthase, Stearoyl-CoA desaturase 1, Stannin (SNN) Membrane Proteins, T-cell Surface Glycoprotein CD3 Zeta Chain, Tetratricopeptide repeat (TPR) Alpha-Helical Repeat Proteins, Transmembrane Proteins with NAD(P)-binding Rossmann-fold Domains.

In addition, monotypic/peripheral proteins that attached to the lipid bilayer or other integral proteins and peptide may also be used as transmembrane proteins. Examples may include Alpha/Beta-Hydrolase, Annexins, Bet V1-Like Protein, C1 Domain-Containing Protein, C2 Domain-containing Protein, CoA-Dependent Acyltransferases, CRAL-TRIO Domain-Containing Protein, DNase I-like protein, Fibrinogen, FYVE/PHD Zinc Finger Protein, Galactose-Binding Domain-Like Protein, Glycolipid Transfer Protein, Immunoglobulin-Like Superfamily (E Set) Protein, Lipocalin, Lipoxygenase, PGBD superfamily, PH Domain-Like Protein, Phosphatidylinositol 3-/4-Kinase, PLC-like Phosphodiesterase, Phosphotyrosine Protein Phosphatases II, P-Loop Containing Nucleoside Triphosphate Hydrolase, Protein kinase superfamily, PX Domain-Containing Protein, Saposin, Synuclein and Transcriptional factor tubby.

The expression "transmembrane domain" used in the present disclosure includes at least transmembrane region(s) of the membrane-bound or transmembrane protein. In addition, the transmembrane domain may also include juxtamembrane domain (JMD) and/or cytoplasmic tail of the membrane-bound or transmembrane protein.

Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

Preferable transmembrane domain may be those derived from influenza virus hemagglutinin (HA), CD80, Toll-like receptor 4(TLR4) or SARS-CoV-2 spike protein. Specific examples may include a protein consisting of the flexible juxtamembrane region or flexible linker, the transmembrane domain and the cytoplasmic tail of Influenza virus hemagglutinin "HA (flexible-TM-Cyt)"; a protein consisting of transmembrane domain and cytoplasmic tail of human CD80; a protein consisting of transmembrane domain(TM) and Toll/interleukin-1 receptor domain (TIR), and a protein consisting of the juxtamembrane domain (JMD) and TM of SARS-CoV-2 Spike (S).

As used herein, "signal sequence" (sometimes referred to as signal peptide, targeting signal, localization signal, localization sequence, transit peptide, leader sequence or leader peptide) is a polynucleotide or polypeptide, depending on the context. Signal sequence is from about 9 to 200 nucleotides or 3-70 amino acids in length that, optionally, is incorporated at the 5' or N-terminus of the coding region or the protein. Some signal sequences are cleaved from the protein, for example by a signal peptidase after the proteins are transported to the desired site.

In some embodiments, the signal sequence of IL-2, especially human IL-2 may be employed. In another embodiments, the signal sequence of the SARS-CoV-2 spike protein may be employed.

The coronavirus structural protein, the transmembrane domain and/or the signal sequence may be directly or indirectly fused. In one embodiment, one or two linkers may intervene between them.

Also the coronavirus structural protein, the transmembrane domain and/or the signal sequence can be truncated and replaced by short linkers. In some embodiments, the coronavirus structural protein, the transmembrane domain and/or the signal sequence include one or more peptide linkers.

An example of a short linker consists of from 2 to 25 amino acids (e.g. 2, 3, 4, 5 or 6 amino acids). Usually, it is from 2 to 15 amino acids in length, such as SG, GS, SGG, GGS SGSG and TRGGS. In certain circumstances, the linker can consist of only one amino acid, such as glycine (G), serine (S) and cysteine (C).

When the coronavirus structural protein is chemically conjugated to the transmembrane domain and/or the signal sequence through a chemical cross-linker, examples of the cross-linkers include, but are not limited to, SMPH, Sulfo-MBS, Sulfo-EMCS, Sulfo-GMBS, Sulfo-SIAB, Sulfo-SMPB. Sulfo-SMCC, SVSB, and SIA. Chemical cross-linkers available on the market may also be employed.

IgG-derived substances can also be used as a linker. Examples of IgG-derived substances include IgG1 to IgG4 comprising (i) full (hinge-$CH_{12}C13$) (ii) half (hinge-$CH_3$) and (iii) short (12aa hinge only). Preferable example is IgG4-$CH_3$.

As used herein "alphavirus" is meant to refer to RNA-containing viruses that belong to the Togaviridae family of viruses. Exemplary Togaviridae viruses include but are not limited to Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands i virus, Fort Morgan Virus, Ndumu Virus, Buggy Creek Virus and Ockelbo virus.

By "alphavirus structural protein" is meant a polypeptide or fragment thereof having at least about 80% amino acid sequence identity to a naturally occurring viral capsid or envelope protein. In one embodiment, the alphavirus structural protein has at least about 85%, 90%, 95% or greater amino acid sequence identity with Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus. Semliki Forest Virus, Middleburg Virus, Chikungunya Virus (CHIKV), O'nyong-nyong Virus. Ross River Virus. Barmah Forest Virus. Getah Virus. Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, or Buggy Creek Virus, Wild type amino acid sequences of alphavirus structural proteins can be obtained from GenBank.

In specific embodiments, the alphavirus is a CHIKV, for example CHIKV strain 37997 or LR2006 OPY-1. In other embodiments, the alphavirus is a VEEV, for example VEEV strain TC-83.

By "an alphavirus replicon" is meant an RNA molecule which can direct its own amplification in vivo in a target cell. The replicon encodes the polymerase(s) which catalyze RNA amplification (nsP1, nsP2, nsP3, nsP4) and contains cis RNA sequences required for replication which are recognized and utilized by the encoded polymerase(s). An alphavirus replicon typically contains the following ordered elements: 5' UTR, sequences which encode alphavirus nonstructural proteins (nsP1, nsP2, nsP3, nsP4), 3' UTR, and a poly A signal. An alphavirus replicon also contains one or more viral sub-genomic promoters directing the expression of the gene of interest. Those sequences may have one or more mutations taught in a prior art.

The alphavirus replicon provided by the present disclosure may have the construct shown in FIG. 1.

In this disclosure, "comprises," "comprising," "containing" and "having" and the like can have the meaning ascribed to them in U.S. Patent law and can mean "includes," "including," and the like; "consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e<"3> and e<"100> indicating a closely related sequence.

By "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

A satisfactory effect can be obtained by systemic administration, e.g. intramuscular administration, subcutaneous administration or intravenous administration 1-4 times at the amount of $10^3$-$10^{11}$ Infectious Unit (IU) or 0.01-500 μg per time, preferably $10^5$-$10^{10}$ IU or 0.1-100 μg per time, for example $10^7$-$10^9$ IU or 1-50 μg per one time. The replicon may preferably be formulated in a vaccine composition suitable for administration in a conventional manner.

By "subject" is meant a mammal, including, but not limited to, a human or non-human mammal, such as a bovine, equine, canine, ovine, or feline.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Unless specifically stated or obvious from context, as used herein, the term "or" is understood to be inclusive.

Unless specifically stated or obvious from context, as used herein, the terms "a", "an", and "the" are understood to be singular or plural.

The art will acknowledge that polynucleotide sequences described in the specification and claims will recite "T"s in a representative DNA sequence but where the sequence represents RNA, the "T"s would be substituted for "U"s.

Any vaccine compositions or methods provided herein can be combined with one or more of any of the other vaccine compositions and methods provided herein.

The term "vector" refers to the means by which a nucleic acid sequence can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Typically, the nucleic acid molecule to be expressed is "operably linked" to a promoter and/or enhancer, and is subject to transcription regulatory control by the promoter and/or enhancer.

The method of transfection and the choice of expression vehicle will depend on the host system selected. Transfection methods are described, e.g., in Ausubel et al. (supra); expression vehicles may be chosen from those provided, e.g., in Cloning Vectors: A Laboratory Manual (P. H. Pouwels et al., 1985, Supp. 1987) The references cited in this paragraph are herein incorporated by reference.

A variety of expression systems exist for the production of the constructs of the invention. Expression vectors useful for producing the constructs include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as alphavirus (e.g. Chikungunya Virus (CHIKV) and Venezuelan Equine Encephalitis Virus (VEEV)), baculoviruses, papova viruses, such as SV40, vaccinia viruses, adenoviruses, fowl pox viruses, pseudorabies viruses and retroviruses, and vectors derived from combinations thereof.

Constructs and/or vectors used herein comprise alphavirus polynucleotides encoding nonstructural proteins nsP1, nsP2, nsP3 and nsP4 and a gene of interest encoding a polypeptide comprising a coronavirus structural protein fused to a signal sequence and/or a transmembrane domain as discussed above. Specific example of the construct or vector is that shown in FIG. 1.

The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRITS. Among preferred eukaryotic vectors are pFastBacl pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, can express viral proteins, including those described herein, into eukaryotic cells and/or prokaryotic cells. Thus, in one embodiment, the present disclosure provides host cells which comprise a vector (or vectors) that contain nucleic acids which encode alphavirus structural proteins, including capsid, E3, E2, 6K, and El or portions thereof, and a vector that comprises nucleic acids which encode alphavirus nsP1, nsP2, nsP3 and nsP4, and at least one of coronavirus gene of interest under conditions which allow the formation of alphavirus replicon particle.

In one embodiment, said vector is a recombinant baculovirus. In another embodiment, said recombinant baculovirus is transfected into an insect cell. In a preferred embodiment, said cell is an insect cell. In another embodiment, said insect cell is a Sf9 cell.

One particular bacterial expression system for polypeptide production is the *E. coli* pET expression system (Novagen, Inc., Madison, Wis). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved by using host strains that express T7 RNA polymerase in response to IPTG induction. Once produced, a recombinant polypeptide is then isolated according to standard methods known in the art, for example, those described herein.

Depending on the vectors and host cells selected, the constructs are produced by growing host cells transfected by the vectors under conditions whereby the recombinant proteins are expressed and the alphavirus replicon is generated, and constructs containing alphavirus replicon being packaged with the particle of alphavirus structural proteins are formed. In one embodiment, the invention comprises a method of producing a construct, that involves co-transfecting a vector comprising a polynucleotide encoding alphavirus non-structural protein nsP1, nsP2, nsP3 and nsP4, and at least one gene of interest encoding the polypeptide comprising a coronavirus structural protein fused to a signal sequence and/or transmembrane domain, and at least one vector each encoding at least one alphavirus structural protein into suitable host cells and expressing said alphavirus structural protein under conditions that allow construct formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells that produce alphavirus replicon particles of the invention include, but are not limited to, batch, batch-fed, continuous and perfusion cell culture techniques. In one embodiment, cells co-transfected with a vector encoding an alphavirus replicon and a vector comprising a polypeptide encoding capsid, and a vector comprising a polynucleotide encoding envelope proteins, such as those derived from a CHIKV or VEEV are grown in a bioreactor or fermentation chamber where cells propagate and express protein (e.g., recombinant proteins) for purification and isolation.

Typically, cell culture is performed under sterile, controlled temperature and atmospheric conditions. A bioreactor is a chamber used to culture cells in which environmental conditions such as temperature, atmosphere, agitation and/or pH can be monitored. In one embodiment, the bioreactor is a stainless steel chamber. In another embodiment, said bioreactor is a pre-sterilized plastic bag (e.g., Cellbag.RTM, Wave Biotech, Bridgewater, N.J., the contents of the cited document is herein incorporated by reference). In other embodiment, said pre-sterilized plastic bags are about 10 L to 1000 L bags.

In another embodiment, an RNA molecule such as an alphavirus replicon may be generated by conventional procedures known to the art from a template DNA sequence. In vitro transcription (IVT) methods permit template-directed synthesis of RNA molecules. IVT methods permit synthesis of large quantities of RNA transcript. Generally, IVT utilizes a DNA template comprising a promoter sequence upstream of a sequence of interest. The promoter sequence is most commonly of bacteriophage origin such as the T7, T3 or SP6 promoter sequence but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand. Kits for in vitro transcription such as T7 transcription kit (RiboMax™ Express Large Scale RNA production System, Promega (WI USA)).

As used herein, the term "pharmaceutically acceptable carrier" means one or more compatible solid or liquid fillers, diluents or encapsulating substances which are suitable for administration to a human or other vertebrate animal, including any and all aqueous solvents (e.g., water, alcoholic/aqueous solutions, saline solutions, parenteral vehicles, such as sodium chloride, and Ringer's dextrose), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a vaccine composition are adjusted according to well-known parameters.

Encapsulating substances refers to a delivery vehicle where the polynucleotide or vector is packaged, such as a replicon particle (e.g. the alphavirus replicon particle described in US patent publication No. 2019-0185822, the contents of the document is incorporated by reference) and a lipid delivery system (e.g. liposome).

In some embodiments, the vaccine compositions or formulations of the present disclosure comprise a lipid delivery system, e.g., a liposome, a lipoplexes, a lipid nanoparticle, or any combination thereof. The polynucleotides such as an alpha virus replicon described herein can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that may primarily be composed of a lipid bilayer and may be used as a delivery vehicle for the administration of pharmaceutical formulations. Liposomes can be of different sizes. A multilamellar vesicle (MLV) may be hundreds of nanometers in diameter, and may contain a series of concentric bilayers separated by narrow aqueous compartments. A small unicellular vesicle (SUV) may be smaller than 50 nm in diameter, and a large unilamellar vesicle (LUV) may be between 50 and 500 nm in diameter. Liposome design may include, but is not limited to, opsonins or ligands to improve the attachment of liposomes to unhealthy tissue or to activate events such as, but not limited to, endocytosis. Liposomes may contain a low or a high pH value in order to improve the delivery of the pharmaceutical formulations.

The formation of liposomes may depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

In some embodiments, the polynucleotides such as alpha virus replicon described herein may be encapsulated by the liposome and/or it may be contained in an aqueous core that may then be encapsulated by the liposome.

In some embodiments, the polynucleotides such as alpha virus replicon described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed.

In some embodiments, the polynucleotides such as alpha virus replicon described herein can be formulated in a lipid-polycation complex. As a non-limiting example, the polycation can include a cationic peptide or a polypeptide such as, but not limited to, polylysine, polyornithine and/or polyarginine and the cationic peptides.

In some embodiments, the polynucleotides such as alpha virus replicon described herein can be formulated in a lipid nanoparticle (LNP).

Lipid nanoparticle formulations typically comprise one or more lipids. In some embodiments, the lipid is a cationic or an ionizable lipid. In some embodiments, lipid nanoparticle formulations further comprise other components, including a phospholipid, a structural lipid, a quatemary amine compound, and a molecule capable of reducing particle aggregation, for example a PEG or PEG-modified lipid. In some embodiments, the amount of the cationic and ionizable lipids in the lipid composition ranges from about 0.01 mol % to about 99 mol %.

LNPs contain a pH-sensitive ionizable cationic lipid that attract anionic nucleic acids to form the core of self-assembling nanoparticle to ensure high encapsulation. At physiological pH, LNPs are neutral, eliminating a mechanism of toxicity seen with permanently cationic molecules.

These same pH-sensitive lipids are responsible for responding to the acidic environment of the endosome and triggering the disruption of the endosome and release of the nucleic acid into the cell.

This replicon based vaccine technology is a unique platform technology for the vaccination as a RNA can self-amplify to produce the vaccine antigen and deliver into the cellular organ. Moreover, this replicon based vaccine technology overcomes the challenges commonly associated with DNA based vaccines, such as risk of genome integration or the high doses and devices needed for administration, e.g. electroporation, and expects the higher immunogenicity with minimum dose based on the self-replication system over the mRNA technology.

According to the present invention, novel antigenically-active proteins/polypeptides are also useful for producing antibodies for diagnosis and protecting against coronaviruses while minimizing the possibility of ADE. The proteins/polypeptides disclosed herein include minimum sequences encoding the coronavirus RBD fused to a signal sequence and/or to a transmembrane domain (TMD) sequence, intended to maximize immunogenicity and minimize ADE.

The invention will be described in detail with reference to the following examples, which, however, are not intended to limit the scope of the present application.

EXAMPLES

Example 1

Each gene encoding shown below construct 1-8 was synthesized by Integrated DNA Technologies, Inc. (idtdna.com/pages).

1. Construct of SARS-CoV-2-RBD Sequence Fused to hIL-2 Signal Sequence and HA (Flexible Domain-Transmembrane (TM)-Cytoplasmic Tail(Cyt))

```
Construct 1
[hIL-2 signal sequence]  [COVID-19-RBD]  [HA (flexible-TM-Cyt)]
                                                   (SEQ ID NO: 1)
MYRMQLLSCIALSLALVTNSVRFPNITNLCPFGEVFNATRFASVYAWNRKRISNCVADY

SVLYNSASFSTFKCYGVSPTKLNDLCFTNVYADSFVIRGDEVRQIAPGQTGKIADYNYK

LPDDFTGCVIAWNSNNLDSKVGGNYNYLYRLFRKSNLKPFERDISTEIYQAGSTPCNGV

EGFNCYFPLQSYGFQPTNGVGYQPYRVVVLSFELLHAPATVCGPKKSGVKLESMGIYQI

LAIYSTVASSLVLLVSLGAISFWMCSNGSLQCRICI hIL-2 signal sequence:
                                                   (SEQ ID NO: 2)
MYRMQLLSCIALSLALVTNS COVID19-RBD:
                                                   (SEQ ID NO: 3)
VRFPNITNLCPFGEVFNATRFASVYAWNRKRISNCVADYSVLYNSASFSTFKCYGVSPT

KLNDLCFTNVYADSFVIRGDEVRQIAPGQTGKIADYNYKLPDDFTGCVIAWNSNNLDSK

VGGNYNYLYRLFRKSNLKPFERDISTEIYQAGSTPCNGVEGFNCYFPLQSYGFQPTNGV

GYQPYRVVVLSFELLHAPATVCGPKKS

HA (flexible-TM-Cyt):
                                                   (SEQ ID NO: 4)
GVKLESMGIYQILAIYSTVASSLVLLVSLGAISFWMCSNGSLQCRICI hIL-2: human Interleukin-2
HA (flexilble-TM-Cyt): polypeptide of Influenza virus
```

2. Construct of SARS-CoV-2-RBD Sequence Fused to hIL-2 Signal Sequence and HA (Flexible-TM-Cyt)

```
Construct 2
[hIL-2 signal sequence] C [COVID-19-RBD] C [HA (flexible-TM-Cyt)]
                                                   (SEQ ID NO: 5)
MYRMQLLSCIALSLALVTNSCVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNY

KLPDDFTGCVIAWNSNNLDSKVGGNYNYLYRLFRKSNLKPFERDISTEIYQAGSTPCNG

VEGFNCYFPLQSYGFQPTNGVGYQPYRVVVLSFELLHAPATVCGPKKSCGVKLESMGIY

QILAIYSTVASSLVLLVSLGAISFWMCSNGSLQCRICI

"C" in the schematic chart: linker (Cysteine)
Linkers in the amino acid sequence are underlined.
```

3. Construct of SARS-CoV-2-RBD Sequence Fused to hIL-2 Signal Sequence and HA (Flexible-TM-Cyt) with Linker

```
Construct 3
[hIL-2 signal sequence] [COVID-19-RBD] GS [human IgG4CH3] GS [HA (flexible-TM-Cyt)]
```

(SEQ ID NO: 6)

MYRMQLLSCIALSLALVTNSVRFPNITNLCPFGEVFNATRFASVYAWNRKRISNCVADY

SVLYNSASFSTFKCYGVSPTKLNDLCFTNVYADSFVIRGDEVRQTAPGQTGKIADYNYK

LPDDFTGCVIAWNSNNLDSKVGGNYNYLYRLFRKSNLKPFERDISTEIYQAGSTPCNGV

EGFNCYFPLQSYGFQPTNGVGYQPYRVVVLSFELLHAPATVCGPKKSGSGQPREPQVYT

LPPSQEEMTKNQVSLTCLVKGFYPSDIAVEWESNGQPENNYKTTPPVLDSDGSFFLYSR

LTVDKSRWQEGNVFSCSVMHEALHNHYTQKSLSLSLGKGSGVKLESMGIYQILAIYSTV

ASSLVLLVSLGAISFWMCSNGSLQCRICI

```
"GS" in the schematic chart: linker (GGATCC)
linkers are underlined in the amino acid sequence human IgG4 CH3:
```
(SEQ ID NO: 7)

GQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

4. Construct of SARS-CoV-2-RBD Sequence Fused to hIL-2 Signal Sequence and HA (Flexible-TM-Cyt) with Linker

```
Construct 4
[hIL-2 signal sequence] C [COVID-19-RBD] C GS [human IgG4CH3] GS [HA (flexible-TM-Cyt)]
```

(SEQ ID NO: 8)

MYRMQLLSCIALSLALVTNSCVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNY

KLPDDFTGCVIAWNSNNLDSKVGGNYNYLYRLFRKSNLKPFERDISTEIYQAGSTPCNG

VEGFNCYFPLQSYGFQPTNGVGYQPYRVVVLSFELLHAPATVCGPKKSCGSGQPREPQV

YTLPPSQEEMTKNQVSLTCLVKGFYPSDIAVEWESNGQPENNYKTTPPVLDSDGSFFLY

SRLTVDKSRWQEGNVFSCSVMHEALHNHYTQKSLSLSLGKGSGVKLESMGIYQILAIYS

TVASSLVLLVSLGAISFWMCSNGSLQCRICI

```
"C" "CGS" and "GS" in the schematic chart: linker
Linkers are underlined in the amino acid sequence.
```

5. Construct of SARS-CoV-2-RBD Sequence Fused to hIL-2 Signal Sequence and Human TLR4(TM-Toll/Interleukin-1 Receptor Domain (TIR))

```
Construct 5
[hIL-2 signal sequence] [COVID-19-RBD] GS [Human TLR4(TM-TIR)]
```

(SEQ ID NO: 9)

MYRMQLLSCIALSLALVTNSVRFPNITNLCPFGEVFNATRFASVYAWNRKRISNCVADY

SVLYNSASFSTFKCYGVSPTKLNDLCFTNVYADSFVIRGDEVRQIAPGQTGKIADYNYK

LPDDFTGCVIAWNSNNLDSKVGGNYNYLYRLFRKSNLKPFERDISTEIYQAGSTPCNGV

EGFNCYFPLQSYGFQPTNGVGYQPYRVVVLSFELLHAPATVCGPKKSGSKTIIGVSVLS

VLVVSVVAVLVYKFYFHLMLLAGCIKYGRGENIYDAFVIYSSQDEDWVRNELVKNLEEG

VPPFQLCLHYRDFIPGVAIAANIIHEGFHKSRKVIVVVSQHFIQSRWCIFEYEIAQTWQ

FLSSRAGIIFIVLQKVEKTLLRQQVELYRLLSRNTYLEWEDSVLGRHIFWRRLRKALLD

GKSWNPEGTVGTGCNWQEATSI human TLR4(TM-TIR):
(SEQ ID NO: 10)
KTIIGVSVLSVLVVSVVAVLVYKFYFHLMLLAGCIKYGRGENIYDAFVIYSSQDEDWVR

NELVKNLEEGVPPFQLCLHYRDFIPGVAIAANIIHEGFHKSRKVIVVVSQHFIQSRWCI

FEYEIAQTWQFLSSRAGIIFIVLQKVEKTLLRQQVELYRLLSRNTYLEWEDSVLGRHIF

WRRLRKALLDGKSWNPEGTVGTGCNWQEATSI

6. Construct of SARS-CoV-2-RBD Gene Sequence Fused to hIL-2 Signal Sequence and Human TLR4(TM-TIR)

Construct 6

| hIL-2 signal sequence | C | COVID-19-RBD | CGS | Human TLR4(TM-TIR) |

(SEQ ID NO: 11)
MYRMQLLSCIALSLALVTNS<u>C</u>VRFPNITNLCPFGEVFNATRFASVYAWNRKRISNCVAD

YSVLYNSASFSTFKCYGVSPTKLNDLCFTNVYADSFVIRGDEVRQIAPGQTGKIADYNY

KLPDDFTGCVIAWNSNNLDSKVGGNYNYLYRLFRKSNLKPFERDISTEIYQAGSTPCNG

VEGFNCYFPLQSYGFQPTNGVGYQPYRVVVLSFELLHAPATVCGPKKS<u>CGS</u>KTIIGVSV

LSVLVVSVVAVLVYKFYFHLMLLAGCIKYGRGENIYDAFVIYSSQDEDWVRNELVKNLE

EGVPPFQLCLHYRDFIPGVAIAANIIHEGFHKSRKVIVVVSQHFIQSRWCIFEYEIAQT

WQFLSSRAGIIFIVLQKVEKTLLRQQVELYRLLSRNTYLEWEDSVLGRHIFWRRLRKAL

LDGKSWNPEGTVGTGCNWQEATSI

"C" and "CGS" in the schematic chart: linkers
Linkers are underlined in the amino acid sequence.

7. Construct of SARS-CoV-2-RBD Sequence Fused to hIL-2 Signal Sequence and Human TLR4(TM-TIR) with Linker Construct 7

| hIL-2 signal sequence | COVID-19-RBD | GS | human IgG4CH3 | GS | Human TLR4(TM-TIR) |

(SEQ ID NO: 12)
MYRMQLLSCIALSLALVTNSVRFPNITNLCPFGEVFNATRFASVYAWNRKRISNCVADY

SVLYNSASFSTFKCYGVSPTKLNDLCFTNVYADSFVIRGDEVRQIAPGQTGKIADYNYK

LPDDFTGCVIAWNSNNLDSKVGGNYNYLYRLFRKSNLKPFERDISTEIYQAGSTPCNGV

EGFNCYFPLQSYGFQPTNGVGYQPYRVVVLSFELLHAPATVCGPKKS<u>GS</u>GQPREPQVYT

LPPSQEEMTKNQVSLTCLVKGFYPSDIAVEWESNGQPENNYKTTPPVLDSDGSFFLYSR

LTVDKSRWQEGNVFSCSVMHEALHNHYTQKSLSLSLGK<u>GS</u>KTIIGVSVLSVLVVSVVAV

LVYKFYFHLMLLAGCIKYGRGENIYDAFVIYSSQDEDWVRNELVKNLEEGVPPFQLCLH

YRDFIPGVAIAANIIHEGFHKSRKVIVVVSQHFIQSRWCIFEYEIAQTWQFLSSRAGII

FIVLQKVEKTLLRQQVELYRLLSRNTYLEWEDSVLGRHIFWRRLRKALLDGKSWNPEGT

VGTGCNWQEATSI

"GS" in the schematic chart: linker
Linkers are underlined in the amino acid sequence.

8. Construct of COVID19 RBD Sequence Fused to hIL-2 Signal Sequence and Human TLR4(TM-TIR) with Linker

```
Construct 8
[hIL-2 signal sequence] C [COVID19-RBD] C GS [human IgG4CH3] GS [Human TLR4(TM-TIR)]

(SEQ ID NO: 13)
MYRMQLLSCIALSLALVTNSCVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNY

KLPDDFTGCVIAWNSNNLDSKVGGNYNYLYRLFRKSNLKPFERDISTEIYQAGSTPCNG

VEGFNCYFPLQSYGFQPTNGVGYQPYRVVVLSFELLHAPATVCGPKKSCGSGQPREPQV

YTLPPSQEEMTKNQVSLTCLVKGFYPSDIAVEWESNGQPENNYKTTPPVLDSDGSFFLY

SRLTVDKSRWQEGNVFSCSVMHEALHNHYTQKSLSLSLGKGSKTIIGVSVLSVLVVSVV

AVLVYKFYFHLMLLAGCIKYGRGENIYDAFVIYSSQDEDWVRNELVKNLEEGVPPFQLC

LHYRDFIPGVAIAANIIHEGFHKSRKVIVVVSQHFIQSRWCIFEYEIAQTWQFLSSRAG

IIFIVLQKVEKTLLRQQVELYRLLSRNTYLEWEDSVLGRHIFWRRLRKALLDGKSWNPE

GTVGTGCNWQEATSI

"C, "CGS" and "GS" in the schematic chart: linker
Linkers are underlined in the amino acid sequence.
```

Information regarding hIL-2 signal sequence, COVID19-RBD, human IgG4 $CH_3$ and HA(flexible-TM-Cyt) are also available from the National Center for Biotechnology Information website and from UniProt website.

hIL-2 signal sequence
- ncbi.nlm.nih.gov/protein/P60568
- UniProtKB/Swiss-Prot: P60568.1

COVID19-RBD
- ncbi.nlm.nih.gov/nuccore/NC_045512
- NCBI Reference Sequence: NC_045512.2

HA(flexible-TM-Cyt)
- ncbi.nlm.nih.gov/protein/P03452
- UniProtKB/Swiss-Prot: P03452.2

Human IgG4
- uniprot.org/uniprot/P01861
- UniProtKB: P01861

Example 2

Each gene encoding shown below construct A-O was synthesized by Integrated DNA Technologies, Inc. (idtdna.com/pages).

[Signal sequence]–[COVID-19-RBD]–GS–[Linker]–GS–[Transmembrane domain]

Construct A: SS1-RBD1(330-521) (SEQ ID NO: 37)
Construct B: SS2-RBD1(330-521)-TM2 (SEQ ID NO: 38)
Construct C: SS1-RBD1(330-521)-GS-Linker-GS-TM1 (SEQ ID NO: 39)
Construct D: SS1-RBD1(330-521)-GS-Linker-GS-TM2 (SEQ ID NO: 40)
Construct E: SS1-RBD2(330-530)-GS-Linker-GS-TM1 (SEQ ID NO: 41)
Construct F: SS1-RBD2(330-530)-GS-Linker-GS-TM2 (SEQ ID NO: 42)
Construct G: SS2-RBD1(330-521)-GS-Linker-GS-TM1 (SEQ ID NO: 43)
Construct H: SS2-RBD1(330-521)-GS-Linker-GS-TM2 (SEQ ID NO: 44)
Construct I: SS2-RBD2(330-530)-GS-Linker-GS-TM1 (SEQ ID NO: 45)
Construct J: SS2-RBD2(330-530)-GS-Linker-GS-TM2 (SEQ ID NO: 46)
Construct K: SS3-RBD3(327-531)-TM2 (SEQ ID NO: 47)
Construct L: SS1-RBD2(330-521)-TM2 (SEQ ID NO: 48)
Construct M: SS1-RBD3(327-531)-C-TM3 (SEQ ID NO: 49)
Construct N: SS3-RBD3(327-531)-TM3 (SEQ ID NO: 50)
Construct O: SS3-RBD1(330-521)-TM3 (SEQ ID NO: 51)

```
Signal sequence
SS1: SARS-CoV-2 signal sequence (1-15):
                                        (SEQ ID NO: 14)
MFVFLVLLPLVSSQC SS2: hIL-2 signal sequence:
                                        (SEQ ID NO: 15)
MYRMQLLSCIALSLALVTNS SS3: SARS-CoV-2 signal sequence (1-13):
                                        (SEQ ID NO: 16)
MFVFLVLLPLVSS
```

SARS-CoV-2-RBDs
RBD1: SARS-CoV-2 RBD amino acid position 330 and 521

RBD2: SARS-CoV-2 RBD amino acid position 330 and 530

RBD3: SARS-CoV-2 RBD amino acid position 327 and 531

RBD1:
(SEQ ID NO: 17)
PNITNLCPFGEVFNATRFASVYAWNRKRISNCVADYSVLYNSASFSTFKC

YGVSPTKLNDLCFTNVYADSFVIRGDEVRQIAPGQTGKIADYNYKLPDDF

TGCVIAWNSNNLDSKVGGNYNYLYRLFRKSNLKPFERDISTEIYQAGSTP

CNGVEGFNCYFPLQSYGFQPTNGVGYQPYRVVVLSFELLHAP

RBD2:
(SEQ ID NO: 18)
PNITNLCPFGEVFNATRFASVYAWNRKRISNCVADYSVLYNSASFSTFKC

YGVSPTKLNDLCFTNVYADSEVIRGDEVRQIAPGQTGKIADYNYKLPDDF

IGCVIAWNSNNLDSKVGGNYNYLYRLFRKSNLKPFERDISTEIYQAGSTP

CNGVEGFNCYFPLQSYGFQPTNGVGYQPYRVVVLSFELLHAPATVCGPKK

S

RBD3:
(SEQ ID NO: 19)
VRFPNITNLCPFGEVFNATRFASVYAWNRKRISNCVADYSVLYNSASFST

FKCYGVSPTKLNDLCFTNVYADSFVIRGDEVRQIAPGQTGKIADYNYKLP

DDFTGCVIAWNSNNLDSKVGGNYNYLYRLFRKSNLKPFERDISTEIYQAG

STPCNGVEGFNCYFPLQSYGFQPTNGVGYQPYRVVVLSFELLHAPATVCG

PKKST

Linker
Human IgG4-CH3
(SEQ ID NO: 20)
GQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKS

LSLSLGK

Transmembrane-Cytoplasm (TM-Cyt)
TM1: Human CD80* (TM-Cyt):
(SEQ ID NO: 21)
LLPSWAIT LISVNGIFVI CCLTYCFAPR CRERRRNERL RRESVRPV
*CD80: ncbi.nlm.nih.gov/protein/
NP_005182

TM2: HA(flexible-TM-Cyt):
(SEQ ID NO: 22)
GVKLESMGIYQILAIYSTVASSLVLLVSLGAISFWMCSNGSLQCRICI TM3: COVID19 (JMD-TM):
(SEQ ID NO: 23)
GKYEQYIKWPWYIWLGFIAGLIAIVMVTIMLCCMTSCCSCLKGCCSCGSC

CKFDEDDSEPVLKGVKLHYT

The juxtamembrane domain (JMD) of spike protein is an aromatic amino acid-rich region proximal to the transmembrane domain that is highly conserved in all coronaviruses (Howard et al., JOURNAL OF VIROLOGY, March 2008, p. 2883-2894 Vol. 82, No. 6, the contents of the reference is herein incorporated by reference).

JMD:
(SEQ ID NO: 24)
GKYEQYTKWPWYIWL

TM:
(SEQ ID NO: 25)
GFIAGLIAIVMVTIMLCCMTSCCSCLKGCCSCGSCCKFDEDDSEPVLKGV
KLHYT

Example 3

Figures 1, 7:
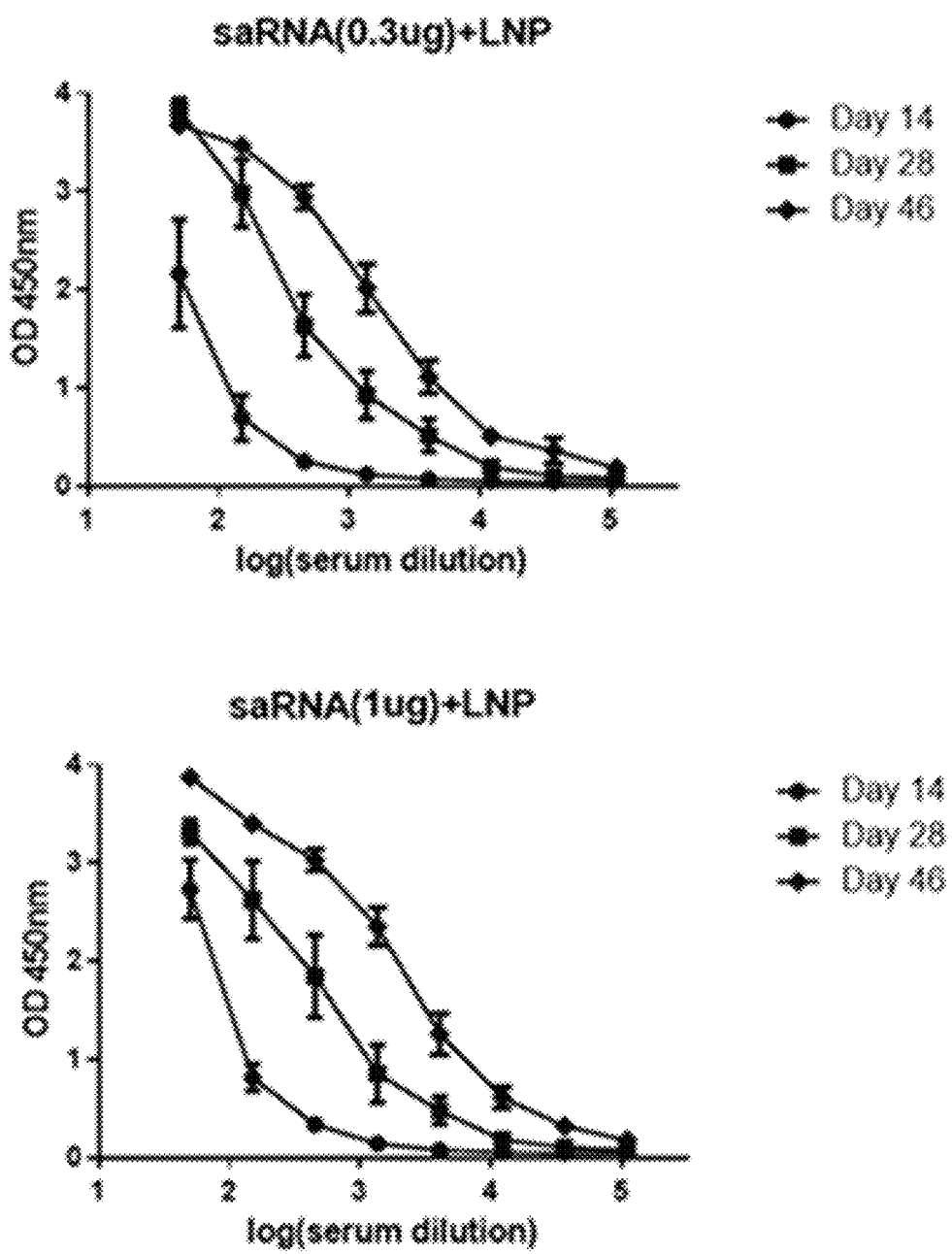
Figures 2, 7:
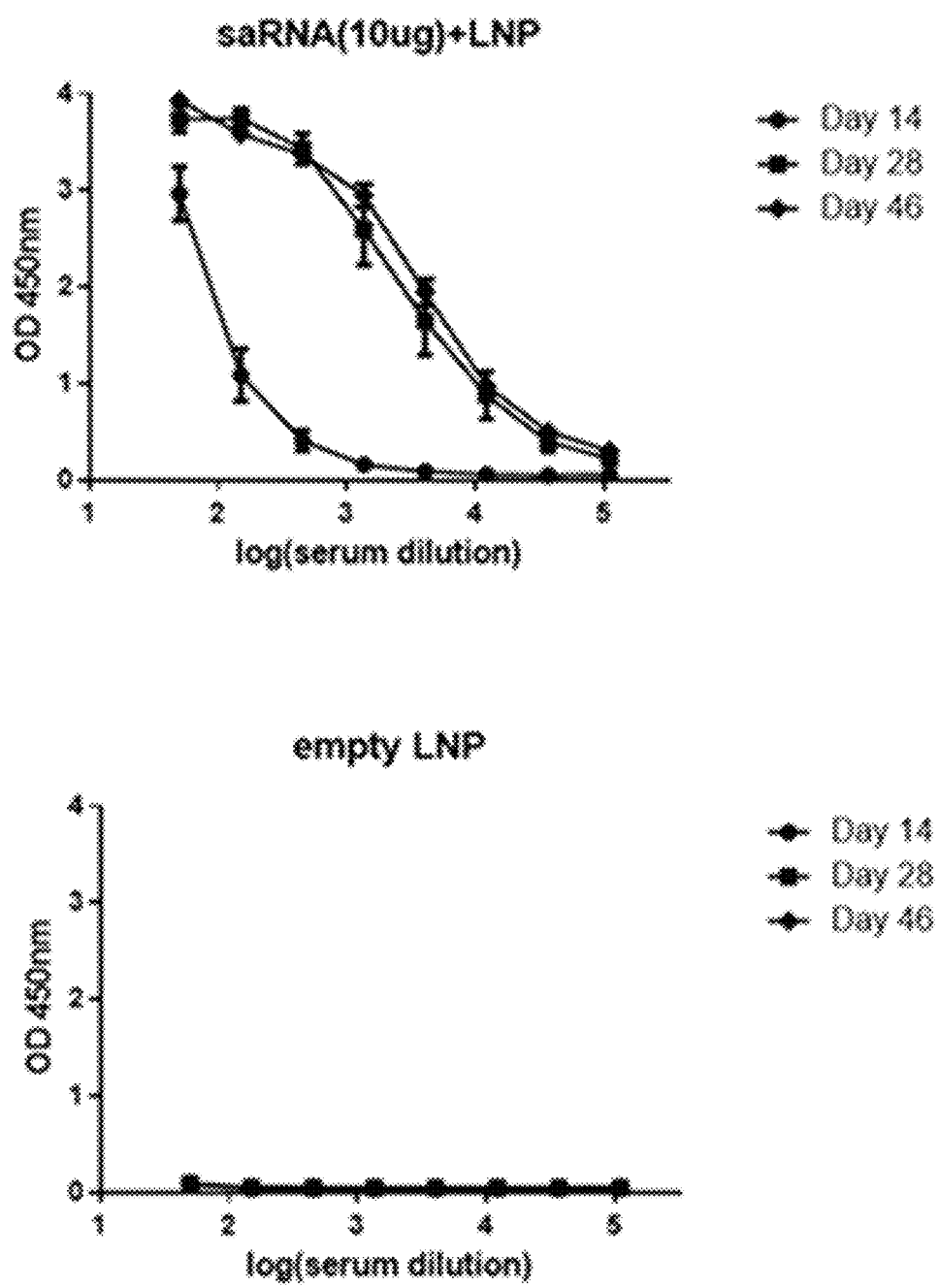

Preparation of replicon vector. Schematic construct of the alphavirus replicon is shown in FIG. 1.

Figures 2, 4:
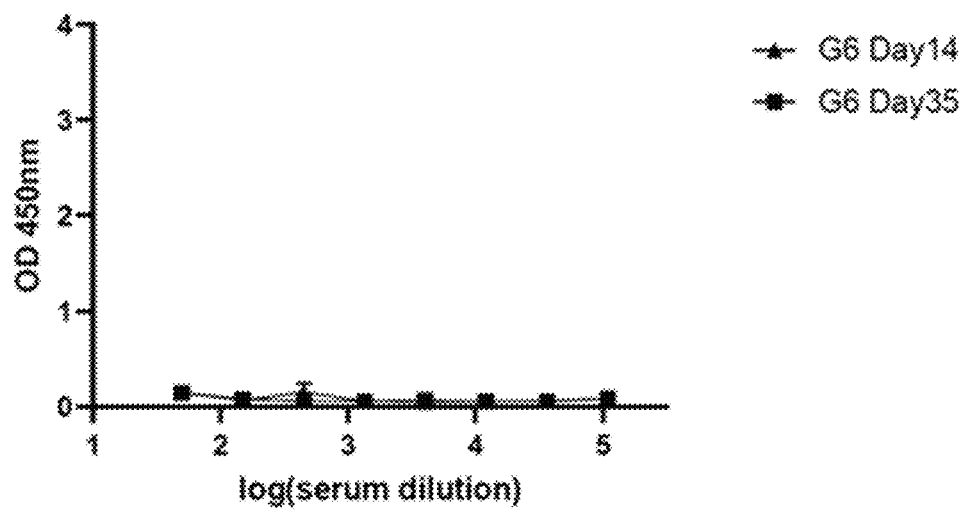
Figures 2, 5:
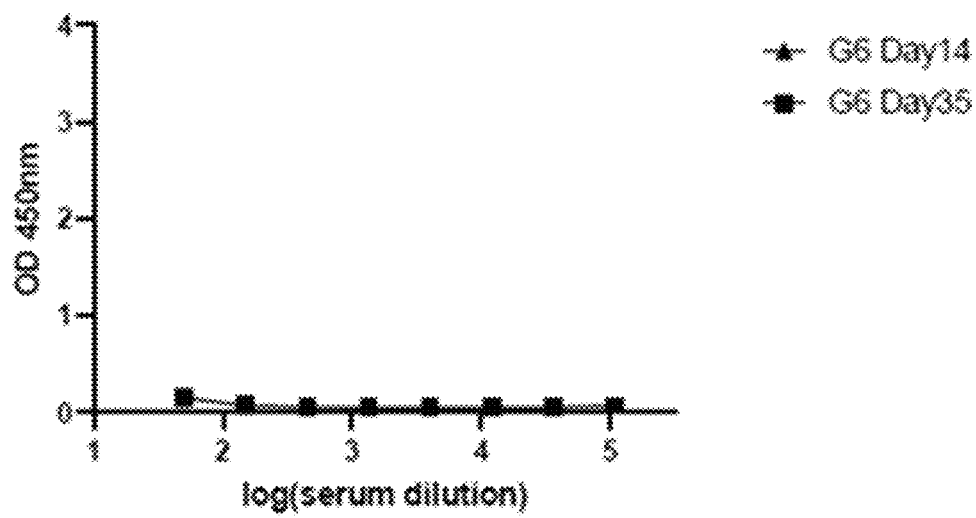

Each gene of Interest DNA prepared in Example 1 and 2 was cloned into the VEEV replicon vector under the control of the subgenomic (SG) promoter. The VEEV replicon plasmid encoding each fragment was created by insertion at AscI and SbfI restriction sites to obtain the full-length VEEV TC-83 replicon construct. One example of the full length VEEV TC-83 plasmid vector is shown in FIG. 2.

Nucleotide sequences of SG promoter, 5'UTR, 3'UTR and Poly A tail are as follows. RNA sequences were obtained by using those DNA sequences as template.

SG promoter:
(SEQ ID NO: 26)
cctgaatggactacgacatagtctagtccgccaag

5'UTR:
(SEQ ID NO: 27)
ataggcggcgcatgagagaagcccagaccaattacctacccaaa

3'UTR:
(SEQ ID NO: 28)
gcgatcgcatacagcagcaattggcaagctgcttacatagaactcgcggc
gattggcatgccgccttaaaattttttatttttattttttcttttcttttccg
aatcggattttgttttaatatttc Poly A tail:
(SEQ ID NO: 29)
aaaaaaaaaaaaaaaaaaaaaaaaaaaaaaaaaaaaaaaaaaaaa
aaaaa VEEV TC-83 Replicon nsP1-4 amino acid sequence is as follows.

(SEQ ID NO: 30)
MEKVHVDIEEDSPFLRALQRSFPQFEVEAKQVTDNDHANARAFSHLASKL

IETEVDPSDTILDIGSAPARRMYSKHKYHCICPMRCAEDPDRLYKYATKL

KKNCKEITDKELDKKMKELAAVMSDPDLETETMCLHDDESCRYEGQVAVY

QDVYAVDGPTSLYHQANKGVRVAYWIGFDTTPFMFKNLAGAYPSYSTNWA

DETVLTARNIGLCSSDVMERSRRGMSILRKKYLKPSNNVLFSVGSTIYHE

KRDLLRSWHLPSVFHLRGKQNYTCRCETIVSCDGYVVKRIAISPGLYGKP

SGYAATMHREGFLOCKVTDTLNGERVSFPVCTYVPATLCDQMTGILATDV

SADDAQKLLVGLNQRIVVNGRTQRNTNTMKNYLLPVVAQAFARWAKEYKE

DQEDERPLGLRDRQLVMGCCWAFRRHKITSIYKRPDTQTIIKVNSDFHSF

VLPRIGSNTLEIGLRTRIRKMLEEHKEPSPLITAEDIQEAKCAADEAKEV

REAEELRAALPPLAADFEEPTLEADVDLMLQEAGAGSVETPRGLIKVTSY

AGEDKIGSYAVLSPQAVLKSEKLSCIHPLAEQVIVITHSGRKGRYAVEPY

HGKVVVPEGHAIPVQDFQALSESATIVYNEREFVNRYLHHIATHGGALNT

DEEYYKTVKPSEHDGEYLYDIDRKQCVKKELVTGLGLTGELVDPPFHEFA

YESLRTRPAAPYQVPTIGVYGVPGSGKSGIIKSAVTKKDLVVSAKKENCA

EIIRDVKKMKGLDVNARTVDSVLLNGCKHPVETLYIDEAFACHAGTLRAL

TATIRPKKAVLCGDPKQCGFFNMMCLKVHFNHEICTQVFHKSISRRCTKS

VTSVVSTLFYDKRMRTTNPKETKIVIDTTGSTKPKQDDLILTCFRGWVKQ

LQIDYKGNEIMTAAASQGLTRKGVYAVRYKVNENPLYAPTSEHVNVLLTR

TEDRIVWKTLAGDPWIKILTAKYPGNFTATIEEWQAEHDAIMRHILERPD

PTDVFQNKANVCWAKALVPVLKTAGIDMTTEQWNTVDYFETDKAHSAEIV

LNQLCVRFFGLDLDSGLFSAPTVPLSIRNNHWDNSPSPNMYGLNKEVVRQ

LSRRYPQLPRAVATGRVYDMNTGTLRNYDPRINLVPVNRRLPHALVLHHN

EHPQSDESSFVSKLKGRTVLVVGEKLSVPGKKVDWLSDQPEATFRARLDL

GIPGDVPKYDIVFINVRTPYKYHHYQQCEDHAIKLSMLTKKACLHLNPGG

TCVSIGYGYADRASESIIGAIARQFKFSRVCKPKSSHEETEVLFVFIGYD

RKARTHNPYKLSSTLTNIYTGSRLHEAGC<u>APSYHVVRGDIATATEGVIIN</u>

<u>AANSKGQPGGGVCGALYKKFPESFDLQPIEVGKARLVKGAAKHIIHAVGP</u>

<u>NFNKVSEVEGDKQLAEAYESIAKIVNDNNYKSVAIPLLSTGIFSGNKDRL</u>

<u>TQSLNHLLTALDTTDADVAIYCRDKKWEMTLKEAVARREAVEEICISDDS</u>

<u>SVTEPDAELVRVHPKSSLAGRKGYSTSDGKTFSYLEGTKFHQAAKDIAEI</u>

<u>NAMWPVATEANEQVCMYILGESMSSIRSKCPVEESEASTPPSTLPCLCIH</u>

<u>AMTPERVQRLKASRPEQITVCSSFPLPKYRITGVQKIQCSQPILFSPKVP</u>

<u>AYIHPRKYLVETPPVEETPESPAENQSTEGTPEQPALVNVDATRTRMPEP</u>

<u>IIIEEEEEDSISLLSDGPTHQVLQVEADIHGSPSVSSSSWSIPHASDFDV</u>

<u>DSLSILDTLDGASVTSGAVSAETNSYFARSMEFRARPVPAPRTVERNPPH</u>

<u>PAPRTRTPPLAHSRASSRTSLVSTPPGVNRVITREELEALTPSRAPSRSA</u>

<u>SRTSLVSNPPGVNRVITREEFEAFVAQQQXRFDAGAYIFSSDTGQGHLQQ</u>

KSVRQTVLSEVVLERTELEISYAPRLDQEKEELLRKKLQLNPTPANRSRY

QSRRVENMKAITARRILQGLGHYLKAEGKVECYRTLHPVPLYSSSVNRAF

SSPKVAVEACNAMLKENFPTVASYCIIPEYDAYLDMVDGASCCLDTASFC

PAKLRSFPKKHSYLEPTIRSAVPSAIQNTLQNVLAAATKRNCNVTQMREL

PVLDSAAFNVECFKKYACNNEYWETFKENPIRLTEENVVNYITKLKGPKA

AALFAKTHNLNMLQDIPMDRFVMDLKRDVKVTPGTKHTEERPKVQVIQAA

DPLATADLCGIHRELVRRLNAVLLPNIHTLFDMSAEDFDAIIAEHFQPGD

CVLETDIASFDKSEDDAMALTALMILEDLGVDAELLTLIEAAFGEISSIH

-continued
LPTKTKFKFKGAMMKSGMFLTLFVNTVINIVIASRVLRERLTGSPCAAFIG

DDNIVKGVKSDKLMADRCATWLNMEVKIIDAVVGEKAPYFCGGFILCDSV

TGTACRVADPLKRLFKLGKPLAVDDEHDDDRRRALHEESTRWNRVGILPE

LCKAVESRYETVGTSIIVMAMTTLASSVKSFSYLRGAPITLYG

Amino acid sequence corresponding to nsP3 is underlined.

In this example, amino acid sequence of nsP3 which is corresponding from 1330-1886 in SEQ ID NO: 30 was replaced with the sequence shown below. The underlined sequence was different from SEQ ID NO: 30.

(SEQ ID NO: 31)
APSYHVVRGDIATATEGVIINAANSKGQPGGGVCGALYKKFPESFDLQPI

EVGKARLVKGAAKHIIHAVGPNFNKVSEVEGDKQLAEAYESIAKIVNDNN

YKSVAIPLLSTGIFSGNKDRLTQSLNHLLTALDTTDADVAIYCRDKKWEM

TLKEAVARREAVEEICISDDSSVTEPDAELVRVHPKSSLAGRKGYSTSDG

KTFSYLEGTKFHQAAKDIAEINAMWPVATEANEQVCMYILGKSMSSIRSK

CPVEESEASTPPSTLPCLCIHAMTPERVQRLKASRPEQITVCSSFPLPKY

RITGVQKIQCSQPILFSPKVPAYIHPRKYLVETPPVDETPEPSAENQSTE

GTPEQPPLITEDETRTRTPEPIIIEEEEEDSISLLSDGPTHQVLQVEADI

HGPPSVSSSSWSIPHASDFDVDSLSILDTLEGASVTSGATSAETNSYFAK

SMEFLARPVPAPRTVFRNPPHPAPRTRTPSLAPSRACSRTSLVSTPPGVN

RVITREELEALTPSRTPSRSVSRTSLVSNPPGVNRVITREEFEAFVAQQQ

XRFDAGA

Example 4

Preparation of Alphavirus Replicon Particles

10 μg of the full-length replicon plasmid prepared in Example 3, 1 μg of VEEV Env expression plasmid and 1 μg of VEEV Capsid NLS mutant (or 1 μg VEEV Capsid expression plasmid) was transfected into HEK293T cells. The supernatant was harvested 48-96 hours after transfection. The replicon particle was purified by using an ion exchange column. HET293T or Vero cells were infected with dilutions of the purified particle preparation to determine the infectious titer. The purified replicon particles are used for producing antigens for diagnosis and vaccination.

Example 5

Expression of RBD in HEK293T Cells 293T cells (6.25×10$\hat{5}$ cells/well) were transfected with Fectopro transfection reagent (Polyplus) and 2 ug of each Replicon plasmid. Western blotting was performed on the supernatant directly without purification of particles (left) or on cell lysate fractions (right) 72 h after transfection using antisera reactive with SARS-CoV-2-RBD as a primary antibody and goat anti-rabbit immunoglobulins linked to horseradish peroxidase as a secondary antibody. Also Western blotting was performed for confirming the expression of antigen from Construct K and Construct O in the cell lysate fractions 72 h after transfection using antisera reactive with SARS-CoV-2-RBD as a primary antibody and goat anti-rabbit immunoglobulins linked to horseradish peroxidase as a secondary antibody.

The results are shown in FIG. 3.

The abbreviation means as follows:

ssRBD: construct A hIL-2ssRBD-TM: construct 1 (mouse HA)

ssRBD-linker-TM: construct C (TM1: mouse CD80, Linker: mouse IgG4-CH$_3$)

Mouse: CD80(TM-Cyt)

(SEQ ID NO: 32)
TLVLFGAGFGAVITVVVIVVIIKCFCKHRSCFRRNEASRETNNSLTFGPE

EALAEQTVFL

Mouse IgG4-CH$_3$ (SEQ ID NO: 33)
GRPKAPQVYTIPPPKEQMAKDKVSLTCMITNFFPEDITVEWQWNGQPAEN

YKNTQPINDTDGSYFVYSKLNVQKSNWEAGNTFTCSVLHEGLHNHHTEKS

LSHSPGK

Expressions were confirmed for all tested particles in the cells. As expected the ssRBD without a transmembrane sequence was secreted into the medium of the cell culture, whereas each of the RBD constructs linked to a transmembrane sequence was retained in the cells and not secreted into the media.

Example 6

Immunogenicity

The following Replicon Particle Vaccines prepared in Example 4 were used.

VRep ssRBD: VEEV particle packaging construct A

VRep sshIL2 RBD HA: VEEV particle packaging construct 1

VRep ssRBD mIgG4 CD80: VEEV Replicon particle packaging Construct C (TM1:

mouse CD80, Linker: mouse IgG4-CH$_3$)

Control: VEEV Replicon without gene of interest

DNA vaccine: DNA expressing the spike protein of SARS-CoV-2

Mice were immunized intramuscularly three times (on Day0, Day7 and Day14) with the indicated Replicon particles (RBD or RBD-linker-TM, 10^7IU/dose), a control Replicon particle or a DNA vaccine (20 ug/dose), and sera were collected on Day14 (7 days after 2nd immunization) and Day35 (21 days after 3nd immunization). These sera were examined in ELISA assays performed against a SARS-CoV-2-Spike S1 or RBD antigen. The symbols show the average of the five mice in each group, and error bars show the s.e.m. The curve fit was calculated by Prism software. These results are shown in FIGS. 4-1-1, 4-1-2 and 4-2 and FIGS. 5-1-1, 5-1-2 and 5-2.

FIGS. 4-1-1, 4-1-2 and 4-2 and FIGS. 5-1-1, 5-1-2 and 5-2 show that significantly higher titers of antibody against recombinant Coronavirus RBD and Spike S1 were achieved after immunization with replicon vaccines. In contrast, very low titers of antibody were induced with the DNA vaccine.

Example 7

Immunogenicity
The following Replicon Particle Vaccines prepared in Example 4 were used.
CD80: VEEV particle packaging Construct C
HA No. 1: VEEV particle packaging Construct K
Control: PBS Mice were immunized intramuscularly with the indicated Replicon vaccines (CD80 or HA No. 1, 10^5IU/dose) or PBS, and sera were collected 7 days after immunization. These sera were subject to ELISA analysis performed against a SARS-CoV-2-Spike S1 antigen. The symbols show the mean of the five mice in each group, and error bars show the s.e.m. These results are shown in FIG. 6.

Figure 6:
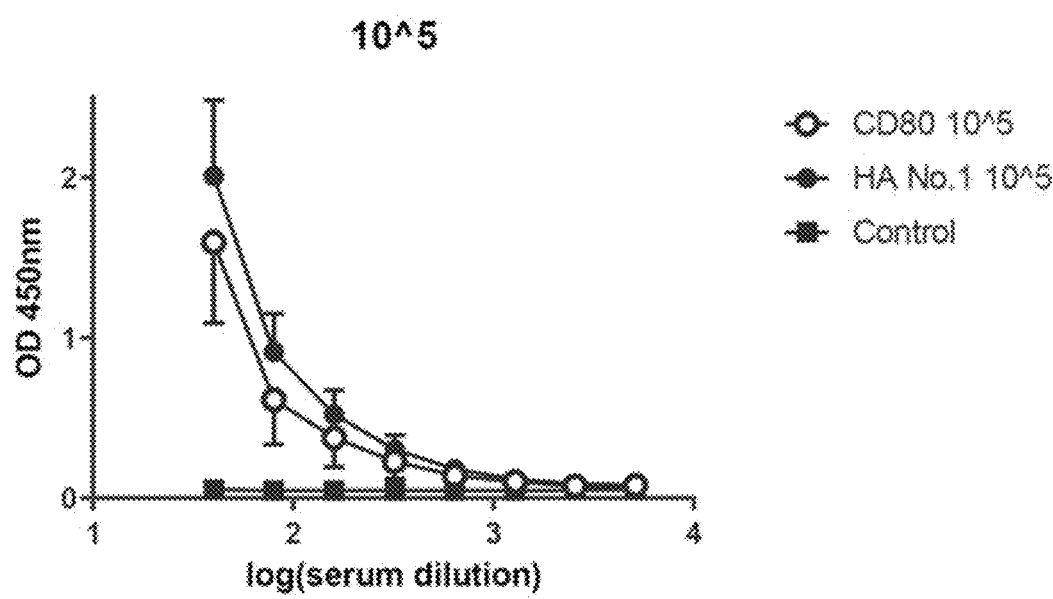
FIG. 6
Antibody titer against SARS-CoV-2 Spike S1 antigen in mice sera on day 7 immunization with the alphavirus replicon particles prepared in Example 4.

FIG. 6 shows that significantly higher titers of antibody against recombinant Coronavirus Spike S1 were achieved after immunization with replicon vaccines.

Example 8

Preparation of self-amplifying RNA (saRNA) encapsulated in lipid nanoparticles (LNP) The vector comprising the DNA sequence encoding construct C prepared in Example 3 was used. The DNA was linearized and used as the template. T7 in vitro transcription was conducted based on protocols provided by the T7 transcription kit (RiboMax™ Express Large Scale RNA production System, Promega, (WI USA)). The linear DNA template was mixed with T7 enzyme and rNTPs to synthesize RNA. The purified RNA product was capped using vaccinia capping enzyme to give self-amplifying RNA.

The obtained saRNA was encapsulated in lipid nanoparticles to give saRNA(RBD-CD80TM) particles. Lipid nanoparticles with no RNA was used as control.

Example 9

Immunization
saRNAs formulated with LNP prepared in Example 8 were used.
Amount of immunization:
0.3 ug saRNA(RBD-CD80TM)
1 ug saRNA(RBD-CD80TM)
10 ug saRNA(RBD-CD80TM)
no RNA (control)

The indicated amount of saRNA or no RNA (control) formulated with LNP (Genvoy) were used. The 4-6 weeks old mice (n=5 per group) were immunized with saRNA formulated with LNP on Day 0 and Day 28 by intramuscularly injections.

The mice were bleed on Day 14, 28 and 46. The antibody titer against S1 protein in the sera from the immunized mice were measured by ELISA. The plate were coated with S1 protein (Sinobio 100 ng/ml). Results are shown in FIG. 6.

Example 10

The SARS-CoV-2 RBD may be derived from SARS-CoV-2 mutants. The following amino acid sequences of constructions comprising the SARS-CoV-2 signal sequence, SARS-CoV-2 RBD derived from a SARS-CoV-2 mutant, and human HA(flexible-TM-Cyt) are also used for generating alphavirus replicon as shown in FIG. 1. In this example the gene of interest is replaced with the polynucleotide encoding the following amino acid sequence. Self-amplifying RNA (saRNA) encapsulated in lipid nanoparticles (LNP) is generated in the same manner as Example 8.

Construct derived from SARS-CoV-2 E484K_N501Y_K417T mutant (Brazil Strain Mutant)

(SEQ ID NO: 34)
MFVFLVLLPLVSSVRFPNITNLCPFGEVFNATRFASVYAWNRKRISNCVA
DYSVLYNSASFSTFKCYGVSPTKLNDLOFTNVYADSFVIRGDEVRQIAPG
QTGTIADYNYKLPDDFTGCVIAWNSNNLDSKVGGNYNYLYRLFRKSNLKP
FERDISTEIYQAGSTPCNGVKGFNCYFPLQSYGFQPTYGVGYQPYRVVVL
SFELLHAPATVCGPKKSTGVKLESMGIYQILAIYSTVASSLVLLVSLGAI
SFWMCSNGSLQCRICI

Construct derived from SARS-CoV-2 E484K_N501Y_K417N mutant (South African Mutant)

(SEQ ID NO: 35)
MFVFLVLLPLVSSVRFPNITNLCPFGEVFNATRFASVYAWNRKRISNCVA
DYSVLYNSASFSTFKCYGVSPTKLNDLCFTNVYADSFVIRGDEVRQIAPG
QTGNIADYNYKLPDDFTGCVIAWNSNNLDSKVGGNYNYLYRLFRKSNLKP
FERDISTEIYQAGSTPCNGVKGFNCYFPLQSYGFQPTYGVGYQPYRVVVL
SFELLHAPATVCGPKKSTGVKLESMGIYQILAIYSTVASSLVLLVSLGAI
SFWMCSNGSLQCRICI

Construct Derived from SARS-CoV-2 E484K Mutant (SEQ ID NO 36)
MFVFLVLLPLVSSVRFPNITNLCPFGEVFNATRFASVYAWNRKRISNCVA
DYSVLYNSASFSTFKCYGVSPTKLNDLCFTNVYADSFVIRGDEVRQIAPG
QTGKIADYNYKLPDDFTGCVIAWNSNNLDSKVGGNYNYLYRLFRKSNLKP
FERDISTEIYQAGSTPCNGVKGFNCYFPLQSYGFQPTNGVGYQPYRVVVL
SFELLHAPATVCGPKKSTGVKLESMGIYQILAIYSTVASSLVLLVSLGAI
SFWMCSNGSLQCRICI Specific Embodiments provided by this disclosure are as follows:

(1) An isolated polynucleotide, which encodes alphavirus non-structural proteins nsP1, nsP2, nsP3 and nsP4 and a polypeptide comprising a coronavirus protein fused to a signal sequence and/or transmembrane domain.

(2) The polynucleotide of (1), wherein the coronavirus protein is a spike (S) protein, nucleocapsid (N) protein, membrane (M) protein, small envelope (E) protein or a combination thereof.

(3) The polynucleotide of (1), wherein the coronavirus protein is a spike (S) protein.

(4) The polynucleotide of (1), wherein the coronavirus protein is a S1 and/or S2 subunit of a spike (S) protein.

(5) The polynucleotide of (4), wherein the coronavirus protein is a S1 subunit in a spike (S) protein.

(6) The polynucleotide of (5), wherein the coronavirus protein is a receptor binding domain of the S1 subunit.

(7) The polynucleotide of any one of (1) to (6), wherein the transmembrane domain is derived from Influenza Hemagglutinin (HA), CD80 or TLR4.

(8) The polynucleotide any one of (1) to (6), wherein the transmembrane domain is a modified transmembrane domain derived from coronavirus structural protein.

(9) The polynucleotide of (8), the modified transmembrane domain comprises juxtamembrane domain and transmembrane domain of SARS-CoV-2 Spike (S).

(10) The polynucleotide of any one of (1) to (9), wherein coronavirus protein is fused to a signal sequence and transmembrane domain.

(11) The polynucleotide of any one of (1) to (10), wherein the signal sequence is derived from human IL-2.

(12) The polynucleotide of any one of (1) to (10), wherein the signal sequence is derived from SARS-CoV-2 spike protein.

(13) The polynucleotide of any one of (1) to (12), wherein the transmembrane domain and/or signal sequence is fused to the coronavirus protein by a linker.

(14) The polynucleotide of (13) wherein the linker is IgG4CH$_3$ and/or short linker.

(15) The polynucleotide of any one of (1) to (14), wherein the coronavirus is SARS-CoV-2.

(16) The polynucleotide of (15), wherein the polypeptide encodes an amino acid sequence selected from SEQ ID NOs 1, 5, 6, 8, 9, 11, 12, 13, 34, 35 and 36.

(17) The polynucleotide of (15), wherein the polypeptide encodes an amino acid sequence selected from SEQ ID NOs 37-51.

(18) The polynucleotide of any one of (1) to (17), wherein the polynucleotide is RNA.

(19) The polynucleotide of any one of (1) to (17), wherein the polynucleotide is DNA.

(20) A vector comprising the polynucleotide of any one of (1) to (19).

(21) The vector of (20), which comprises a promoter, 5' UTR, polynucleotide encoding alphavirus non-structural proteins nsP1, nsP2, nsP3 and nsP4, SG promoter, a gene of interest encoding the polypeptide comprising a coronavirus protein fused to a signal sequence and/or transmembrane domain, 3'UTR and poly A tail.

(22) A vaccine composition comprising the polynucleotide or vector of any one of (1) to (21) and a pharmaceutically acceptable carrier.

(23) The vaccine composition of (22), wherein the pharmaceutically acceptable carrier is a delivery vehicle.

(24) The vaccine composition of (23), wherein the delivery vehicle is a particle consisting of one or more alphavirus structural proteins or a lipid delivery system.

(25) Use of the polynucleotide or vector of any one of (1) to (21) for the manufacture of a medicament.

(26) Use of (25), wherein the medicament is for inducing immunomodulation in a subject.

(27) Use of (25), wherein the medicament is for treating or preventing a subject from conditions caused by coronavirus infection.

(28) A method of immunomodulation in a subject, comprising administering an immunologically effective amount of the vaccine composition of any one of (22) to (24), to the subject in need thereof.

(29) A method of treating, preventing and/or immunizing against coronavirus viral infection in a subject, comprising administering an effective amount of the vaccine composition of any one of (22) to (24), to the subject in need thereof.

(30) A polypeptide comprising a coronavirus structural protein fused to a signal sequence and/or heterologous transmembrane domain.

What is claimed is:

1. An isolated polynucleotide, which encodes alphavirus non-structural proteins nsP1, nsP2, nsP3, and nsP4 and
    a polypeptide comprising a receptor binding domain (RBD) of an S1 subunit in a spike protein of a SARS-CoV2 fused to a transmembrane domain and optionally to a signal sequence,
    wherein the alphavirus is Venezuelan Equine Encephalitis Virus or Chikungunya virus, and
    wherein the transmembrane domain is heterologous to the SARS-CoV-2.

2. The polynucleotide of claim 1, wherein the transmembrane domain is derived from Influenza Hemagglutinin (HA) or CD80.

3. The polynucleotide of claim 2, wherein the transmembrane domain is derived from Influenza Hemagglutinin (HA).

4. The polynucleotide of claim 1, wherein coronavirus protein is fused to a signal sequence and transmembrane domain.

5. The polynucleotide of claim 1, wherein the signal sequence is derived from human IL-2 or SARS-CoV-2 spike protein.

6. The polynucleotide of claim 1, wherein the transmembrane domain and/or signal sequence is fused to the coronavirus protein by a linker.

7. The polynucleotide of claim 1, wherein the linker is IgG4CH$_3$ and/or a short linker.

8. The polynucleotide of claim 1, wherein the polynucleotide encodes an amino acid sequence selected from SEQ ID NOs: 1, 5, 6, 8, 9, 11, 12, 13, 34, 35, 36 and 37-51.

9. The polynucleotide of claim 1, wherein the polynucleotide is RNA.

10. A vector comprising the polynucleotide of claim 1.

11. The vector of claim 10, which further comprises a promoter, 5' UTR, SG promoter, 3'UTR and poly A tail.

12. A vaccine composition comprising (i) the polynucleotide of claim 1 or an expression vector containing the polynucleotide and (ii) a pharmaceutically acceptable delivery vehicle.

13. The vaccine composition of claim 12, wherein the delivery vehicle is a particle consisting of one or more alphavirus structural proteins or a lipid delivery system.

14. The polynucleotide of claim 1, wherein the alphavirus is Venezuelan Equine Encephalitis Virus.

15. A vaccine composition comprising (i) the polynucleotide of claim 1 or an expression vector containing the polynucleotide, and (ii) a pharmaceutically acceptable lipid delivery system.

16. The polynucleotide of claim 1, wherein the receptor binding domain (RBD) of the S1 subunit in a spike protein of a SARS-CoV2 is SEQ ID NO: 19.

* * * * *